United States Patent [19]

Cousens et al.

[11] Patent Number: 5,977,308

[45] Date of Patent: *Nov. 2, 1999

[54] PLATELET-ACTIVATING FACTOR ACETYLHYDROLASE

[75] Inventors: Lawrence S. Cousens, Oakland, Calif.; Christine D. Eberhardt, Redmond, Wash.; Patrick Gray, Seattle, Wash.; Hai Le Trong, Edmonds, Wash.; Larry W. Tjoelker, Kirkland, Wash.; Cheryl L. Wilder, Seattle, Wash.

[73] Assignee: ICOS Corporation, Bothell, Wash.

[ * ] Notice: This patent is subject to a terminal disclaimer.

[21] Appl. No.: 08/910,041

[22] Filed: Aug. 12, 1997

Related U.S. Application Data

[63] Continuation-in-part of application No. 08/483,232, Jun. 7, 1995, Pat. No. 5,656,431, which is a continuation-in-part of application No. 08/318,905, Oct. 6, 1994, Pat. No. 5,641,669, which is a continuation-in-part of application No. 08/133,803, Oct. 6, 1993, abandoned.

[51] Int. Cl.$^6$ .............................. C07K 14/00; C07K 5/00; C07H 21/04
[52] U.S. Cl. .............................. 530/350; 530/300; 514/2; 536/23.1; 536/23.2
[58] Field of Search .................................. 530/300, 350; 514/2; 536/23.1, 23.2

[56] References Cited

U.S. PATENT DOCUMENTS

| | | | |
|---|---|---|---|
| 5,019,508 | 5/1991 | Johnson et al. | 435/198 |
| 5,279,957 | 1/1994 | Gross | 435/348 |

FOREIGN PATENT DOCUMENTS

| | | |
|---|---|---|
| 9400413 | 1/1994 | United Kingdom . |
| 9313144 | 6/1994 | United Kingdom . |
| 94/20069 | 9/1994 | WIPO . |
| 95/00649 | 1/1995 | WIPO . |

OTHER PUBLICATIONS

Adjei and Garren, "Pulmonary Delivery of Peptide Drugs: Effect of Particle Size on Bioavailability of Leuprolide Acetate in Healthy Male Volunteers", *Pharm. Res.*, 7(6):565–569 (1990).

Banker and Cowan, "Rat Hippocampal Neurons in Dispersed Cell Culture," *Brain Res.*, 126:397–425 (1977).

Basran, "Properties of Platelet Activating Factor (PAF–ACETHER) Which Suggest Involvement in Chronic Inflammation and Persistent Asthma", *Br. J. Pharmacol.*, 77:437 (1982).

Braquet et al., "Effect of Endothelin–1 on Blood Pressure and Bronchopulmonary System of the Guinea Pig", *J. Cardio. Pharm.*, 13(Supp. 5):S143–S146 (1989).

Brenner, "The molecular evolution of genes and proteins: a tale of two serines", *Nature*, 334:528–530 (Aug. 11, 1988).

Capecchi, "Altering the Genome by Homologous Recombination", *Science*, 244:1288–1292 (Jun. 16, 1989).

Caplan et al., "Role of Platelet Activating Factor and Tumor Necrosis Factor–Alpha in Neonatal Necrotizing Enterocolitis," *Pediatr. Pathol.*, 14:1017–1028 (1994).

Caplan et al., "Role of Platelet activating factor and tumor necrosis factor–alpha in neonatal necrotizing enterocolitis", *J. Pediatr.*, 116(6):960–964 (Jun. 1990).

Chapus et al., "Minireview on pancreatic lipase and colipase", *Biochimie*, 70:1223–1224 (1988).

deBoer et al., "The tac promoter: A functional hybrid derived from the trp and lac promoters", *Proc. Natl. Acad. Sci. USA*, 80:21–25 (Jan. 1983).

Debs et al., "Lung–Specific Delivery of Cytokines Induces Sustained Pulmonary and Systemic Immunomodulation in Rats", *J. Immunol.*, 140(10):3462–3488 (May 15, 1933).

Denizot et al., "PAF Acether and Acetylhydrolase in Stool of Patients with Crohn's Disease," *Digestive Diseases and Sciences*, 37(3):432–437 (1992).

Furukawa et al., "Platelet–Activating Factor–Induced Ischemic Bowel Necrosis: The Effect of Platelet–Activating Factor Acetylhydrolase", *Ped. Res.*, 34(2):237–241 (1993).

Genis et al., "Cytokines and Arachidonic Metabolites Produced During Human Immunodeficiency Virus (HIV)–Infected Macrophage–Astroglia Interactions: Implications for the Neuropathogenesis of HIV Disease," *Exp. Med.*, 176:1703–1718 (1992).

Grino et al., "BN 52021: A Platelet Activating Factor Antagonist for Preventing Post–Transplant Renal Failure", *Anna. Int. Med.*, 121(5):345–347 (Sep. 1, 1994).

Hahn et al., "The complete sequences of plasmids pFNeo and pMH–Neo: convenient expression vectors for high–level expression of eukaryotic genes in hematopoietic cell lines", *Gene*, 127:267–268 (1993).

Handley and Saunders, "Platelet Activating Factor and Inflammation in Atherogenesis: Targets for Drug Development", *Drug. Dev. Res.*, 7:361–375 (1986).

Hattori et al., "Purification and Characterization of Bovine Brain Platelet–activating Factor Acetylhydrolase", *J. Biol. Chem.*, 268(25):18748–18753 (Sep. 5, 1993).

Hattori et al., "The Catalytic Subunit of Bovine Brain Platelet–activating Factor Acetylhydrolase Is a Novel Type of Serine Esterase", *J. Biol. Chem.*, 269(37):23150–23155 (Sep. 16, 1994).

Henriques et al., "Endothelin–1 inhibits PAF–induced paw oedema and pleurisy in the mouse", *Br. J. Pharmacol.*, 106:579–582 (1992).

(List continued on next page.)

*Primary Examiner*—George C. Elliott
*Assistant Examiner*—Sean McGarry
*Attorney, Agent, or Firm*—Marshall, O'Toole, Gerstein, Murray & Borun

[57] ABSTRACT

The present invention provides purified and isolated polynucleotide sequences encoding human plasma platelet-activating factor acetylhydrolase. Also provided are materials and methods for the recombinant production of platelet-activating factor acetylhydrolase products which are expected to be useful in regulating pathological inflammatory events.

9 Claims, 13 Drawing Sheets

OTHER PUBLICATIONS

Heuer, "Current status of PAF antagonists", *Clin. Exp. Allergy,* 22:980–983 (1992).

Hoffman et al., "Detection of platelet–activating factor in amniotic fluid of complicated pregnancies", *Am. J. Obstet. Gynecol.,* 162(2):525–528 (1990).

Horwitz et al., "DNA sequences of the araBAD–araC controlling region in *Salmonella typhimurium* LT2", *Gene,* 14:309–319 (1981).

Hsieh and Ng, "Increased plasma platelet–activating factor in children with acute asthmatic attacks and decreased in vivo and in vitro production of platelet–activating factor after immunotherapy", *J. Allergy Clin. Immunol.,* 91:650–657 (Feb. 1993).

Caplan et al., "Platelet–activating factor, tumor necrosis factor, hypoxia and necrotizing enterocolitis", *Acta Paediatr.,* Suppl. 396:11–17 (1994).

Hubbard et al., "Anti–Neutrophil–Elastase Defenses of the Lower Respiratory Tract in α1–Antitrypsin Deficiency Directly Augmented with an Aerosol of A1–Antitrypsin", *Annals of Internal Medicine,* III(3):206–212 (Aug. 1, 1989).

Kald et al., "Release of Platelet–Activating Factor in Acute Experimental Pancreatitis", *Pancreas,* 8(4):440–442 (1993).

Kalter et al., "Enhanced HIV Replication in Macrophage Colony–Stimulating Factor–Treated Monocytes," *J. Immunol.,* 146:298–306 (1991).

Kirsch et al., "Mechanism of Platelet Activating Factor–Induced Vascular Leakage in the Rat Trachea", *Exp. Lung Res.,* 18:447–459 (1992).

Yamashita et al., "Increased levels of blood platelet–activating factor in bronchial asthmatic patients with active symptoms", *Allergy,* 49:60–63 (1994).

LaVallie et al., "A Thioredoxin Gene Fusion Expression System That Circumvents Inclusion Body Formation in the *E. coli* Cytoplasma", *Bio/Technology,* 11:187–193 (Feb. 11, 1993).

Lellouch–Tubiana et al., "Eosinophil Recruitment into Guinea Pig Lungs after PAF–acether and Allergen Administration", *Am. Rev. Respir. Dis.,* 137:948–954 (1988).

Lellouch–Tubiana et al., "Ultrastructural evidence for extravascular platelet recruitment in the lung upon intravenous injection of platelet–activating factor (PAF–acether) into guinea–pigs", *Br. J. Exp Path.,* 66:345–355 (1985).

Lewin, pp. 136–141 in *Genes V,* Oxford University Press, New York, New York (1994).

Lindsberg et al., "Evidence for Platelet–Activating Factor as a Novel Mediator in Experimental Stroke in Rabbits", *Stroke,* 21(10):1452–1457 (Oct. 1990).

Lindsberg et al., "Platelet–activating Factor in Stroke and Brain Injury", *Ann. Neurol.,* 30(2):117–129 (Aug. 1991).

Maki et al., "Platelet–activating factor acetylhydrolase activity in maternal, fetal, and newborn rabbit plasma during pregnancy and lactation", *Proc. Natl. Acad. Sci. USA,* 85:728–732 (Feb. 1988).

Matsumoto et al., "Platelet–Activating Factor in Bronchoalveolar Lavage Fluid of Patients With Adult Respiratory Distress Syndrome", *Clin. Exp. Pharmacol. Physiol.,* 19:509–515 (1992).

Matsuzaki et al., "PAF acetylhydrolase activities in human systemic lupus erythematosus and lupus–prone mice", *Clinica Chimica Acta,* 210:139–144 (1992).

Mezzano et al., "Detection of Platelet–Activating Factor in Plasma of Patients with Streptococcal Nephritis", *J. Am. Soc. Nephrol.,* 4:235–242 (1993).

Miwa et al., "Characterization of Serum Platelet–activating Factor (PAF) Acetylhydrolase", *J. Clin. Invest.,* 82:1983–1991 (Dec. 1988).

Pierre et al., "A New Enzymatic Kinetic Method For Determination of α–Amylase," *Clin. Chem.,* 22:1219 (1976).

Rabinovici et al., "ARDS–like lung injury produced by endotoxin in platelet–activating factor–primed rats", *J. Appl. Physiol.,* 74(4):1791–1802 (1993).

Rabinovici et al., "Platelet Activating Factor Mediates Interleukin–2–induced Lung Injury in the Rat", *J. Clin. Invest.,* 89:1669–1673 (May 1992).

*Remington's Pharmaceutical Sciences,* 18$^{th}$ Edition, Mack Publishing Co., Easton, PA (1990).

Rodriguez–Roisin et al., "Platelet–activating Factor Causes Ventilation–Perfusion Mismatch in Humans", *J. Clin. Invest.,* 93:188–194 (Jan. 1994).

Sandhu et al., "Amplification of Reproducible Allele Markers for Amplified Fragment Length Polymorphism Analysis", *Biotechniques,* 12(1):14–16 (1992).

Satoh et al., "Platelet–activating Factor (PAF) Stimulates the Production of PAF Acetylhydrolase by the Human Hepatoma Cell Line, HepG2", *J. Clin. Invest.,* 87:476–481 (Feb. 1991).

Satoh et al., Platelet–Activating Factor Acetylhydrolase in Plasma Lipoproteins From Patients With Ischemic Stroke, *Stroke,* 23:1090–1092 (1992).

Smith et al., "Pulmonary Deposition and Clearance of Aerosolized Alpha–1–Proteinase Inhibitor Administered to Dogs and to Sheep", *J. Clin. Invest.,* 84:1145–1154 (Oct. 1989).

Stafforini et al., "Human Macrophages Secrete Platelet–activating Factor Acetylhydrolase", *J. Biol. Chem.,* 265(17):9682–9687 (Jun. 15, 1990).

Stafforini et al., "Human Plasma Platelet–activating Factor Acetylhdrolase: Association with lipoprotein particles and role in the degradation of platelet–activating factor", *J. Biol. Chem.,* 262(9):4215–4222 (Mar. 25, 1987).

Stafforini et al., "Human Plasma Platelet–activating Factor Acetylhydrolase: Purification and Properties", *J. Biol. Chem.,* 262(9):4223–4230 (Mar. 25, 1987).

Stafforini et al., "Lipoproteins alter the catalytic behavior of the platelet–activating factor acetylhydrolase in human plasma", *Proc. Natl. Acad. Sci.,* 86:2393–2397 (Apr. 1989).

Stafforini et al., "Platelet–activating factor acetylhydrolase activity in human tissues and blood cells", *Lipids,* 26(12):979–985 (1991).

Stafforini et al., "The Platelet–activating Factor Acetylhydrolase from Human Erythrocytes: Purification and Properties", *J. Biol. Chem.,* 268(6):3857–3865 (Feb. 25, 1993).

Stremler et al., "Human Plasma Platelet–activating Factor Acetylhydrolase", *J. Biol. Chem.,* 266(17):11095–11103 (Jun. 15, 1991).

Tarbet et al., "Liver Cells Secrete the Plasma Form of Platelet–activating Factor Acetylhydrolase", *J. Biol. Chem.,* 266(25):16667–16673 (Sep. 1991).

Tjoelker et al., "Anti–Inflammatory Properties of a Platelet–Activating Factor Acetylhydrolase,"*Nature,* 374:549–552 (Apr. 6, 1995).

Venable et al., "Platelet–activating factor: a phospholipid autacoid with diverse actions", *J. Lipid Res.,* 34:691–701 (1993).

von Heijen, "A new method for predicting signal sequence cleavage sites", *Nuc. Acids Res.*, 14(11):4683–4690 (1986).

Wada et al., "Codon Usage tabulated from the GenBank Genetic sequence data", *Nuc. Acids Res.*, 19S:1981–1986 (1991).

Watanabe et al., "Pharmacological analysis of neutrophil chemotactic factor production by leucocytes and roles of PAF in allergic inflammation in rats", *Br. J. Pharmacol.*, 111:123–130 (1994).

Watson et al., "The Platelet–Activating Factor Antagonist Web 2170 Its Beneficial Efect on Dog Renal Allograft Surivival", *Transplantation*, 56(4):1047–1049 (Oct. 1993).

Yasuda and Johnston, "The Hormonal Regulation of Platelet–Activating Factor–Acetylhydrolase in the Rat", *Endocrinology*, 130(2):708–716 (1992).

Zarco et al., "Involvement of platelet–activating factor and tumor necrosis factor in the pathogenesis of joint inflammation in rabbits", *Clin exp. Immunol.*, 88:318–323 (1992).

10

```
                          SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
         (A) LENGTH: 17 amino acids
         (B) TYPE: amino acid
         (D) TOPOLOGY: linear (ii) MOLECULE TYPE: peptide (xi) SEQUENCE DESCRIPTION: SEQ ID NO:1:

Phe Lys Asp Leu Gly Glu Glu Asn Phe Lys Ala Leu Val Leu Ile Ala
1               5                  10                  15

Phe (2) INFORMATION FOR SEQ ID NO:2:

(i) SEQUENCE CHARACTERISTICS:
         (A) LENGTH: 16 amino acids
         (B) TYPE: amino acid
         (D) TOPOLOGY: linear (ii) MOLECULE TYPE: peptide (xi) SEQUENCE DESCRIPTION: SEQ ID NO:2:

Ile Gln Val Leu Met Ala Ala Ala Ser Phe Gly Gln Thr Lys Ile Pro
1               5                  10                  15

(2) INFORMATION FOR SEQ ID NO:3:

(i) SEQUENCE CHARACTERISTICS:
         (A) LENGTH: 11 amino acids
         (B) TYPE: amino acid
         (D) TOPOLOGY: linear (ii) MOLECULE TYPE: peptide (xi) SEQUENCE DESCRIPTION: SEQ ID NO:3:

Met Lys Pro Leu Val Val Phe Val Leu Gly Gly
1               5                  10

(2) INFORMATION FOR SEQ ID NO:4:
```

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: Modified-site
    (B) LOCATION: group(13, 21, 27)
    (C) OTHER INFORMATION: /note= "The nucleotide at each of
        these positions is an inosine."

(xi) SEQUENCE DESCRIPTION: SEQ ID NO:4:

ACATGAATTC GGNATCYTTG NGTYTGNCCR AA                            32

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TATTTCTAGA AGTGTGGTGG AACTCGCTGG                               30

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CGATGAATTC AGCTTGCAGC AGCCATCAGT AC                            32

(2) INFORMATION FOR SEQ ID NO:7:

(i) SEQUENCE CHARACTERISTICS:
        (A) LENGTH: 1520 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 162..1484

(xi) SEQUENCE DESCRIPTION: SEQ ID NO:7:

GCTGGTCGGA GGCTCGCAGT GCTGTCGGCG AGAAGCAGTC GGGTTTGGAG CGCTTGGGTC    60

GCGTTGGTGC GCGGTGGAAC GCGCCCAGGG ACCCCAGTTC CCGCGAGCAG CTCCGCGCCG   120

CGCCTGAGAG ACTAAGCTGA AACTGCTGCT CAGCTCCCAA G ATG GTG CCA CCC       173
                                              Met Val Pro Pro
                                                1

AAA TTG CAT GTG CTT TTC TGC CTC TGC GGC TGC CTG GCT GTG GTT TAT     221
Lys Leu His Val Leu Phe Cys Leu Cys Gly Cys Leu Ala Val Val Tyr
  5                  10                  15                  20

CCT TTT GAC TGG CAA TAC ATA AAT CCT GTT GCC CAT ATG AAA TCA TCA     269
Pro Phe Asp Trp Gln Tyr Ile Asn Pro Val Ala His Met Lys Ser Ser

-continued

|  | 25 |  |  |  | 30 |  |  |  | 35 |  |  |  |  |
|---|---|---|---|---|---|---|---|---|---|---|---|---|---|
| GCA | TGG | GTC | AAC | AAA | ATA | CAA | GTA | CTG | ATG | GCT | GCT | GCA | AGC TTT GGC | 317 |
| Ala | Trp | Val | Asn | Lys | Ile | Gln | Val | Leu | Met | Ala | Ala | Ala | Ser Phe Gly |  |
|     |     |     | 40  |     |     |     |     | 45  |     |     |     | 50  |             |  |

| CAA | ACT | AAA | ATC | CCC | CGG | GGA | AAT | GGG | CCT | TAT | TCC | GTT | GGT TGT ACA | 365 |
| Gln | Thr | Lys | Ile | Pro | Arg | Gly | Asn | Gly | Pro | Tyr | Ser | Val | Gly Cys Thr |  |
|     |     | 55  |     |     |     |     | 60  |     |     |     |     | 65  |             |  |

| GAC | TTA | ATG | TTT | GAT | CAC | ACT | AAT | AAG | GGC | ACC | TTC | TTG | CGT TTA TAT | 413 |
| Asp | Leu | Met | Phe | Asp | His | Thr | Asn | Lys | Gly | Thr | Phe | Leu | Arg Leu Tyr |  |
|     | 70  |     |     |     |     | 75  |     |     |     |     | 80  |     |             |  |

| TAT | CCA | TCC | CAA | GAT | AAT | GAT | CGC | CTT | GAC | ACC | CTT | TGG | ATC CCA AAT | 461 |
| Tyr | Pro | Ser | Gln | Asp | Asn | Asp | Arg | Leu | Asp | Thr | Leu | Trp | Ile Pro Asn |  |
| 85  |     |     |     |     | 90  |     |     |     |     | 95  |     |     | 100         |  |

| AAA | GAA | TAT | TTT | TGG | GGT | CTT | AGC | AAA | TTT | CTT | GGA | ACA | CAC TGG CTT | 509 |
| Lys | Glu | Tyr | Phe | Trp | Gly | Leu | Ser | Lys | Phe | Leu | Gly | Thr | His Trp Leu |  |
|     |     |     |     | 105 |     |     |     |     | 110 |     |     |     | 115         |  |

| ATG | GGC | AAC | ATT | TTG | AGG | TTA | CTC | TTT | GGT | TCA | ATG | ACA | ACT CCT GCA | 557 |
| Met | Gly | Asn | Ile | Leu | Arg | Leu | Leu | Phe | Gly | Ser | Met | Thr | Thr Pro Ala |  |
|     |     |     | 120 |     |     |     |     | 125 |     |     |     |     | 130         |  |

| AAC | TGG | AAT | TCC | CCT | CTG | AGG | CCT | GGT | GAA | AAA | TAT | CCA | CTT GTT GTT | 605 |
| Asn | Trp | Asn | Ser | Pro | Leu | Arg | Pro | Gly | Glu | Lys | Tyr | Pro | Leu Val Val |  |
|     |     | 135 |     |     |     |     | 140 |     |     |     |     | 145 |             |  |

| TTT | TCT | CAT | GGT | CTT | GGG | GCA | TTC | AGG | ACA | CTT | TAT | TCT | GCT ATT GGC | 653 |
| Phe | Ser | His | Gly | Leu | Gly | Ala | Phe | Arg | Thr | Leu | Tyr | Ser | Ala Ile Gly |  |
| 150 |     |     |     |     | 155 |     |     |     |     | 160 |     |     |             |  |

| ATT | GAC | CTG | GCA | TCT | CAT | GGG | TTT | ATA | GTT | GCT | GCT | GTA | GAA CAC AGA | 701 |
| Ile | Asp | Leu | Ala | Ser | His | Gly | Phe | Ile | Val | Ala | Ala | Val | Glu His Arg |  |
| 165 |     |     |     |     | 170 |     |     |     |     | 175 |     |     | 180         |  |

| GAT | AGA | TCT | GCA | TCT | GCA | ACT | TAC | TAT | TTC | AAG | GAC | CAA | TCT GCT GCA | 749 |
| Asp | Arg | Ser | Ala | Ser | Ala | Thr | Tyr | Tyr | Phe | Lys | Asp | Gln | Ser Ala Ala |  |
|     |     |     |     | 185 |     |     |     |     | 190 |     |     |     | 195         |  |

| GAA | ATA | GGG | GAC | AAG | TCT | TGG | CTC | TAC | CTT | AGA | ACC | CTG | AAA CAA GAG | 797 |
| Glu | Ile | Gly | Asp | Lys | Ser | Trp | Leu | Tyr | Leu | Arg | Thr | Leu | Lys Gln Glu |  |
|     |     |     | 200 |     |     |     |     | 205 |     |     |     |     | 210         |  |

| GAG | GAG | ACA | CAT | ATA | CGA | AAT | GAG | CAG | GTA | CGG | CAA | AGA | GCA AAA GAA | 845 |
| Glu | Glu | Thr | His | Ile | Arg | Asn | Glu | Gln | Val | Arg | Gln | Arg | Ala Lys Glu |  |
|     |     |     | 215 |     |     |     |     | 220 |     |     |     |     | 225         |  |

| TGT | TCC | CAA | GCT | CTC | AGT | CTG | ATT | CTT | GAC | ATT | GAT | CAT | GGA AAG CCA | 893 |
| Cys | Ser | Gln | Ala | Leu | Ser | Leu | Ile | Leu | Asp | Ile | Asp | His | Gly Lys Pro |  |
| 230 |     |     |     |     | 235 |     |     |     |     | 240 |     |     |             |  |

| GTG | AAG | AAT | GCA | TTA | GAT | TTA | AAG | TTT | GAT | ATG | GAA | CAA | CTG AAG GAC | 941 |
| Val | Lys | Asn | Ala | Leu | Asp | Leu | Lys | Phe | Asp | Met | Glu | Gln | Leu Lys Asp |  |
| 245 |     |     |     |     | 250 |     |     |     |     | 255 |     |     | 260         |  |

| TCT | ATT | GAT | AGG | GAA | AAA | ATA | GCA | GTA | ATT | GGA | CAT | TCT | TTT GGT GGA | 989 |
| Ser | Ile | Asp | Arg | Glu | Lys | Ile | Ala | Val | Ile | Gly | His | Ser | Phe Gly Gly |  |
|     |     |     |     | 265 |     |     |     |     | 270 |     |     |     | 275         |  |

| GCA | ACG | GTT | ATT | CAG | ACT | CTT | AGT | GAA | GAT | CAG | AGA | TTC | AGA TGT GGT | 1037 |
| Ala | Thr | Val | Ile | Gln | Thr | Leu | Ser | Glu | Asp | Gln | Arg | Phe | Arg Cys Gly |  |
|     |     |     | 280 |     |     |     |     | 285 |     |     |     |     | 290         |  |

| ATT | GCC | CTG | GAT | GCA | TGG | ATG | TTT | CCA | CTG | GGT | GAT | GAA | GTA TAT TCC | 1085 |
| Ile | Ala | Leu | Asp | Ala | Trp | Met | Phe | Pro | Leu | Gly | Asp | Glu | Val Tyr Ser |  |
|     |     | 295 |     |     |     |     | 300 |     |     |     |     | 305 |             |  |

| AGA | ATT | CCT | CAG | CCC | CTC | TTT | TTT | ATC | AAC | TCT | GAA | TAT | TTC CAA TAT | 1133 |
| Arg | Ile | Pro | Gln | Pro | Leu | Phe | Phe | Ile | Asn | Ser | Glu | Tyr | Phe Gln Tyr |  |
|     | 310 |     |     |     |     | 315 |     |     |     |     | 320 |     |             |  |

| CCT | GCT | AAT | ATC | ATA | AAA | ATG | AAA | AAA | TGC | TAC | TCA | CCT | GAT AAA GAA | 1181 |
| Pro | Ala | Asn | Ile | Ile | Lys | Met | Lys | Lys | Cys | Tyr | Ser | Pro | Asp Lys Glu |  |
| 325 |     |     |     |     | 330 |     |     |     |     | 335 |     |     | 340         |  |

| AGA | AAG | ATG | ATT | ACA | ATC | AGG | GGT | TCA | GTC | CAC | CAG | AAT | TTT GCT GAC | 1229 |
| Arg | Lys | Met | Ile | Thr | Ile | Arg | Gly | Ser | Val | His | Gln | Asn | Phe Ala Asp |  |

```
                        345                 350                 355
TTC ACT TTT GCA ACT GGC AAA ATA ATT GGA CAC ATG CTC AAA TTA AAG       1277
Phe Thr Phe Ala Thr Gly Lys Ile Ile Gly His Met Leu Lys Leu Lys
                    360                 365                 370

GGA GAC ATA GAT TCA AAT GTA GCT ATT GAT CTT AGC AAC AAA GCT TCA       1325
Gly Asp Ile Asp Ser Asn Val Ala Ile Asp Leu Ser Asn Lys Ala Ser
            375                 380                 385

TTA GCA TTC TTA CAA AAG CAT TTA GGA CTT CAT AAA GAT TTT GAT CAG       1373
Leu Ala Phe Leu Gln Lys His Leu Gly Leu His Lys Asp Phe Asp Gln
        390                 395                 400

TGG GAC TGC TTG ATT GAA GGA GAT GAT GAG AAT CTT ATT CCA GGG ACC       1421
Trp Asp Cys Leu Ile Glu Gly Asp Asp Glu Asn Leu Ile Pro Gly Thr
405                 410                 415                 420

AAC ATT AAC ACA ACC AAT CAA CAC ATC ATG TTA CAG AAC TCT TCA GGA       1469
Asn Ile Asn Thr Thr Asn Gln His Ile Met Leu Gln Asn Ser Ser Gly
                    425                 430                 435

ATA GAG AAA TAC AAT TAGGATTAAA ATAGGTTTTT TAAAAAAAAA AAAAAA           1520
Ile Glu Lys Tyr Asn
                440
```

(2) INFORMATION FOR SEQ ID NO:8:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Pro Pro Lys Leu His Val Leu Phe Cys Leu Cys Gly Cys Leu
  1               5                  10                  15

Ala Val Val Tyr Pro Phe Asp Trp Gln Tyr Ile Asn Pro Val Ala His
                 20                  25                  30

Met Lys Ser Ser Ala Trp Val Asn Lys Ile Gln Val Leu Met Ala Ala
             35                  40                  45

Ala Ser Phe Gly Gln Thr Lys Ile Pro Arg Gly Asn Gly Pro Tyr Ser
         50                  55                  60

Val Gly Cys Thr Asp Leu Met Phe Asp His Thr Asn Lys Gly Thr Phe
 65                  70                  75                  80

Leu Arg Leu Tyr Tyr Pro Ser Gln Asp Asn Asp Arg Leu Asp Thr Leu
                 85                  90                  95

Trp Ile Pro Asn Lys Glu Tyr Phe Trp Gly Leu Ser Lys Phe Leu Gly
                100                 105                 110

Thr His Trp Leu Met Gly Asn Ile Leu Arg Leu Leu Phe Gly Ser Met
            115                 120                 125

Thr Thr Pro Ala Asn Trp Asn Ser Pro Leu Arg Pro Gly Glu Lys Tyr
        130                 135                 140

Pro Leu Val Val Phe Ser His Gly Leu Gly Ala Phe Arg Thr Leu Tyr
145                 150                 155                 160

Ser Ala Ile Gly Ile Asp Leu Ala Ser His Gly Phe Ile Val Ala Ala
                165                 170                 175

Val Glu His Arg Asp Arg Ser Ala Ser Ala Thr Tyr Tyr Phe Lys Asp
            180                 185                 190

Gln Ser Ala Ala Glu Ile Gly Asp Lys Ser Trp Leu Tyr Leu Arg Thr
        195                 200                 205

Leu Lys Gln Glu Glu Glu Thr His Ile Arg Asn Glu Gln Val Arg Gln
    210                 215                 220
```

```
Arg Ala Lys Glu Cys Ser Gln Ala Leu Ser Leu Ile Leu Asp Ile Asp
225                 230                 235                 240

His Gly Lys Pro Val Lys Asn Ala Leu Asp Leu Lys Phe Asp Met Glu
                245                 250                 255

Gln Leu Lys Asp Ser Ile Asp Arg Glu Lys Ile Ala Val Ile Gly His
                260                 265                 270

Ser Phe Gly Gly Ala Thr Val Ile Gln Thr Leu Ser Glu Asp Gln Arg
            275                 280                 285

Phe Arg Cys Gly Ile Ala Leu Asp Ala Trp Met Phe Pro Leu Gly Asp
290                 295                 300

Glu Val Tyr Ser Arg Ile Pro Gln Pro Leu Phe Ile Asn Ser Glu
305                 310                 315                 320

Tyr Phe Gln Tyr Pro Ala Asn Ile Ile Lys Met Lys Lys Cys Tyr Ser
                325                 330                 335

Pro Asp Lys Glu Arg Lys Met Ile Thr Ile Arg Gly Ser Val His Gln
                340                 345                 350

Asn Phe Ala Asp Phe Thr Phe Ala Thr Gly Lys Ile Ile Gly His Met
            355                 360                 365

Leu Lys Leu Lys Gly Asp Ile Asp Ser Asn Val Ala Ile Asp Leu Ser
        370                 375                 380

Asn Lys Ala Ser Leu Ala Phe Leu Gln Lys His Leu Gly Leu His Lys
385                 390                 395                 400

Asp Phe Asp Gln Trp Asp Cys Leu Ile Glu Gly Asp Glu Asn Leu
                405                 410                 415

Ile Pro Gly Thr Asn Ile Asn Thr Thr Asn Gln His Ile Met Leu Gln
                420                 425                 430

Asn Ser Ser Gly Ile Glu Lys Tyr Asn
            435                 440

(2) INFORMATION FOR SEQ ID NO:9:

(i) SEQUENCE CHARACTERISTICS:
        (A) LENGTH: 1123 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: Not Determined (xi) SEQUENCE DESCRIPTION: SEQ ID NO:9:

AAATATAAAT TTTAATAACA CCACACATAA ATTTCAAACT ACTTTCCCTA AGTTTCTAGC     60

TGAAGTTTTA AATGAGTGTG TTTTTAATTT ATTAGAAAGT GGATTGAAGA GAAACATTG    120

GAAGATGAAG GAAGGCGTTT CAGTTAAACC CCAAATAACT CTGTGTTACA CTGAGCTATG   180

AAACGGCTCC TTCTAGCTCC ATTTCTCCTC AGACCTAAGT GCTATTCCTG ATTGTCCTTC   240

ATTGTCATTT CCAGGGAGAA ATGACACCAG CACAGTGGCA GGCCTTCCAA TCTGGAGCAC   300

GGTCCACACA ACTTCCGAAT TGGTGTTCAG TGTAAAGTGT ATCGGAGTGC GGAAAATGCG   360

CAGGGCATTG CCAACTATAG ATGCTCGGAG TAATTCAGTG TATTCAGAGA ACACGGTGAA   420

ACAAGGAAAA CCGGCCTGAC TGGGGGGTGA ATTCAGCAGG GAGTAAATCT GATCGGCATC   480

AGGTCTGCGG AAAGGAGCTG GTGAGCACGA CACCACCAGG CATTGCCTGG CTCTCTCCGC   540

GGCGGGCTAA GTTAACCTCG GTCCAGGTG CGGGCCATGG TCTTGGGGAG GGTGCTGGGT    600

GCGCTCGAGC AGGCTACGTC GGGAGCCGCC GCTGCTAGTG AGAGCCGGGC CACACACGCT   660
```

```
CCTCCCCGGT ACCTCCTCCA GCATCACCAG GGGAGGAGAG GGTCGGGCAC AAGGCGCGCT      720

AGGCGGACCC AGACACAGCC GCGCGCAGCC CACCCGCCCG CCGCCTGCCA GAGCTGCTCG      780

GCCCGCAGCC AGGGGGACAG CGGCTGGTCG GAGGCTCGCA GTGCTGTCGG CGAGAAGCAG      840

TCGGGTTTGG AGCGCTTGGG TCGCGTTGGT GCGCGGTGGA ACCCCCCAGG GACCCCAGTT      900

CCCGCGAGCA GCTCCGCGCC GCGCCTGAGT GAGGAGGGGC CCCGGGGGCG AGGCGGGAGT      960

GGGAGGAAGG GCACGGTCGC CGCGCTGGAG GTCGGGACCC CGGAGCGGCG ACCGGCCGGG     1020

GTGGGCTCGC TGAGTCGCAC CCGCTCTGCT GGCCGGTCCT GGGCTCACAG TCCCTGCAGC     1080

CCTCGGAAAC AGCGCTAGGA TCCTTCGGGA GAGGAGAGAT GAC                       1123

(2) INFORMATION FOR SEQ ID NO:10:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 145..287

(xi) SEQUENCE DESCRIPTION: SEQ ID NO:10:

GTACCAATCT AAAACCCAGC ACAGAAAAAT ACATGTTTTA TTTTTTCCAA GTGTTACTAG       60

TACCTCAGCC TTTCTTGATT TGTCAGCTTA TTTAAGGCCT CTTCATTGCA TACTTCTTTT      120

TTCTTTTAAT CATCTGCTTC GAAGGAGACT AAGCTGAAAC TGCTGCTCAG CTCCCAAGAT      180

GGTGCCACCC AAATTGCATG TGCTTTTCTG CCTCTGCGGC TGCCTGGCTG TGGTTTATCC      240

TTTTGACTGG CAATACATAA ATCCTGTTGC CCATATGAAA TCATCAGGTA AGAGGTGTAT      300

TTGTTCAAGG TCTTGAGCAA CTGATCTGTC GCCATACTTC AAGTGGGCCC CAAGAAGTTG      360

CACATCTGCA CATCTAAACA AGTCCTATTT AAAGGCTTAT GGAGATCCTG TATTCTC         417

(2) INFORMATION FOR SEQ ID NO:11:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 251..372

(xi) SEQUENCE DESCRIPTION: SEQ ID NO:11:

CATTAGGAGG TAACAGTCCA AGGCAGCTGA GAGAAAGGCT ATGTCTACTT TCATCTCTTT       60

ACCCTCCAAA ACCCCTACAC AGTGTTTCAA ACAGAGAGAC CCTCAATAAT TGCATATCTT      120

ACTTGTTAGG TTGAGAAAGA AAGAAGGCCA GAAACTATGG GAAGTAACTT GATTCCGTTG      180

GAATTCTTTT GCATAATAAA ATCTGATATG TAATGGATGA CAAATGAGAT AATATTTACC      240

TGTTTTTCAG CATGGGTCAA CAAAATACAA GTACTGATGG CTGCTGCAAC GTTTGGCCAA      300

ACTAAAATCC CCCGGGGAAA TGGGCCTTAT TCCGTTGGTT GTACAGACTT AATGTTTGAT      360

CACACTAATA AGGTAATGCT TGATTTATA CAACTTATCC TGATACTCTA ATATTGTCTG       420

TCGCTATGGA CCACTAGAAG GTGTTCAAAT GTGACCTTGC CCTCACCTGA GAATGACTCA      480
```

TTTTCGAATT TGTATTGT                                                        498

(2) INFORMATION FOR SEQ ID NO:12:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 130..274

(xi) SEQUENCE DESCRIPTION: SEQ ID NO:12:

CAGCAGCCTA AAGTCTTAGA CTTTGTGAAC ACAGAGGTAT TGAGTCCCAC TAATTAATAT          60

CGAAAATAGC TGCTGGAATA TGTTTGAGAC ACAACTTCTC TAAAAGTGCA TTAATTTCTT         120

TCTTAACAGG GCACCTTCTT GCGTTTATAT TATCCATCCC AAGATAATGA TCACCTTGAC         180

ACCCTTTGGA TCCCAAATAA AGAATATTTT TGGGGTCTTA GCAAATTTCT TGGAACACAC         240

TGGCTTATGG GCAACATTTT GAGGTTACTC TTTGGTAAGA TTTCTGTTGA TCCTTCTTTG         300

TAGGCTCTTG CATGTATGAA AACCTTGAAA ACAACAAGAA CTTCAAGTAG TTAAGACCAA         360

AGTAGATTTT TCTTCAGTCC AAATAGCTCC TAAAATGATA AGGAAAGTAT TTCTTTAAAG         420

CCCAGGCAAC TAC                                                            433

(2) INFORMATION FOR SEQ ID NO:13:

(i) SEQUENCE CHARACTERISTICS:
        (A) LENGTH: 486 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 164..257

(xi) SEQUENCE DESCRIPTION: SEQ ID NO:13:

TTGGTGGGTA TCTAGTAGCA GTCTTTTTAA TGAATCTACT ATTCATCCAT AAAAAAGTAG          60

ATATAAATCA GATGGGTCTG CATTTTATGC TAATGAGATA TGAATTAAAT TCACTAGCAA         120

CACTCAGAGA AAACCTTAAC TATAACCTTC CATTGTTGTC TAGGTTCAAT GACAACTCCT         180

GCAAACTGGA ATTCCCCTCT GAGGCCTGGT GAAAAATATC CACTTGTTGT TTTTTCTCAT         240

GGTCTTGGGG CATTCAGGTA ATGTTTGAGA GGTTGAACAA TTTTGGCTTC CAGGAATAAA         300

TGACAATTTT TTTATTCAAG AAAGAAATAG CAGAGTTTGG AATGTCATGC AGGCCCTTGT         360

CTGGAGGAGT TGGGGTTCCT CAATAATTGG CTGTGGGTCT ATTGATCAGT CCTAGACCTG         420

TCTGGTCAAG TAGTTTTTTC CCTACTATCA GCTCATTGGG ATTAGCCTCA CAGCAGAGAA         480

GAAAGG                                                                    486

(2) INFORMATION FOR SEQ ID NO:14:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (genomic)

(ix) FEATURE:
            (A) NAME/KEY: exon
            (B) LOCATION: 113..181

(xi) SEQUENCE DESCRIPTION: SEQ ID NO:14:

| | | | | | |
|---|---|---|---|---|---|
| CCCCAGGCTC | TACTACAGGG | TGTAATGGCC | TCCATGTTCC | CAGTTTTATT | AGTGACTCAG | 60 |
| CCTTGTAATT | CATGACTGGT | AGTTGTAATT | CTTCCCTCTT | TTTGTTTTGA | AGGACACTTT | 120 |
| ATTCTGCTAT | TGGCATTGAC | CTGGCATCTC | ATGGGTTTAT | AGTTGCTGCT | GTAGAACACA | 180 |
| GGTATGTTAC | CTGATATAAT | TGGGCTCTTT | GGCCAACTAC | AGGGAATGTC | AATGCTCATA | 240 |
| ACTATGTTTC | TAATTTTCAT | AAAAGTTTAT | TTAAAATGTT | GATGGAACTT | TCAAGTATGG | 300 |
| TAACATCATG | AGCAAAAAAG | GAGATTGAGT | TTTATCGACT | TAAAAGACTT | AAAAGCACCT | 360 |
| AAC | | | | | | 363 |

(2) INFORMATION FOR SEQ ID NO:15:

(i) SEQUENCE CHARACTERISTICS:
            (A) LENGTH: 441 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: exon
            (B) LOCATION: 68..191

(xi) SEQUENCE DESCRIPTION: SEQ ID NO:15:

| | | | | | |
|---|---|---|---|---|---|
| GAACTGAGAA | ACATGGTCAG | ATGAGGAAGG | GAAGGAGCAT | GCATAAATAA | TTTTGCTTGT | 60 |
| ATTATAGAGA | TAGATCTGCA | TCTGCAACTT | ACTATTTCAA | GGACCAATCT | GCTGCAGAAA | 120 |
| TAGGGGACAA | GTCTTGGCTC | TACCTTAGAA | CCCTGAAACA | AGAGGAGGAG | ACACATATAC | 180 |
| GAAATGAGCA | GGTACATTGC | AGTGAAAGGA | GAGGTGGTTG | GTGACCTAAA | AGCATGTACA | 240 |
| AAAGGATGAC | ATTTGTTAAT | TTAATTTTAC | ACCTGGCAAG | TTATGCTCCT | AGCTCTCCTA | 300 |
| TTTCCCATTC | CCAAAAGATC | TGTCAATAGA | TTCCTGGAGC | AGTAAAATTC | CCTTAATGGA | 360 |
| ATATCTAGTT | CATAGTAAAA | ACAAAGGCAA | ATACAAAAAT | TTGGGAGATG | ACAGTGAATA | 420 |
| TTCAGAATTC | CTCGAGCCGG | G | | | | 441 |

(2) INFORMATION FOR SEQ ID NO:16:

(i) SEQUENCE CHARACTERISTICS:
            (A) LENGTH: 577 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: exon
            (B) LOCATION: 245..358

(xi) SEQUENCE DESCRIPTION: SEQ ID NO:16:

| | | | | | |
|---|---|---|---|---|---|
| GGTTAAGTAA | ATCGTCTGAA | GTCACATAGT | AGGTAAGGCA | AAACAGAGCC | AGGATTTGGA | 60 |
| CTAAGGCTAT | ACCTATGTGC | AAAGCTGGGG | CCTGTGTCAT | TATGGTAGCA | AGTAATAGTC | 120 |
| ACTAATCAGA | TTTCCAGTTT | ATAACTGACC | AACGATTTTT | CCCAAATACA | GCTTCTACCT | 180 |
| AAACTTTAAA | ATAAGTGTTA | TAACTTTTTA | CTTTGTCATT | TCCTTCTTCT | AATAATTATA | 240 |

| | |
|---|---|
| TTAGGTACGG CAAAGAGCAA AAGAATGTTC CCAAGCTCTC AGTCTGATTC TTGACATTGA | 300 |
| TCATGGAAAG CCAGTGAAGA ATGCATTAGA TTTAAAGTTT GATATGGAAC AACTGAAGGT | 360 |
| AAGCTATAAA AAGTAATTTT TCTCTTGTCC TACAGTTCTT TATTGTTTTT TGTCATTTAA | 420 |
| TTTTCTGCCT ATATTGCAAG GTACAATATG ATAAAGGGCT GCAACCAGCC CCTCCCCAAT | 480 |
| GCGCACACAC AGACACACAA AGCAGTACAG GTAAAGTATT GCAGCAATGA AGAATGCATT | 540 |
| ATCTTGGACT AGATATGAAT GCAAAGTTAG TCAGTTT | 577 |

(2) INFORMATION FOR SEQ ID NO:17:

(i) SEQUENCE CHARACTERISTICS:
  (A) LENGTH: 396 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: exon
  (B) LOCATION: 108..199

(xi) SEQUENCE DESCRIPTION: SEQ ID NO:17:

| | |
|---|---|
| ATCAATGTAT TTACCATCCC CATGAAATGA ACAATTATAT GATTGACAAA TCATTTCTTC | 60 |
| TAACACCACG AAATAGCTAT AAATTTATAT CATGCTTTTT CAAATAGGAC TCTATTGATA | 120 |
| GGGAAAAAAT AGCAGTAATT GGACATTCTT TTGGTGGAGC AACGGTTATT CAGACTCTTA | 180 |
| GTGAAGATCA GAGATTCAGG TAAGAAAATA AGATAGTAAA GCAAGAGAAT AGTAAATTAT | 240 |
| TGGAAGAAAT TATATTGTGA GATATAATTT TTATTCAAAT TCTTAGTGAA GGAAGGGGAT | 300 |
| CTCTTGGAGT TTATAAGGCT ATTCTTTTGC CCCCATAAAA TACTCTATAT ACATTTTCCT | 360 |
| AGGCTAAAAC ATCCCTCTC CTGCTATTAA AATCTC | 396 |

(2) INFORMATION FOR SEQ ID NO:18:

(i) SEQUENCE CHARACTERISTICS:
  (A) LENGTH: 519 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: exon
  (B) LOCATION: 181..351

(xi) SEQUENCE DESCRIPTION: SEQ ID NO:18:

| | |
|---|---|
| CTTACAAAGT TAATCATATC CCTTTCCCAC ATTGAAGTAT GATACCTCTT TATTCCAATC | 60 |
| AGATAACCCA TAATAAACTG GTATGGTGCG TGTCCACCAA TCCTAGCATT ATTAGGATGT | 120 |
| CCTCAATGTT GGCTAGTATG TAACCAGTTT AATTTCATCA TTGTCAACAA ATATCTACAG | 180 |
| ATGTGGTATT GCCCTGGATG CATGGATGTT TCCACTGGGT GATGAAGTAT ATTCCAGAAT | 240 |
| TCCTCAGCCC CTCTTTTTTA TCAACTCTGA ATATTTCCAA TATCCTGCTA ATATCATAAA | 300 |
| AATGAAAAAA TGCTACTCAC CTGATAAAGA AAGAAAGATG ATTACAATCA GGTAAGTATT | 360 |
| AGTGACTTAT TTCATTATGT GAAACAAACT TGAAGCTTGG GTAAATATCA ATCGATATCA | 420 |
| TTTGGTAACT ATTAAAGAAT TGCTGAATTG GTTGTTTAGA CTTTCAATAA GGAGAGAATT | 480 |
| AGATAATCTC AGTTTCTAAG TACATTTAGT CTACTCTTT | 519 |

(2) INFORMATION FOR SEQ ID NO:19:

(i) SEQUENCE CHARACTERISTICS:
               (A) LENGTH: 569 base pairs
               (B) TYPE: nucleic acid
               (C) STRANDEDNESS: single
               (D) TOPOLOGY: linear (ii) MOLECULE TYPE: DNA (genomic)

(ix) FEATURE:
               (A) NAME/KEY: exon
               (B) LOCATION: 156..304

(xi) SEQUENCE DESCRIPTION: SEQ ID NO:19:

TGAAACACAT CTAAGTAGAT CAAATTACAA GTTTTATTTC TTCTTTGGTT TTCAGTAAAC      60

AGACCAACAA GACCAGTACC TTTCCTTACA CTCTAACTAA AAAAATAATA ATTTTATCAA     120

ACAATGTGAC TTTTAAATGT CTTGTTCTCT TTTAGGGGTT CAGTCCACCA GAATTTTGCT     180

GACTTCACTT TTGCAACTGG CAAAATAATT GGACACATGC TCAAATTAAA GGGAGACATA     240

GATTCAAATG TAGCTATTGA TCTTAGCAAC AAAGCTTCAT TAGCATTCTT ACAAAAGCAT     300

TTAGGTAAGA AACTATTTTT TTCATGACCT AAACCGAGAT GAATCTCGAG GACAAAGCTG     360

TCTATCTTAA TACAGCTTTA GTACTATTTA AACTATTTCC AGTTGGTTTA CAATGGAACA     420

AAGCAGTATA TCAATTTGAA AACAGAAATT TGAGAAAGTC AATTTTGCTG CTTTACATCT     480

CTATATCATA GAAAGCAAAT CAACTGTTAA AGGTAATATT CTTTGTATGA GCTAGAGTGA     540

CTCATGTGAG GATATCGAAC GACGGTGCT                                       569

(2) INFORMATION FOR SEQ ID NO:20:

(i) SEQUENCE CHARACTERISTICS:
               (A) LENGTH: 469 base pairs
               (B) TYPE: nucleic acid
               (C) STRANDEDNESS: single
               (D) TOPOLOGY: linear (ii) MOLECULE TYPE: DNA (genomic)

(ix) FEATURE:
               (A) NAME/KEY: exon
               (B) LOCATION: 137..253

(xi) SEQUENCE DESCRIPTION: SEQ ID NO:20:

GATACAGAGG CACATCGTCT CTACCATCCT AACGGAACTT GTGTAATTTG TAAATCTTTA      60

TTGCCACCTA GGGGCATCCA AACTGTTTAA TGCTCTCAAA AGTTTAATAT GTTGATTAAC     120

ACTTTATATT TTATAGGACT TCATAAAGAT TTTGATCAGT GGGACTGCTT GATTGAAGGA     180

GATGATGAGA ATCTTATTCC AGGGACCAAC ATTAACACAA CCAATCAACA CATCATGTTA     240

CAGAACTCTT CAGGAATAGA GAAATACAAT TAGGATTAAA ATAGGTTTTT TAAAAGTCTT     300

GTTTCAAAAC TGTCTAAAAT TATGTGTGTG TGTGTGTGTG TGTGTGTGTG AGAGAGAGAG     360

AGAGAGAGAG AGAGAGAATT TTAATGTATT TTCCCAAAGG ACTCATATTT TAAAATGTAG     420

GCTATACTGT AATCGTGATT GAAGCTTGGA CTAAGAATTT TTTCCCTTT                 469

(2) INFORMATION FOR SEQ ID NO:21:

(i) SEQUENCE CHARACTERISTICS:
               (A) LENGTH: 1494 base pairs
               (B) TYPE: nucleic acid
               (C) STRANDEDNESS: single
               (D) TOPOLOGY: linear (ii) MOLECULE TYPE: cDNA (ix) FEATURE:

-continued (A) NAME/KEY: CDS
    (B) LOCATION: 117..1436

(xi) SEQUENCE DESCRIPTION: SEQ ID NO:21:

```
GGCACGAGCT AGGATCTGAC TCGCTCTGGT GGCATTGCTG CGCTCAGGGT TCTGGGTATC        60

CGGGAGTCAG TGCAGTGACC AGAACATCAA ACTGAAGCCA CTGCTCAGCT CCTAAG           116

ATG GTA CCA CTC AAA CTG CAG GCG CTT TTC TGC CTC CTC TGC TGC CTC        164
Met Val Pro Leu Lys Leu Gln Ala Leu Phe Cys Leu Leu Cys Cys Leu
 1               5                  10                  15

CCA TGG GTC CAT CCT TTT CAC TGG CAA GAC ACA TCT TCT TTT GAC TTC        212
Pro Trp Val His Pro Phe His Trp Gln Asp Thr Ser Ser Phe Asp Phe
             20                  25                  30

AGG CCG TCA GTA ATG TTT CAC AAG CTC CAA TCG GTG ATG TCT GCT GCC        260
Arg Pro Ser Val Met Phe His Lys Leu Gln Ser Val Met Ser Ala Ala
         35                  40                  45

GGC TCT GGC CAT AGT AAA ATC CCC AAA GGA AAT GGA TCG TAC CCC GTC        308
Gly Ser Gly His Ser Lys Ile Pro Lys Gly Asn Gly Ser Tyr Pro Val
     50                  55                  60

GGT TGT ACA GAT CTG ATG TTC GGT TAT GGG AAT GAG AGC GTC TTC GTG        356
Gly Cys Thr Asp Leu Met Phe Gly Tyr Gly Asn Glu Ser Val Phe Val
 65                  70                  75                  80

CGT TTG TAC TAC CCA GCT CAA GAT CAA GGT CGC CTC GAC ACT GTT TGG        404
Arg Leu Tyr Tyr Pro Ala Gln Asp Gln Gly Arg Leu Asp Thr Val Trp
                 85                  90                  95

ATC CCA AAC AAA GAA TAT TTT TTG GGT CTT AGT ATA TTT CTT GGA ACA        452
Ile Pro Asn Lys Glu Tyr Phe Leu Gly Leu Ser Ile Phe Leu Gly Thr
            100                 105                 110

CCC AGT ATT GTA GGC AAT ATT TTA CAC CTC TTA TAT GGT TCT CTG ACA        500
Pro Ser Ile Val Gly Asn Ile Leu His Leu Leu Tyr Gly Ser Leu Thr
        115                 120                 125

ACT CCT GCA AGC TGG AAT TCT CCT TTA AGG ACT GGA GAA AAA TAC CCG        548
Thr Pro Ala Ser Trp Asn Ser Pro Leu Arg Thr Gly Glu Lys Tyr Pro
    130                 135                 140

CTC ATT GTC TTT TCT CAT GGT CTC GGA GCC TTC AGG ACG ATT TAT TCT        596
Leu Ile Val Phe Ser His Gly Leu Gly Ala Phe Arg Thr Ile Tyr Ser
145                 150                 155                 160

GCT ATT GGC ATT GGC TTG GCA TCT AAT GGG TTT ATA GTG GCC ACT GTC        644
Ala Ile Gly Ile Gly Leu Ala Ser Asn Gly Phe Ile Val Ala Thr Val
                165                 170                 175

GAA CAC AGA GAC AGA TCT GCA TCG GCA ACT TAC TTT TTT GAA GAC CAG        692
Glu His Arg Asp Arg Ser Ala Ser Ala Thr Tyr Phe Phe Glu Asp Gln
            180                 185                 190

GTG GCT GCA AAA GTG GAA AAC AGG TCT TGG CTT TAC CTG AGA AAA GTA        740
Val Ala Ala Lys Val Glu Asn Arg Ser Trp Leu Tyr Leu Arg Lys Val
        195                 200                 205

AAA CAA GAG GAG TCG GAA AGT GTC CGG AAA GAA CAG GTT CAG CAA AGA        788
Lys Gln Glu Glu Ser Glu Ser Val Arg Lys Glu Gln Val Gln Gln Arg
    210                 215                 220

GCA ATA GAA TGT TCC CGG GCT CTC AGT GCG ATT CTT GAC ATT GAA CAT        836
Ala Ile Glu Cys Ser Arg Ala Leu Ser Ala Ile Leu Asp Ile Glu His
225                 230                 235                 240

GGA GAC CCA AAA GAG AAT GTA CTA GGT TCA GCT TTT GAC ATG AAA CAG        884
Gly Asp Pro Lys Glu Asn Val Leu Gly Ser Ala Phe Asp Met Lys Gln
                245                 250                 255

CTG AAG GAT GCT ATT GAT GAG ACT AAA ATA GCT TTG ATG GGA CAT TCT        932
Leu Lys Asp Ala Ile Asp Glu Thr Lys Ile Ala Leu Met Gly His Ser
            260                 265                 270

TTT GGA GGA GCA ACA GTT CTT CAA GCC CTT AGT GAG GAC CAG AGA TTC        980
Phe Gly Gly Ala Thr Val Leu Gln Ala Leu Ser Glu Asp Gln Arg Phe
        275                 280                 285
```

```
AGA TGT GGA GTT GCT CTT GAT CCA TGG ATG TAT CCG GTG AAC GAA GAG       1028
Arg Cys Gly Val Ala Leu Asp Pro Trp Met Tyr Pro Val Asn Glu Glu
    290                 295                 300

CTG TAC TCC AGA ACC CTC CAG CCT CTC CTC TTT ATC AAC TCT GCC AAA       1076
Leu Tyr Ser Arg Thr Leu Gln Pro Leu Leu Phe Ile Asn Ser Ala Lys
305                 310                 315                 320

TTC CAG ACT CCA AAG GAC ATC GCA AAA ATG AAA AAG TTC TAC CAG CCT       1124
Phe Gln Thr Pro Lys Asp Ile Ala Lys Met Lys Lys Phe Tyr Gln Pro
                325                 330                 335

GAC AAG GAA AGG AAA AAT GAT TAC AAT CAA GGG CTC AGG CAC CAG AAC       1172
Asp Lys Glu Arg Lys Asn Asp Tyr Asn Gln Gly Leu Arg His Gln Asn
            340                 345                 350

TTT GAC GAC TTT ACT TTT GTA ACT GGC AAA ATA ATT GGA AAC AAG CTG       1220
Phe Asp Asp Phe Thr Phe Val Thr Gly Lys Ile Ile Gly Asn Lys Leu
        355                 360                 365

ACA CTG AAA GGA GAA ATC GAT TCC AGA GTA GCC ATC GAC CTC ACC AAC       1268
Thr Leu Lys Gly Glu Ile Asp Ser Arg Val Ala Ile Asp Leu Thr Asn
    370                 375                 380

AAA GCT TCG ATG GCT TTC TTA CAA AAG CAT TTA GGG CTT CAG AAA GAC       1316
Lys Ala Ser Met Ala Phe Leu Gln Lys His Leu Gly Leu Gln Lys Asp
385                 390                 395                 400

TTT GAT CAG TGG GAC CCT CTG GTG GAA GGA GAT GAT GAG AAC CTG ATT       1364
Phe Asp Gln Trp Asp Pro Leu Val Glu Gly Asp Asp Glu Asn Leu Ile
                405                 410                 415

CCT GGG TCA CCC TTT GAC GCA GTC ACC CAG GCC CCG GCT CAG CAA CAC       1412
Pro Gly Ser Pro Phe Asp Ala Val Thr Gln Ala Pro Ala Gln Gln His
            420                 425                 430

TCT CCA GGA TCA CAG ACC CAG AAT TAGAAGAACT TGCTTGTTAC ACAGTTGCCT      1466
Ser Pro Gly Ser Gln Thr Gln Asn
            435                 440

TTTAAAAGTA GAGTGACATG AGAGAGAG                                        1494

(2) INFORMATION FOR SEQ ID NO:22:

(i) SEQUENCE CHARACTERISTICS:
         (A) LENGTH: 2191 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 92..1423

(xi) SEQUENCE DESCRIPTION: SEQ ID NO:22:

CCGCGCGCTC CGGCCGGGGG ACCCTGGTTC CGGCGAGCGG CTCAGCGCGG CGCCCGGAAG       60

TTTAAGCTGA AACCACTGCT CAGCTTCCAA G ATG TTG CCA CCC AAA CTG CAT         112
                                   Met Leu Pro Pro Lys Leu His
                                   1               5

GCG CTT TTC TGC CTC TGC AGC TGC CTC ACA CTG GTT CAT CCT ATT GAC        160
Ala Leu Phe Cys Leu Cys Ser Cys Leu Thr Leu Val His Pro Ile Asp
        10                  15                  20

TGG CAA GAC CTA AAT CCT GTT GCC CAT ATT AGA TCA TCA GCA TGG GCC        208
Trp Gln Asp Leu Asn Pro Val Ala His Ile Arg Ser Ser Ala Trp Ala
    25                  30                  35

AAT AAA ATA CAA GCT CTG ATG GCT GCT GCA AGT ATT AGG CAA AGT AGA        256
Asn Lys Ile Gln Ala Leu Met Ala Ala Ala Ser Ile Arg Gln Ser Arg
40                  45                  50                  55

ATT CCC AAA GGA AAT GGA TCT TAT TCT GTC GGT TGT ACA GAT TTG ATG        304
Ile Pro Lys Gly Asn Gly Ser Tyr Ser Val Gly Cys Thr Asp Leu Met
```

```
                   60                    65                    70
TTT GAT TAT ACT AAT AAG GGC ACC TTT TTG CGT TTG TAT TAT CCA TCG      352
Phe Asp Tyr Thr Asn Lys Gly Thr Phe Leu Arg Leu Tyr Tyr Pro Ser
                75                    80                    85

CAA GAG GAT GAC CAC TCT GAC ACG CTT TGG ATC CCA AAC AAA GAA TAT      400
Gln Glu Asp Asp His Ser Asp Thr Leu Trp Ile Pro Asn Lys Glu Tyr
            90                    95                   100

TTT TTT GGT CTT AGT AAA TAT CTT GGA ACA CCC TGG CTT ATG GGC AAA      448
Phe Phe Gly Leu Ser Lys Tyr Leu Gly Thr Pro Trp Leu Met Gly Lys
        105                   110                   115

ATA TTG AGC TTC TTT TTT GGT TCA GTG ACA ACT CCT GCG AAC TGG AAT      496
Ile Leu Ser Phe Phe Phe Gly Ser Val Thr Thr Pro Ala Asn Trp Asn
120                   125                   130                   135

TCC CCT CTG AGG ACT GGT GAA AAA TAT CCA CTG ATT GTT TTT TCT CAT      544
Ser Pro Leu Arg Thr Gly Glu Lys Tyr Pro Leu Ile Val Phe Ser His
            140                   145                   150

GGT CTT GGA GCA TTC CGG ACA ATT TAT TCT GCT ATT GGC ATT GAT CTA      592
Gly Leu Gly Ala Phe Arg Thr Ile Tyr Ser Ala Ile Gly Ile Asp Leu
        155                   160                   165

GCA TCA CAT GGG TTC ATC GTT GCT GCT ATA GAA CAC AGA GAT GGA TCC      640
Ala Ser His Gly Phe Ile Val Ala Ala Ile Glu His Arg Asp Gly Ser
        170                   175                   180

GCC TCT GCG ACT TAC TAT TTC AAG GAC CAG TCT GCT GCA GAA ATA GGG      688
Ala Ser Ala Thr Tyr Tyr Phe Lys Asp Gln Ser Ala Ala Glu Ile Gly
185                   190                   195

AAC AAA TCT TGG TCT TAT CTT CAA GAA CTA AAA CCA GGG GAT GAG GAG      736
Asn Lys Ser Trp Ser Tyr Leu Gln Glu Leu Lys Pro Gly Asp Glu Glu
200                   205                   210                   215

ATA CAT GTT CGA AAT GAG CAG GTA CAG AAA AGG GCA AAG GAG TGC TCC      784
Ile His Val Arg Asn Glu Gln Val Gln Lys Arg Ala Lys Glu Cys Ser
            220                   225                   230

CAA GCT CTC AAC TTG ATT CTG GAC ATT GAT CAT GGA AGG CCA ATT AAG      832
Gln Ala Leu Asn Leu Ile Leu Asp Ile Asp His Gly Arg Pro Ile Lys
        235                   240                   245

AAT GTA CTA GAC TTA GAG TTT GAT GTG GAA CAA CTG AAG GAC TCT ATT      880
Asn Val Leu Asp Leu Glu Phe Asp Val Glu Gln Leu Lys Asp Ser Ile
        250                   255                   260

GAC AGG GAT AAA ATA GCA GTA ATT GGA CAT TCT TTT GGT GGA GCC ACA      928
Asp Arg Asp Lys Ile Ala Val Ile Gly His Ser Phe Gly Gly Ala Thr
265                   270                   275

GTT CTT CAG GCT CTT AGT GAA GAC CAG AGA TTT AGG TGC GGG ATT GCC      976
Val Leu Gln Ala Leu Ser Glu Asp Gln Arg Phe Arg Cys Gly Ile Ala
280                   285                   290                   295

TTG GAT GCA TGG ATG CTT CCA CTG GAT GAT GCA ATA TAT TCC AGA ATC     1024
Leu Asp Ala Trp Met Leu Pro Leu Asp Asp Ala Ile Tyr Ser Arg Ile
            300                   305                   310

CCT CAG CCC CTC TTT TTT ATT AAC TCG GAA CGG TTC CAA TTT CCT GAG     1072
Pro Gln Pro Leu Phe Phe Ile Asn Ser Glu Arg Phe Gln Phe Pro Glu
        315                   320                   325

AAT ATC AAA AAA ATG AAA AAA TGC TAC TCA CCT GAC AAA GAA AGA AAA     1120
Asn Ile Lys Lys Met Lys Lys Cys Tyr Ser Pro Asp Lys Glu Arg Lys
        330                   335                   340

ATG ATT ACA ATC AGG GGT TCA GTC CAT CAG AAC TTT GCT GAT TTC ACT     1168
Met Ile Thr Ile Arg Gly Ser Val His Gln Asn Phe Ala Asp Phe Thr
345                   350                   355

TTT ACA ACT GGC AAA ATA GTT GGA TAC ATA TTC ACA TTA AAA GGA GAT     1216
Phe Thr Thr Gly Lys Ile Val Gly Tyr Ile Phe Thr Leu Lys Gly Asp
360                   365                   370                   375

ATA GAT TCA AAT GTA GCA ATT GAT CTT TGC AAC AAA GCT TCA TTG GCA     1264
Ile Asp Ser Asn Val Ala Ile Asp Leu Cys Asn Lys Ala Ser Leu Ala
```

-continued

```
              380                 385                 390
TTT TTA CAA AAG CAT TTA GGA CTG CGG AAA GAT TTT GAT CAG TGG GAT          1312
Phe Leu Gln Lys His Leu Gly Leu Arg Lys Asp Phe Asp Gln Trp Asp
            395                 400                 405

TCT TTG ATT GAA GGA AAA GAC GAA AAT CTT ATG CCA GGG ACC AAC ATT          1360
Ser Leu Ile Glu Gly Lys Asp Glu Asn Leu Met Pro Gly Thr Asn Ile
            410                 415                 420

AAC ATC ACC AAC GAA CAT GAC ACT CTA CAG AAC TCT CCA GAA GCA GAG          1408
Asn Ile Thr Asn Glu His Asp Thr Leu Gln Asn Ser Pro Glu Ala Glu
            425                 430                 435

AAA TCG AAT TTA GAT TAAAAGCACT TTTTTAAAGA TCTTGTTTAA AAACTGTCAA          1463
Lys Ser Asn Leu Asp
440

AAAATGTGTG TATGACTTTT AATATATTTT CTCAAATAAC TCATATTGGA AAATGTAGGC        1523

TATCCCATAA AAGTGATTGA AGCTTGGACT AGGAGGTTTT TTTCTTTAAA GAAAGATTGG        1583

TGTCTATCGA AATCATGCCA GCCTAAATTT TAATTTTACT AAAATGATGC TGTGTCAAAA        1643

TTAATAACTA CTTTTACATT CTTTAATGGA CAAGTATAAC AGGCACAAGG CTAATGAAAA        1703

CGTGTTGCAA TGACATAACA ATCCCTAAAA ATACAGATGT TCTTGCCTCT TTTTTCTATT        1763

ATAATTGAGT TTTAGCAACA TGTTATGCTA GGTAGAATTT GGAAGCACTT CCCTTTGACT        1823

TTTGGTCATG ATAAGAAAAA TTAGATCAAG CAAATGATAA AAGCAGTGTT TTACCAAGGA        1883

TTAGGGATAC TGAACAATTT CACTATGGTA ACTGAATGGG GAGTGACCAA GGGTAAAAAT        1943

ATTAAAGCCA AGGCAAAGGC AGCAGATTAG AATGGATTAA AGAGAGTTTA TAATTTGTTT        2003

GCATTTACTT GATGGTTTAT CTCATGGATT CATGAGTCAA GAAAGGTGCG TAGGACAGGC        2063

CAGGGATTCC AGTTATAACA CATTATTCAC CCAAAGGGTT CTTTAATTCT GTATGAGTAT        2123

TGGGAGTGGA TTAGCACAAT AGAGGCATAT GTTGCTTTAA AAAAAAAAAA AAAAAAAAA        2183

AAAAAAAA                                                                 2191

(2) INFORMATION FOR SEQ ID NO:23:

(i) SEQUENCE CHARACTERISTICS:
         (A) LENGTH: 1533 base pairs
         (B) TYPE: nucleic acid
         (C) STRANDEDNESS: single
         (D) TOPOLOGY: linear (ii) MOLECULE TYPE: protein (ix) FEATURE:
         (A) NAME/KEY: CDS
         (B) LOCATION: 62..1394

(xi) SEQUENCE DESCRIPTION: SEQ ID NO:23:

CCGCGAGCAG TTCACCGCGG CGTCCGGAAG GTTAAGCTGA ACGGCAGCT CAGCTTCGGA           60

G ATG TTA CCG TCC AAA TTG CAT GCG CTT TTC TGC CTC TGC ACC TGC            106
  Met Leu Pro Ser Lys Leu His Ala Leu Phe Cys Leu Cys Thr Cys
  1               5                  10                  15

CTT GCA CTG GTT TAT CCT TTT GAC TGG CAA GAC CTG AAT CCA GTT GCC          154
Leu Ala Leu Val Tyr Pro Phe Asp Trp Gln Asp Leu Asn Pro Val Ala
             20                  25                  30

TAT ATT GAA TCA CCA GCA TGG GTC AGT AAG ATA CAA GCT CTG ATG GCT          202
Tyr Ile Glu Ser Pro Ala Trp Val Ser Lys Ile Gln Ala Leu Met Ala
            35                  40                  45

GCT GCA AAC ATT GGT CAA TCT AAA ATC CCC AGA GGA AAT GGA TCT TAT          250
Ala Ala Asn Ile Gly Gln Ser Lys Ile Pro Arg Gly Asn Gly Ser Tyr
        50                  55                  60

TCC GTC GGT TGT ACA GAC TTG ATG TTT GAT TAC ACT AAT AAG GGC ACC          298
```

-continued

| | | | | | | | | | | | | | | | |
|---|---|---|---|---|---|---|---|---|---|---|---|---|---|---|---|
| | Ser | Val | Gly | Cys | Thr | Asp | Leu | Met | Phe | Asp | Tyr | Thr | Asn | Lys | Gly | Thr |
| | | 65 | | | | 70 | | | | | 75 | | | | | |

| TTC | TTG | CGT | TTG | TAT | TAT | CCA | TCT | CAA | GAT | GAT | GAT | CAC | TCC | GAC | ACC | 346 |
|---|---|---|---|---|---|---|---|---|---|---|---|---|---|---|---|---|
| Phe | Leu | Arg | Leu | Tyr | Tyr | Pro | Ser | Gln | Asp | Asp | Asp | His | Ser | Asp | Thr | |
| 80 | | | | | 85 | | | | | 90 | | | | | 95 | |

| CTT | TGG | ATC | CCA | AAC | AAA | GAA | TAT | TTT | TTG | GGT | CTT | AGT | AAA | TTT | CTT | 394 |
|---|---|---|---|---|---|---|---|---|---|---|---|---|---|---|---|---|
| Leu | Trp | Ile | Pro | Asn | Lys | Glu | Tyr | Phe | Leu | Gly | Leu | Ser | Lys | Phe | Leu | |
| | | | | 100 | | | | | 105 | | | | | 110 | | |

| GGA | ACA | CAC | TGG | CTT | GTG | GGC | AAA | ATT | ATG | GGC | TTA | TTC | TTC | GGT | TCA | 442 |
|---|---|---|---|---|---|---|---|---|---|---|---|---|---|---|---|---|
| Gly | Thr | His | Trp | Leu | Val | Gly | Lys | Ile | Met | Gly | Leu | Phe | Phe | Gly | Ser | |
| | | | | 115 | | | | | 120 | | | | | 125 | | |

| ATG | ACA | ACT | CCT | GCA | GCC | TGG | AAT | GCA | CAT | CTG | AGG | ACT | GGG | GAA | AAA | 490 |
|---|---|---|---|---|---|---|---|---|---|---|---|---|---|---|---|---|
| Met | Thr | Thr | Pro | Ala | Ala | Trp | Asn | Ala | His | Leu | Arg | Thr | Gly | Glu | Lys | |
| | | 130 | | | | | 135 | | | | | 140 | | | | |

| TAC | CCA | CTA | ATT | ATT | TTT | TCT | CAT | GGT | CTT | GGA | GCA | TTC | AGG | ACG | ATT | 538 |
|---|---|---|---|---|---|---|---|---|---|---|---|---|---|---|---|---|
| Tyr | Pro | Leu | Ile | Ile | Phe | Ser | His | Gly | Leu | Gly | Ala | Phe | Arg | Thr | Ile | |
| 145 | | | | | 150 | | | | | 155 | | | | | | |

| TAT | TCT | GCT | ATT | GGC | ATT | GAT | CTG | GCA | TCC | CAC | GGG | TTT | ATA | GTT | GCT | 586 |
|---|---|---|---|---|---|---|---|---|---|---|---|---|---|---|---|---|
| Tyr | Ser | Ala | Ile | Gly | Ile | Asp | Leu | Ala | Ser | His | Gly | Phe | Ile | Val | Ala | |
| 160 | | | | | 165 | | | | | 170 | | | | | 175 | |

| GCT | GTA | GAA | CAC | AGG | GAT | GGC | TCT | GCA | TCC | TCG | ACA | TAC | TAT | TTC | AAG | 634 |
|---|---|---|---|---|---|---|---|---|---|---|---|---|---|---|---|---|
| Ala | Val | Glu | His | Arg | Asp | Gly | Ser | Ala | Ser | Ser | Thr | Tyr | Tyr | Phe | Lys | |
| | | | | 180 | | | | | 185 | | | | | 190 | | |

| GAC | CAG | TCT | GCT | GTA | GAA | ATA | GGC | AAC | AAG | TCT | TGG | CTC | TAT | CTC | AGA | 682 |
|---|---|---|---|---|---|---|---|---|---|---|---|---|---|---|---|---|
| Asp | Gln | Ser | Ala | Val | Glu | Ile | Gly | Asn | Lys | Ser | Trp | Leu | Tyr | Leu | Arg | |
| | | | 195 | | | | | 200 | | | | | 205 | | | |

| ACC | CTG | AAG | CGA | GGA | GAG | GAG | GAG | TTT | CCT | TTA | CGA | AAT | GAG | CAG | TTA | 730 |
|---|---|---|---|---|---|---|---|---|---|---|---|---|---|---|---|---|
| Thr | Leu | Lys | Arg | Gly | Glu | Glu | Glu | Phe | Pro | Leu | Arg | Asn | Glu | Gln | Leu | |
| | | 210 | | | | | 215 | | | | | 220 | | | | |

| CGG | CAA | CGA | GCA | AAG | GAA | TGT | TCT | CAA | GCT | CTC | AGT | TTG | ATT | CTG | GAC | 778 |
|---|---|---|---|---|---|---|---|---|---|---|---|---|---|---|---|---|
| Arg | Gln | Arg | Ala | Lys | Glu | Cys | Ser | Gln | Ala | Leu | Ser | Leu | Ile | Leu | Asp | |
| 225 | | | | | 230 | | | | | 235 | | | | | | |

| ATT | GAT | CAC | GGG | AGG | CCA | GTG | ACG | AAT | GTA | CTA | GAT | TTA | GAG | TTT | GAT | 826 |
|---|---|---|---|---|---|---|---|---|---|---|---|---|---|---|---|---|
| Ile | Asp | His | Gly | Arg | Pro | Val | Thr | Asn | Val | Leu | Asp | Leu | Glu | Phe | Asp | |
| 240 | | | | | 245 | | | | | 250 | | | | | 255 | |

| GTG | GAA | CAG | CTG | AAG | GAC | TCT | ATT | GAT | AGG | GAT | AAA | ATA | GCC | ATT | ATT | 874 |
|---|---|---|---|---|---|---|---|---|---|---|---|---|---|---|---|---|
| Val | Glu | Gln | Leu | Lys | Asp | Ser | Ile | Asp | Arg | Asp | Lys | Ile | Ala | Ile | Ile | |
| | | | | 260 | | | | | 265 | | | | | 270 | | |

| GGA | CAT | TCT | TTT | GGT | GGA | GCC | ACA | GTT | ATT | CAG | ACT | CTT | AGT | GAA | GAC | 922 |
|---|---|---|---|---|---|---|---|---|---|---|---|---|---|---|---|---|
| Gly | His | Ser | Phe | Gly | Gly | Ala | Thr | Val | Ile | Gln | Thr | Leu | Ser | Glu | Asp | |
| | | | 275 | | | | | 280 | | | | | 285 | | | |

| CAG | AGA | TTC | AGG | TGT | GGC | ATT | GCT | CTG | GAT | GCA | TGG | ATG | TTT | CCC | GTG | 970 |
|---|---|---|---|---|---|---|---|---|---|---|---|---|---|---|---|---|
| Gln | Arg | Phe | Arg | Cys | Gly | Ile | Ala | Leu | Asp | Ala | Trp | Met | Phe | Pro | Val | |
| | | 290 | | | | | 295 | | | | | 300 | | | | |

| GGT | GAT | GAA | GTA | TAT | TCC | AGA | ATT | CCT | CAA | CCC | CTC | TTT | TTT | ATC | AAC | 1018 |
|---|---|---|---|---|---|---|---|---|---|---|---|---|---|---|---|---|
| Gly | Asp | Glu | Val | Tyr | Ser | Arg | Ile | Pro | Gln | Pro | Leu | Phe | Phe | Ile | Asn | |
| 305 | | | | | 310 | | | | | 315 | | | | | | |

| TCG | GAA | CGA | TTC | CAA | TAC | CCT | TCT | AAT | ATC | ATA | AGA | ATG | AAA | AAA | TGC | 1066 |
|---|---|---|---|---|---|---|---|---|---|---|---|---|---|---|---|---|
| Ser | Glu | Arg | Phe | Gln | Tyr | Pro | Ser | Asn | Ile | Ile | Arg | Met | Lys | Lys | Cys | |
| 320 | | | | | 325 | | | | | 330 | | | | | 335 | |

| TTC | TTA | CCT | GAT | AGA | GAA | CGA | AAA | ATG | ATT | ACA | ATC | AGG | GGT | TCG | GTC | 1114 |
|---|---|---|---|---|---|---|---|---|---|---|---|---|---|---|---|---|
| Phe | Leu | Pro | Asp | Arg | Glu | Arg | Lys | Met | Ile | Thr | Ile | Arg | Gly | Ser | Val | |
| | | | | 340 | | | | | 345 | | | | | 350 | | |

| CAT | CAG | AAT | TTT | GTT | GAC | TTC | ACT | TTT | GCC | ACT | AGC | AAA | ATA | ATT | GGC | 1162 |
|---|---|---|---|---|---|---|---|---|---|---|---|---|---|---|---|---|
| His | Gln | Asn | Phe | Val | Asp | Phe | Thr | Phe | Ala | Thr | Ser | Lys | Ile | Ile | Gly | |
| | | | 355 | | | | | 360 | | | | | 365 | | | |

| TAC | CTA | TTC | ACA | CTG | AAA | GGA | GAC | ATC | GAT | TCC | AAT | GTA | GCC | ATC | AGC | 1210 |
|---|---|---|---|---|---|---|---|---|---|---|---|---|---|---|---|---|
| Tyr | Leu | Phe | Thr | Leu | Lys | Gly | Asp | Ile | Asp | Ser | Asn | Val | Ala | Ile | Ser | |
| | | | 370 | | | | | 375 | | | | | 380 | | | |

| CTT | AGC | AAC | AAA | GCT | TCC | TTA | GCG | TTC | TTA | CAA | AAA | CAT | TTA | GGA | CTT | 1258 |
|---|---|---|---|---|---|---|---|---|---|---|---|---|---|---|---|---|

```
        Leu Ser Asn Lys Ala Ser Leu Ala Phe Leu Gln Lys His Leu Gly Leu
            385                 390                 395

CAG AAA GAT TTT GAT CAG TGG GAT TCT TTA GTT GAA GGC GAA GAT CAC        1306
Gln Lys Asp Phe Asp Gln Trp Asp Ser Leu Val Glu Gly Glu Asp His
400                 405                 410                 415

AAT CTT ATT CCA GGG ACC AAC ATT AAC ACA ACC AAC CAC CAA GCC ATT        1354
Asn Leu Ile Pro Gly Thr Asn Ile Asn Thr Thr Asn His Gln Ala Ile
                420                 425                 430

CTG CAG AAC TCC ACA GGA ATA GAG AGA CCA AAT TTA GAT T AAAAGAGCTT       1404
Leu Gln Asn Ser Thr Gly Ile Glu Arg Pro Asn Leu Asp
            435                 440

TTTAAAAAGT TTTGTTTACG AACTTGTCTA AAAGTGTGTG TGTGTATGAT TTAAATGTAT      1464

TTTCTCAAAT AGCTCATATT AAAAAATGTA GGCTATAGCA CAAAAAAAAA AAAAAAAAA       1524

AAAAAAAAA                                                              1533

(2) INFORMATION FOR SEQ ID NO:24:

(i) SEQUENCE CHARACTERISTICS:
        (A) LENGTH: 1876 base pairs
        (B) TYPE: nucleic acid
        (C) STRANDEDNESS: single
        (D) TOPOLOGY: linear (ii) MOLECULE TYPE: protein (ix) FEATURE:
        (A) NAME/KEY: CDS
        (B) LOCATION: 468..1734

(xi) SEQUENCE DESCRIPTION: SEQ ID NO:24:

CGGCGGGCTG CTGGCCCTTC CCGGCTGTTC GTAGAGCCGG ATCCTGCAGC GCCCCTGAGA        60

CGAACCGCCC CGATGCGGTG CTCCTCAGCG CCACGGGACG CAGCCGGGGC CGGCCGTGTT       120

GGCGCAGCTC CCACGACGTA CGCTTCCTTT CCAGGCTCGA GGAAAGCCTC TCCCACAAAC       180

ACCGTCCCAG CTGGGAAGTG AGGCGGAGTT TTGGTCCCTC CCCTCCGGCA GCGCCCGGCA       240

TTCCGTCCGT CCGTCCGTCC GTCCGTGCGG CGCACGGCGC CCTGCAGAGC CGGGACACCG       300

CAGCAGGGTA GGAGGACCCG GAGGTGGTGT GCAGCCACAG GTTTCCATCC TGCCCCCACC       360

TCCCGGGGAG CAGCCCTGTG CTATACCCAA CCCCCCGCAC AGAGCACTGA GCCGGCTGCT       420

GCCTGCCTGC ACCCCGCCGT GGGACCTTCT GCTCTTCCCA ACAAGTG ATG GCA TCG        476
                                                    Met Ala Ser
                                                      1

CTG TGG GTG AGA GCC AGG AGG GTG TTC ATG AAA AGT CGT GCT TCA GGT        524
Leu Trp Val Arg Ala Arg Arg Val Phe Met Lys Ser Arg Ala Ser Gly
    5                  10                  15

TTC TCG GCG AAG GCG GCG ACG GAG ATG GGG AGC GGC GGC GCG GAG AAG        572
Phe Ser Ala Lys Ala Ala Thr Glu Met Gly Ser Gly Gly Ala Glu Lys
 20                  25                  30                  35

GGC TAT CGG ATC CCC GCC GGG AAG GGC CCG CAC GCC GTG GGC TGC ACG        620
Gly Tyr Arg Ile Pro Ala Gly Lys Gly Pro His Ala Val Gly Cys Thr
                40                  45                  50

GAT CTG ATG ACC GGC GAC GCG GCC GAG GGA AGC TTT TTG CGC CTG TAT        668
Asp Leu Met Thr Gly Asp Ala Ala Glu Gly Ser Phe Leu Arg Leu Tyr
            55                  60                  65

TAC CTA TCG TGT GAC GAC ACA GAT ACT GAA GAG ACA CCC TGG ATT CCA        716
Tyr Leu Ser Cys Asp Asp Thr Asp Thr Glu Glu Thr Pro Trp Ile Pro
        70                  75                  80

GAT AAA GAG TAC TAC CAG GGG CTG TCT GAC TTC CTC AAC GTG TAC CGG        764
Asp Lys Glu Tyr Tyr Gln Gly Leu Ser Asp Phe Leu Asn Val Tyr Arg
    85                  90                  95
```

```
GCC CTG GGA GAA AGG CTT TTC CAG TAC TAC GTT GGC TCA GTG ACC TGT        812
Ala Leu Gly Glu Arg Leu Phe Gln Tyr Tyr Val Gly Ser Val Thr Cys
100             105                 110                 115

CCT GCA AAA TCA AAC GCT GCT TTT AAG CCA GGA GAG AAA TAC CCA CTG        860
Pro Ala Lys Ser Asn Ala Ala Phe Lys Pro Gly Glu Lys Tyr Pro Leu
            120                 125                 130

CTC GTT TTT TCC CAT GGA CTT GGA GCT TTT CGG ACC ATC TAT TCT GCT        908
Leu Val Phe Ser His Gly Leu Gly Ala Phe Arg Thr Ile Tyr Ser Ala
                135                 140                 145

ATC TGC ATA GAG ATG GCT TCT CAA GGC TTT CTA GTG GCA GCT GTG GAG        956
Ile Cys Ile Glu Met Ala Ser Gln Gly Phe Leu Val Ala Ala Val Glu
            150                 155                 160

CAC AGA GAT GAA TCG GCT TCA GCA ACG TAT TTC TGT AAA AAG AAG GCT       1004
His Arg Asp Glu Ser Ala Ser Ala Thr Tyr Phe Cys Lys Lys Lys Ala
165             170                 175

GAT TCT GAG CCA GAG GAG GAT CAA ACA TCA GGC GTG GAG AAG GAG TGG       1052
Asp Ser Glu Pro Glu Glu Asp Gln Thr Ser Gly Val Glu Lys Glu Trp
180             185                 190                 195

ATC TAC TAC AGG AAG CTC AGA GCA GGA GAG GAG GAG CGC TGT CTG CGT       1100
Ile Tyr Tyr Arg Lys Leu Arg Ala Gly Glu Glu Glu Arg Cys Leu Arg
                200                 205                 210

CAC AAG CAG GTA CAG CAG AGA GCA CAG GAG TGC ATC AAA GCG CTC AAC       1148
His Lys Gln Val Gln Gln Arg Ala Gln Glu Cys Ile Lys Ala Leu Asn
            215                 220                 225

CTC ATT CTT AAG ATC AGT TCA GGA GAG GAA GTG ATG AAT GTG CTG AAC       1196
Leu Ile Leu Lys Ile Ser Ser Gly Glu Glu Val Met Asn Val Leu Asn
                230                 235                 240

TCA GAC TTT GAC TGG AAC CAC CTG AAG GAT TCT GTT GAT ACT AGC AGA       1244
Ser Asp Phe Asp Trp Asn His Leu Lys Asp Ser Val Asp Thr Ser Arg
            245                 250                 255

ATA GCT GTG ATG GGA CAC TCT TTT GGT GGT GCT ACA GTT ATT GAG AGC       1292
Ile Ala Val Met Gly His Ser Phe Gly Gly Ala Thr Val Ile Glu Ser
260             265                 270                 275

CTC AGC AAA GAA ATT AGA TTT AGG TGT GGC ATT GCC CTT GAT GCG TGG       1340
Leu Ser Lys Glu Ile Arg Phe Arg Cys Gly Ile Ala Leu Asp Ala Trp
                280                 285                 290

ATG CTC CCG GTA GGC GAT GAC ACT TAC CAA AGC AGT GTG CAG CAA CCA       1388
Met Leu Pro Val Gly Asp Asp Thr Tyr Gln Ser Ser Val Gln Gln Pro
            295                 300                 305

CTG CTC TTT ATT AAT TCC GAA AAA TTC CAG TGG GCT GCC AAT ATC TTA       1436
Leu Leu Phe Ile Asn Ser Glu Lys Phe Gln Trp Ala Ala Asn Ile Leu
                310                 315                 320

AAG ATG AAG AAG CTT AGC TCC AAT GAT ACC AAC AAG AAA ATG ATC ACC       1484
Lys Met Lys Lys Leu Ser Ser Asn Asp Thr Asn Lys Lys Met Ile Thr
            325                 330                 335

ATC AAA GGA TCG GTA CAT CAG AGC TTT CCT GAT TTT ACT TTT GTG AGT       1532
Ile Lys Gly Ser Val His Gln Ser Phe Pro Asp Phe Thr Phe Val Ser
340             345                 350                 355

GGA GAA ATC ATT GGA AAG TTT TTC AAG TTA AAA GGA GAA ATA GAC CCA       1580
Gly Glu Ile Ile Gly Lys Phe Phe Lys Leu Lys Gly Glu Ile Asp Pro
                360                 365                 370

AAT GAA GCT ATT GAT ATA TGC AAC CAC GCT TCA TTG GCC TTC CTG CAG       1628
Asn Glu Ala Ile Asp Ile Cys Asn His Ala Ser Leu Ala Phe Leu Gln
            375                 380                 385

AAA CAT CTG AGT CTT AAG AGA GAT TTT GAT AAG TGG GAT TCA CTC GTG       1676
Lys His Leu Ser Leu Lys Arg Asp Phe Asp Lys Trp Asp Ser Leu Val
                390                 395                 400

GAT GGC ATA GGA CCC AAT GTT ATT TCT GGT ACC AAT ATC GAC TTA TCT       1724
Asp Gly Ile Gly Pro Asn Val Ile Ser Gly Thr Asn Ile Asp Leu Ser
405             410                 415
```

```
CCA ACT GAG T AAGGAGTACA AGAAGTACTG CAAAGGCCAC CAGCAGCAGG          1774
Pro Thr Glu
420

ACACCAACGT TGGCCACACA TTGCTTGGAG CTGAGATAGC ACTGGCCTCC CACACAGCTT  1834

TTGGAGTGTG AAACAACAAA AAAAAAAATC ACAGGGGAGC CG                    1876
```

(2) INFORMATION FOR SEQ ID NO:25:

(i) SEQUENCE CHARACTERISTICS:
        (A) LENGTH: 517 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..514

(xi) SEQUENCE DESCRIPTION: SEQ ID NO:25:

```
G GGG CAT TCT TTT GGA GGA GCA ACA GTT TTT CAA GCC CTA AGT GAA      46
  Gly His Ser Phe Gly Gly Ala Thr Val Phe Gln Ala Leu Ser Glu
   1               5                  10                  15

GAC CAG AGA TTC AGA TGT GGG ATT GCC CTT GAT CCG TGG ATG TTT CCC    94
Asp Gln Arg Phe Arg Cys Gly Ile Ala Leu Asp Pro Trp Met Phe Pro
                 20                  25                  30

GTG AGT GAG GAG CTG TAC TCC AGA GTT CCT CAG CCT CTC TTC TTT ATC   142
Val Ser Glu Glu Leu Tyr Ser Arg Val Pro Gln Pro Leu Phe Phe Ile
             35                  40                  45

AAC TCT GCC GAA TTC CAG ACT CCA AAG GAC ATT GCA AAA ATG AAA AAC   190
Asn Ser Ala Glu Phe Gln Thr Pro Lys Asp Ile Ala Lys Met Lys Asn
         50                  55                  60

TTC TAC CAG CCT GAC AAG GAA AGG AAA ATG ATT ACG ATC AAG GGC TCA   238
Phe Tyr Gln Pro Asp Lys Glu Arg Lys Met Ile Thr Ile Lys Gly Ser
     65                  70                  75

GTG CAC CAG AAT TTT GCT GAC GGG ACT TTT GTA ACT GGC AAA ATA ATT   286
Val His Gln Asn Phe Ala Asp Gly Thr Phe Val Thr Gly Lys Ile Ile
 80                  85                  90                  95

GGA AAC AAG CTG TCA CTG AAA GGA GAC ATA GAC TCC AGA GTT GCC ATA   334
Gly Asn Lys Leu Ser Leu Lys Gly Asp Ile Asp Ser Arg Val Ala Ile
                100                 105                 110

GAC CTC ACC AAC AAG GCT TCC TTG GCT TTC TTA CAA AAA CAT TTA GGA   382
Asp Leu Thr Asn Lys Ala Ser Leu Ala Phe Leu Gln Lys His Leu Gly
            115                 120                 125

CTT CAT AAA GAC TTT GAT CAG TGG GAC TGT CTG GTG GAG GGA GAG AAC   430
Leu His Lys Asp Phe Asp Gln Trp Asp Cys Leu Val Glu Gly Glu Asn
        130                 135                 140

GAG AAC CTC ATC CCG GGG TCA CCC TTT GAT GTA GTC ACC CAG TCC CCG   478
Glu Asn Leu Ile Pro Gly Ser Pro Phe Asp Val Val Thr Gln Ser Pro
    145                 150                 155

GCT CTG CAG AGT TCT CCC GGA TCA CAC AAC CAG AAT TAG               517
Ala Leu Gln Ser Ser Pro Gly Ser His Asn Gln Asn
160                 165                 170
```

(2) INFORMATION FOR SEQ ID NO:26:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: cDNA (ix) FEATURE:
  (A) NAME/KEY: CDS
  (B) LOCATION: 1..580

(xi) SEQUENCE DESCRIPTION: SEQ ID NO:26:

| | | | | | | | | | | | | | | | | |
|---|---|---|---|---|---|---|---|---|---|---|---|---|---|---|---|---|
| CAA | GTA | CTG | ATG | GCT | GCT | GCA | AGC | TTT | GGC | GAA | CGT | AAA | ATC | CCT | AAG | 48 |
| Gln | Val | Leu | Met | Ala | Ala | Ala | Ser | Phe | Gly | Glu | Arg | Lys | Ile | Pro | Lys | |
| 1 | | | | 5 | | | | | 10 | | | | | 15 | | |
| GGA | AAT | GGG | CCT | TAT | TCC | GTT | GGT | TGT | ACA | GAC | TTA | ATG | TTT | GAT | TAC | 96 |
| Gly | Asn | Gly | Pro | Tyr | Ser | Val | Gly | Cys | Thr | Asp | Leu | Met | Phe | Asp | Tyr | |
| | | | 20 | | | | | 25 | | | | | 30 | | | |
| ACT | AAA | AAG | GGC | ACC | TTC | TTG | CGT | TTA | TAT | TAT | CCA | TCC | CAA | GAT | GAT | 144 |
| Thr | Lys | Lys | Gly | Thr | Phe | Leu | Arg | Leu | Tyr | Tyr | Pro | Ser | Gln | Asp | Asp | |
| | | 35 | | | | | 40 | | | | | 45 | | | | |
| GAT | CGC | CTT | GAC | ACC | CTT | TGG | ATC | CCA | AAT | AAG | GAG | TAT | TTT | TGG | GGT | 192 |
| Asp | Arg | Leu | Asp | Thr | Leu | Trp | Ile | Pro | Asn | Lys | Glu | Tyr | Phe | Trp | Gly | |
| | 50 | | | | 55 | | | | | 60 | | | | | | |
| CTT | AGC | AAG | TAT | CTT | GGA | AAA | CAC | TGG | CTT | ATG | GGC | AAC | ATT | TTG | AGT | 240 |
| Leu | Ser | Lys | Tyr | Leu | Gly | Lys | His | Trp | Leu | Met | Gly | Asn | Ile | Leu | Ser | |
| 65 | | | | | 70 | | | | | 75 | | | | | 80 | |
| TTA | CTC | TTT | GGT | TCA | GTG | ACA | ACT | CCT | GCA | AAC | TGG | AAT | TCC | CCT | CTG | 288 |
| Leu | Leu | Phe | Gly | Ser | Val | Thr | Thr | Pro | Ala | Asn | Trp | Asn | Ser | Pro | Leu | |
| | | | | 85 | | | | | 90 | | | | | 95 | | |
| AGG | CCT | GGT | GAA | AAA | TAC | CCA | CTT | GTT | GTT | TTT | TCT | CAT | GGT | CTT | GGA | 336 |
| Arg | Pro | Gly | Glu | Lys | Tyr | Pro | Leu | Val | Val | Phe | Ser | His | Gly | Leu | Gly | |
| | | | 100 | | | | | 105 | | | | | 110 | | | |
| GCA | TTC | AGG | ACA | ATT | TAT | TCT | GCT | ATT | GGC | ATT | GAC | CTG | GCA | TCT | CAT | 384 |
| Ala | Phe | Arg | Thr | Ile | Tyr | Ser | Ala | Ile | Gly | Ile | Asp | Leu | Ala | Ser | His | |
| | | 115 | | | | | 120 | | | | | 125 | | | | |
| GGG | TTT | ATA | GTT | GCT | GCT | GTA | GAA | CAC | AGA | GAT | AGA | TCT | GCA | TCT | GCA | 432 |
| Gly | Phe | Ile | Val | Ala | Ala | Val | Glu | His | Arg | Asp | Arg | Ser | Ala | Ser | Ala | |
| | 130 | | | | | 135 | | | | | 140 | | | | | |
| ACT | TAC | TAT | TTC | AAG | AAC | CAA | TCT | GCT | GCA | GAA | ATA | GGG | AAA | AAG | TCT | 480 |
| Thr | Tyr | Tyr | Phe | Lys | Asn | Gln | Ser | Ala | Ala | Glu | Ile | Gly | Lys | Lys | Ser | |
| 145 | | | | 150 | | | | | 155 | | | | | 160 | | |
| TGG | CTC | TAC | CTT | AGA | ACC | CTG | AAA | GAA | GAG | GAG | GAG | ATA | CAT | ATA | CGA | 528 |
| Trp | Leu | Tyr | Leu | Arg | Thr | Leu | Lys | Glu | Glu | Glu | Glu | Ile | His | Ile | Arg | |
| | | | | 165 | | | | | 170 | | | | | 175 | | |
| AAT | AAG | CAG | GTA | CGA | CAA | AGA | GCA | AAA | GAA | TGT | TCC | CAA | GCT | CTC | AGT | 576 |
| Asn | Lys | Gln | Val | Arg | Gln | Arg | Ala | Lys | Glu | Cys | Ser | Gln | Ala | Leu | Ser | |
| | | | 180 | | | | | 185 | | | | | 190 | | | |
| CTG | A | | | | | | | | | | | | | | | 580 |
| Leu | | | | | | | | | | | | | | | | |

(2) INFORMATION FOR SEQ ID NO:27:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:27:

Gly Xaa Ser Xaa Gly
1               5

(2) INFORMATION FOR SEQ ID NO:28:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:28:

TATTCTAGAA TTATGATACA AGTATTAATG GCTGCTGCAA G                     41

(2) INFORMATION FOR SEQ ID NO:29:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:29:

ATTGATATCC TAATTGTATT TCTCTATTCC TG                               32

(2) INFORMATION FOR SEQ ID NO:30:

(i) SEQUENCE CHARACTERISTICS:
       (A) LENGTH: 1335 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:30:

ATGGTACCCC CAAAGCTGCA CGTCCTGTTT TGTCTGTGTG GATGTCTCGC CGTCGTGTAC    60

CCCTTCGATT GGCAGTATAT CAACCCCGTG GCTCACATGA AGAGCAGCGC CTGGGTGAAT   120

AAGATCCAGG TGCTCATGGC CGCACCAAGC TTCGGTCAGA CCAAGATTCC TAGAGGCAAC   180

GGCCCCTACA GCGTGGGCTG CACCGATCTG ATGTTCGACC ATACCAACAA AGGAACTTTT   240

CTGAGACTGT ACTACCCCAG CCAGGACAAC GACAGACTGG ATACTCTGTG GATCCCAAAT   300

AAAGAATATT TTGGGGTCT TAGCAAATTT CTTGGAACAC ACTGGCTTAT GGGCAACATT   360

TTGAGGTTAC TCTTTGGTTC AATGACAACT CCTGCAAACT GGAATTCCCC TCTGAGGCCT   420

GGTGAAAAAT ATCCACTTGT TGTTTTTTCT CATGGTCTTG GGGCATTCAG GACACTTTAT   480

TCTGCTATTG GCATTGACCT GGCATCTCAT GGGTTTATAG TTGCTGCTGT AGAACACAGA   540

GATAGATCTG CATCTGCAAC TTACTATTTC AAGGACCAAT CTGCTGCAGA AATAGGGGAC   600

AAGTCTTGGC TCTACCTTAG AACCCTGAAA CAAGAGGAGG AGACACATAT ACGAAATGAG   660

CAGGTACGGC AAAGAGCAAA AGAATGTTCC CAAGCTCTCA GTCTGATTCT TGACATTGAT   720

CATGGAAAGC CAGTGAAGAA TGCATTAGAT TTAAAGTTTG ATATGGAACA ACTGAAGGAC   780

TCTATTGATA GGGAAAAAAT AGCAGTAATT GGACATTCTT TTGGTGGAGC AACGGTTATT   840

CAGACTCTTA GTGAAGATCA GAGATTCAGA TGTGGTATTG CCCTGGATGC ATGGATGTTT   900

CCACTGGGTG ATGAAGTATA TTCCAGAATT CCTCAGCCCC TCTTTTTTAT CAACTCTGAA   960

TATTTCCAAT ATCCTGCTAA TATCATAAAA ATGAAAAAAT GCTACTCACC TGATAAAGAA  1020

AGAAAGATGA TTACAATCAG GGGTTCAGTC CACCAGAATT TTGCTGACTT CACTTTTGCA  1080

ACTGGCAAAA TAATTGGACA CATGCTCAAA TTAAAGGGAG ACATAGATTC AAATGTAGCT  1140

ATTGATCTTA GCAACAAAGC TTCATTAGCA TTCTTACAAA AGCATTTAGG ACTTCATAAA  1200

| | |
|---|---|
| GATTTTGATC AGTGGGACTG CTTGATTGAA GGAGATGATG AGAATCTTAT TCCAGGGACC | 1260 |
| AACATTAACA CAACCAATCA ACACATCATG TTACAGAACT CTTCAGGAAT AGAGAAATAC | 1320 |
| AATTAGGATT CTAGA | 1335 |

PLATELET-ACTIVATING FACTOR ACETYLHYDROLASE

This application is a continuation-in-part of U.S. patent application Ser. No. 08/483,232 filed Jun. 7, 1995, now U.S. Pat. No. 5,656,431, which in turn is a continuation-in-part of U.S. patent application Ser. No. 08/318,905 filed Oct. 6, 1994, now U.S. Pat. No. 5,641,669, which in turn is a continuation-in-part of U.S. patent application Ser. No. 08/133,803 filed Oct. 6, 1993, now abandoned, all of which are incorporated herein by reference.

FIELD OF THE INVENTION

The present invention relates generally to platelet-activating factor acetylhydrolase and more specifically to novel purified and isolated polynucleotides encoding human plasma platelet-activating factor acetylhydrolase, to the platelet-activating factor acetylhydrolase products encoded by the polynucleotides, to materials and methods for the recombinant production of platelet-activating factor acetylhydrolase products and to antibody substances specific for platelet-activating factor acetylhydrolase.

BACKGROUND

Platelet-activating factor (PAF) is a biologically active phospholipid synthesized by various cell types. In vivo and at normal concentrations of $10^{-10}$ to $10^{-9}$ M, PAF activates target cells such as platelets and neutrophils by binding to specific G protein-coupled cell surface receptors [Venable et al., *J. Lipid Res.*, 34: 691–701 (1993)]. PAF has the structure 1-O-alkyl-2-acetyl-sn-glycero-3-phosphocholine. For optimal biological activity, the sn-1 position of the PAF glycerol backbone must be in an ether linkage with a fatty alcohol and the sn-3 position must have a phosphocholine head group.

PAF functions in normal physiological processes (e.g., inflammation, hemostasis and parturition) and is implicated in pathological inflammatory responses (e.g., asthma, anaphylaxis, septic shock and arthritis) [Venable et al., supra, and Lindsberg et al., *Ann. Neurol.*, 30: 117–129 (1991)]. The likelihood of PAF involvement in pathological responses has prompted attempts to modulate the activity of PAF and the major focus of these attempts has been the development of antagonists of PAF activity which interfere with binding of PAF to cell surface receptors. See, for example, Heuer et al., *Clin. Exp. Allergy*, 22: 980–983 (1992).

The synthesis and secretion of PAF as well as its degradation and clearance appear to be tightly controlled. To the extent that pathological inflammatory actions of PAF result from a failure of PAF regulatory mechanisms giving rise to excessive production, inappropriate production or lack of degradation, an alternative means of modulating the activity of PAF would involve mimicing or augmenting the natural process by which resolution of inflammation occurs. Macrophages [Stafforini et al., *J. Biol. Chem.*, 265(17): 9682–9687 (1990)], hepatocytes and the human hepatoma cell line HepG2 [Satoh et al., *J. Clin. Invest.*, 87: 476–481 (1991) and Tarbet et al., *J. Biol. Chem.*, 266(25): 16667–16673 (1991)] have been reported to release an enzymatic activity, PAF acetylhydrolase (PAF-AH), that inactivates PAF. In addition to inactivating PAF, PAF-AH also inactivates oxidatively fragmented phospholipids such as products of the arachidonic acid cascade that mediate inflammation. See, Stremler et al., *J. Biol. Chem.*, 266(17): 11095–11103 (1991). The inactivation of PAF by PAF-AH occurs primarily by hydrolysis of the PAF sn-2 acetyl group and PAF-AH metabolizes oxidatively fragmented phospholipids by removing sn-2 acyl groups. Two types of PAF-AH have been identified: cytoplasmic forms found in a variety of cell types and tissues such as endothelial cells and erythrocytes, and an extracellular form found in plasma and serum. Plasma PAF-AH does not hydrolyze intact phospholipids except for PAF and this substrate specificity allows the enzyme to circulate in vivo in a fully active state without adverse effects. The plasma PAF-AH appears to account for all of the PAF degradation in human blood ex vivo [Stafforini et al., *J. Biol. Chem.*, 262(9): 4223–4230 (1987)].

While the cytoplasmic and plasma forms of PAF-AH appear to have identical substrate specificity, plasma PAF-AH has biochemical characteristics which distinguish it from cytoplasmic PAF-AH and from other characterized lipases. Specifically, plasma PAF-AH is associated with lipoprotein particles, is inhibited by diisopropyl fluorophosphate, is not affected by calcium ions, is relatively insensitive to proteolysis, and has an apparent molecular weight of 43,000 daltons. See, Stafforini et al. (1987), supra. The same Stafforini et al. article describes a procedure for partial purification of PAF-AH from human plasma and the amino acid composition of the plasma material obtained by use of the procedure. Cytoplasmic PAF-AH has been purified from erythrocytes as reported in Stafforini et al., *J. Biol. Chem.*, 268(6): 3857–3865 (1993) and ten amino terminal residues of cytoplasmic PAF-AH are also described in the article. Hattori et al., *J. Biol. Chem.*, 268(25): 18748–18753 (1993) describes the purification of cytoplasmic PAF-AH from bovine brain. Subsequent to filing of the parent application hereto the nucleotide sequence of bovine brain cytoplasmic PAF-AH was published in Hattori et al., *J. Biol. Chem.*, 269(237): 23150–23155 (1994). On Jan. 5, 1995, three months after the filing date of the parent application hereto, a nucleotide sequence for a lipoprotein associated phospholipase $A_2$ (Lp-PLA$_2$) was published in Smithkline Beecham PLC Patent Cooperation Treaty (PCT) International Publication No. WO 95/00649. The nucleotide sequence of the Lp-PLA$_2$ differs at one position when compared to the nucleotide sequence of the PAF-AH of the present invention. The nucleotide difference (corresponding to position 1297 of SEQ ID NO: 7) results in an amino acid difference between the enzymes encoded by the polynucleotides. The amino acid at position 379 of SEQ ID NO: 8 is a valine while the amino acid at the corresponding position in Lp-PLA$_2$ is an alanine. In addition, the nucleotide sequence of the PAF-AH of the present invention includes 124 bases at the 5' end and twenty bases at the 3' end not present in the Lp-PLA$_2$ sequence. Three months later, on Apr. 10, 1995, a Lp-PLA$_2$ sequence was deposited in GenBank under Accession No. U24577 which differs at eleven positions when compared to the nucleotide sequence of the PAF-AH of the present invention. The nucleotide differences (corresponding to position 79, 81, 84, 85, 86, 121, 122, 904, 905, 911, 983 and 1327 of SEQ ID NO: 7) results in four amino acid differences between the enzymes encoded by the polynucleotides. The amino acids at positions 249, 250, 274 and 389 of SEQ ID NO: 8 are lysine, aspartic acid, phenylalanine and leucine, respectively, while the respective amino acid at the corresponding positions in the GenBank sequence are isoleucine, arginine, leucine and serine.

The recombinant production of PAF-AH would make possible the use of exogenous PAF-AH to mimic or augment normal processes of resolution of inflammation in vivo. The administration of PAF-AH would provide a physiological advantage over administration of PAF receptor antagonists because PAF-AH is a product normally found in plasma. Moreover, because PAF receptor antagonists which are structurally related to PAF inhibit native PAF-AH activity, the desirable metabolism of PAF and of oxidatively fragmented phospholipids is thereby prevented. Thus, the inhibition of PAF-AH activity by PAF receptor antagonists counteracts the competitive blockade of the PAF receptor by the antagonists. See, Stremler et al., supra. In addition, in locations of acute inflammation, for example, the release of oxidants results in inactivation of the native PAF-AH enzyme in turn resulting in elevated local levels of PAF and PAF-like compounds which would compete with any exogenously administed PAF receptor antagonist for binding to the PAF receptor. In contrast, treatment with recombinant PAF-AH would augment endogenous PAF-AH activity and compensate for any inactivated endogenous enzyme.

There thus exists a need in the art to identify and isolate polynucleotide sequences encoding human plasma PAF-AH, to develop materials and methods useful for the recombinant production of PAF-AH and to generate reagents for the detection of PAF-AH in plasma.

SUMMARY OF THE INVENTION

The present invention provides novel purified and isolated polynucleotides (i.e., DNA and RNA both sense and antisense strands) encoding human plasma PAF-AH or enzymatically active fragments thereof. Preferred DNA sequences of the invention include genomic and cDNA sequences as well as wholly or partially chemically synthesized DNA sequences. The DNA sequence encoding PAF-AH that is set out in SEQ ID NO: 7 and DNA sequences which hybridize to the noncoding strand thereof under standard stringent conditions or which would hybridize but for the redundancy of the genetic code, are contemplated by the invention. Also contemplated by the invention are biological replicas (i.e., copies of isolated DNA sequences made in vivo or in vitro) of DNA sequences of the invention. Autonomously replicating recombinant constructions such as plasmid and viral DNA vectors incorporating PAF-AH sequences and especially vectors wherein DNA encoding PAF-AH is operatively linked to an endogenous or exogenous expression control DNA sequence and a transcription terminator are also provided.

According to another aspect of the invention, procaryotic or eucaryotic host cells are stably transformed with DNA sequences of the invention in a manner allowing the desired PAF-AH to be expressed therein. Host cells expressing PAF-AH products can serve a variety of useful purposes. Such cells constitute a valuable source of immunogen for the development of antibody substances specifically immunoreactive with PAF-AH. Host cells of the invention are conspicuously useful in methods for the large scale production of PAF-AH wherein the cells are grown in a suitable culture medium and the desired polypeptide products are isolated from the cells or from the medium in which the cells are grown by, for example, immunoaffinity purification.

A non-immunological method contemplated by the invention for purifying PAF-AH from plasma includes the following steps: (a) isolating low density lipoprotein particles; (b) solubilizing said low density lipoprotein particles in a buffer comprising 10mM CHAPS to generate a first PAF-AH enzyme solution; (c) applying said first PAF-AH enzyme solution to a DEAE anion exchange column; (d) washing said DEAE anion exchange column using an approximately pH 7.5 buffer comprising 1 mM CHAPS; (e) eluting PAF-AH enzyme from said DEAE anion exchange column in fractions using approximately pH 7.5 buffers comprising a gradient of 0 to 0.5 M NaCl; (f) pooling fractions eluted from said DEAE anion exchange column having PAF-AH enzymatic activity; (g) adjusting said pooled, active fractions from said DEAE anion exchange column to 10 mM CHAPS to generate a second PAF-AH enzyme solution; (h) applying said second PAF-AH enzyme solution to a blue dye ligand affinity column; (i) eluting PAF-AH enzyme from said blue dye ligand affinity column using a buffer comprising 10 mM CHAPS and a chaotropic salt; (j) applying the eluate from said blue dye ligand affinity column to a Cu ligand affinity column; (k) eluting PAF-AH enzyme from said Cu ligand affinity column using a buffer comprising 10 mM CHAPS and imidazole; (l) subjecting the eluate from said Cu ligand affinity column to SDS-PAGE; and (m) isolating the approximately 44 kDa PAF-AH enzyme from the SDS-polyacrylamide gel. Preferably, the buffer of step (b) is 25 mM Tris-HCl, 10 mM CHAPS, pH 7.5; the buffer of step (d) is 25 mM Tris-HCl, 1 mM CHAPS; the column of step (h) is a Blue Sepharose Fast Flow column; the buffer of step (i) is 25 mM Tris-HCl, 10 mM CHAPS, 0.5M KSCN, pH 7.5; the column of step (j) is a Cu Chelating Sepharose column; and the buffer of step (k) is 25 mM Tris-HCl, 10 mM CHAPS, 0.5M NaCl, 50 mM imidazole at a pH in a range of about pH 7.5–8.0.

A method contemplated by the invention for purifying enzymatically-5 active PAF-AH from E. coli producing PAF-AH includes the steps of: (a) preparing a centrifugation supernatant from lysed E. coli producing PAF-AH enzyme; (b) applying said centrifugation supernatant to a blue dye ligand affinity column; (c) eluting PAF-AH enzyme from said blue dye ligand affinity column using a buffer comprising 10 mM CHAPS and a chaotropic salt; (d) applying said eluate from said blue dye ligand affinity column to a Cu ligand affinity column; and (e) eluting PAF-AH enzyme from said Cu ligand affinity column using a buffer comprising 10 mM CHAPS and imidazole. Preferably, the column of step (b) is a Blue Sepharose Fast Flow column; the buffer of step (c) is 25 mM Tris-HCl, 10 mM CHAPS, 0.5M KSCN, pH 7.5; the column of step (d) is a Cu Chelating Sepharose column; and the buffer of step (e) is 25 mM Tris-HCl, 10 mM CHAPS, 0.5M NaCl, 100 mM imidazole, pH 7.5.

Another method contemplated by the invention for purifying enzymatically-active PAF-AH from E. coli producing PAF-AH includes the steps of: (a) preparing a centrifugation supernatant from lysed E. coli producing PAF-AH enzyme; (b) diluting said centrifugation supernatant in a low pH buffer comprising 10 mM CHAPS; (c) applying said diluted centrifugation supernatant to a cation exchange column equilibrated at about pH 7.5; (d) eluting PAF-AH enzyme from said cation exchange column using 1M salt; (e) raising the pH of said eluate from said cation exchange column and adjusting the salt concentration of said eluate to about 0.5M salt; (f) applying said adjusted eluate from said cation exchange column to a blue dye ligand affinity column; (g) eluting PAF-AH enzyme from said blue dye ligand affinity column using a buffer comprising about 2M to about 3M salt; and (h) dialyzing said eluate from said blue dye ligand affinity column using a buffer comprising about 0.1% Tween. Preferably, the buffer of step (b) is 25 mM MES, 10 mM CHAPS, 1 mM EDTA, pH 4.9; the column of step (c) is an S sepharose column equilibrated in 25 mM MES, 10 mM CHAPS, 1 mM EDTA, 50 mM NaCl, pH 5.5; PAF-AH is eluted in step (d) using 1 mM NaCl; the pH of the eluate in step (e) is adjusted to pH 7.5 using 2M Tris base; the column in step (f) is a sepharose column; the buffer in step (g) is 25 mM Tris, 10 mM CHAPS, 3M NaCl, 1 mM EDTA, pH 7.5; and the buffer in step (h) is 25 mM Tris, 0.5M NaCl, 0.1% Tween 80, pH 7.5.

Still another method contemplated by the invention for purifying enzymatically-active PAF-AH from *E. coli* includes the steps of: (a) preparing an *E. coli* extract which yields solubilized PAF-AH supernatant after lysis in a buffer containing CHAPS; (b) dilution of said supernatant and application to a anion exchange column equilibrated at about pH 8.0; (c) eluting PAF-AH enzyme from said anion exchange column; (d) applying said adjusted eluate from said anion exchange column to a blue dye ligand affinity column; (e) eluting the said blue dye ligand affinity column using a buffer comprising 3.0M salt; (f) dilution of the blue dye eluate into a suitable buffer for performing hydroxylapatite chromatography; (g) performing hydroxylapatite chromatography where washing and elution is accomplished using buffers (with or without CHAPS); (h) diluting said hydroxylapatite eluate to an appropriate salt concentration for cation exchange chromatography; (i) applying said diluted hydroxylapatite eluate to a cation exchange column at a pH ranging between approximately 6.0 to 7.0; (j) elution of PAF-AH from said cation exchange column with a suitable formulation buffer; (k) performing cation exchange chromatography in the cold; and (l) formulation of PAF-AH in liquid or frozen form in the absence of CHAPS.

Preferably in step (a) above the lysis buffer is 25 mM Tris, 100 mM NaCl, 1 mM EDTA, 20 mM CHAPS, pH 8.0; in step (b) the dilution of the supernatant for anion exchange chromatography is 3–4 fold into 25 mM Tris, 1 mM EDTA, 10 mM CHAPS, pH 8.0 and the column is a Q-Sepharose column equilibrated with 25 mM Tris, 1 mM EDTA, 50 mM NaCl, 10 mM CHAPS, pH 8.0; in step (c) the anion exchange column is eluted using 25 mM Tris, 1 mM EDTA, 350 mM NaCl, 10 mM CHAPS, pH 8.0; in step (d) the eluate from step (c) is applied directly onto a blue dye affinity column; in step (e) the column is eluted with 3M NaCl, 10 mM CHAPS, 25 mM Tris, pH 8.0 buffer; in step (f) dilution of the blue dye eluate for hydroxylapatite chromatography is accomplished by dilution into 10 mM sodium phosphate, 100 mM NaCl, 10 mM CHAPS, pH 6.2; in step (g) hydroxylapatite chromatography is accomplished using a hydroxylapatite column equilibrated with 10 mM sodium phosphate, 100 mM NaCl. 10 mM CHAPS and elution is accomplished using 50 mM sodium phosphate. 100 mM NaCl (with or without) 10 mM CHAPS, pH 7.5; in step (h) dilution of said hydroxylapatite eluate for cation exchange chromatography is accomplished by dilution into a buffer ranging in pH from approximately 6.0 to 7.0 comprising sodium phosphate (with or without CHAPS); in step (i) a S Sepharose column is equilibrated with 50 mM sodium phosphate, (with or without) 10 mM CHAPS, pH 6.8; in step (j) elution is accomplished with a suitable formulation buffer such as potassium phosphate 50 mM, 12.5 mM aspartic acid, 125 mM NaCl, pH 7.5 containing 0.01% Tween-80; and in step (k) cation exchange chromatrography is accomplished at 2–8° C. Examples of suitable formulation buffers for use in step (l) which stabilize PAF-AH include 50 mM potassium phosphate, 12.5 mM Aspartic acid, 125 mM NaCl pH 7.4 (approximately, with and without the addition of Tween-80 and or Pluronic F68) or 25 mM potassium phosphate buffer containing (at least) 125 mM NaCl, 25 mM arginine and 0.01% Tween-80 (with or without Pluronic F68 at approximately 0.1 and 0.5%).

Yet another method contemplated by the invention for purifying enzymatically active rPAF-AH products from *E. coli* includes the steps of: (a) preparing an *E. coli* extract which yields solubilized rPAF-AH product supernatant after lysis in a buffer containing Triton X-100, (b) dilution of said supernatant and application to an immobilized metal affinity exchange column equilibrated at about pH 8.0; (c) eluting rPAF-AH product from said immobilized metal affinity exchange column with a buffer comprising imidazole; (d) adjusting the salt concentration and applying said eluate from said immobilized metal affinity column to an hydrophobic interaction column (HIC#1); (e) eluting said HIC#1 by reducing the salt concentration and/or increasing the detergent concentration; (f) titrating said HIC#1 eluate to a pH of about 6.4; (g) applying said adjusted HIC#1 eluate to a cation exchange column (CEX#1) equilibrated at about pH 6.4; (h) eluting said CEX#1 with concentration? sodium chloride; (i) adjusting said CEX#1 eluate with sodium chloride to a concentration of about 2.0M; (j) applying said adjusted CEX#1 eluate to a hydrophobic interaction column (HIC#2) equilibrated at about pH 8.0 and about 2.0M sodium chloride; (k) eluting said HIC#2 hy reducing the salt concentration and/or increasing the detergent concentration; (l) diluting said HIC#2 eluate and adjusting to a pH of about 6.0; (m) applying said adjusted HIC#2 eluate to a cation exchange column (CEX#2) equilibrated at about pH 6.0; (n) eluting the rPAF-AH product from said CEX#2 with a suitable formulation buffer.

Preferably, in step (a) above the lysis buffer is 90 mM TRIS, 0.125% Triton X-100, 0.6M NaCl, pH 8.0, and lysis is carried out in a high pressure homogenizer; in step (b) the supernatant is diluted into equilibration buffer (20 mM TRIS, 0.5M NaCl, 0.1% Triton X-100, pH 8.0), a zinc chelate column (Chelating Sepharose Fast Flow, Pharmacia, Uppsala, Sweden) is charged, equilibrated with equilibration buffer, loaded with the diluted supernatant, and washed with 20 mM TRIS, 0.5M NaCl, 4M urea, 0.1% Triton X-100, pH 8.0, followed by washing with 20 mM TRIS, 0.5M NaCl, 0.02% Triton X-100, pH 8.0; in step (c) elution is accomplished with 20 mM Tris, 50 mM imidazole, 0.02% Triton X-100, pH 8.0; in step (d) the eluate is adjusted to 1 mM EDTA and 2M NaCl, a Phenyl Sepharose 6 Fast Flow (Pharmacia) is equilibrated with equilibration buffer (2.0M NaCl, 25 mM Tris, 0.02% Triton X-100, pH 8.0), loaded with the adjusted eluate from step (c) at room temperature, washed with equilibration buffer, and washed with 25 mM NaPO$_4$, 0.02% Triton X-100, pH6.5 at a flow rate of 30 cm/hr; in step (e) elution is accomplished with 25 mM NaPO$_4$, 3% Triton X-100, pH 6.5; in step (g) a Macro-Prep High S Column (Bio-Rad Labs, Richmond, Calif.) is equilibrated with equilibration buffer (20 mM NaPO$_4$, 0.02% Triton X-100, pH 6.4), loaded with the adjusted eluate from step (f), washed with equilibration buffer, and washed with 25 mM Tris, 0.02% Triton X-100, pH 8.0; in step (h) elution is accomplished with 25 mM Tris, 0.02% Triton X-100, 1.3M NaCl, pH 8.0; in step (j) a Bakerbond Wide Pore Hi-Propyl C$_3$ (Baker, Phillipsburg, N.J.) is equilibrated with equilibration buffer (2.0M NaCl, 25 mM Tris, 0.02% Triton X-100, pH 8.0), loaded with adjusted eluate from step (i) at room temperature, washed with equilibration buffer, and washed with 25 mM Tris, 0.02% Triton X-100, pH 8.0 at 30 cm/hr; in step (k) elution is accomplished with 10 mM Tris, 3.0% Triton X-100, pH 8.0; in step (l) dilution is into equilibration buffer (20 mM succinate, 0.1% PLURONIC F68, pH 6.0); in step (m) a SP Sepharose Fast Flow (Pharmacia) column is equilibrated with the equilibration buffer of step (l), loaded with eluate from step (l), and washed with equilibration buffer; and in step (n) elution is accomplished with 50 mM NaPO$_4$, 0.7M NaCl, 0.1% PLURONIC F68, 0.02% TWEEN 80, pH 7.5.

PAF-AH products may be obtained as isolates from natural cell sources or may be chemically synthesized, but are preferably produced by recombinant procedures involving procaryotic or eucaryotic host cells of the invention. PAF-AH products having part or all of the amino acid sequence set out in SEQ ID NO: 8 are contemplated. Specifically contemplated are fragments lacking up to the first twelve N-terminal amino acids of the mature human PAF-AH amino acid sequence set out in SEQ ID NO: 8, particularly those having $Met_{46}$, $Ala_{47}$ or $Ala_{48}$ of SEQ ID NO: 8 as the initial N-terminal amino acid. Also contemplated are fragments thereof lacking up to thirty C-terminal amino acids of the amino acid sequence of SEQ ID NO: 8, particularly those having $Ile_{429}$ and $Leu_{431}$ as the C-terminal residue. Further contemplated are variants of PAF-AH or PAF-AH or which have an amino acid replacement in the sequence of SEQ ID NO: 8 selected from the group consisting of S 108 A, S 273 A, D 286 A, D 286 N, D 296 A, D 304 A, D 338 A, H 351 A, H 395 A, H 399 A, C 67 S, C 229 S, C 291 S, C 334 S, C 407 S, D 286 A, D 286 N and D 304 A. As noted above, polynucleotides (including DNA) encoding such fragments or variant fragments are provided by the invention, as well as methods of recombinantly producing such fragments or variants by growing host cells comprising such DNA. Presently preferred PAF-AH products include the prokaryotic polypeptide expression products of DNA encoding amino acid residues $Met_{46}$ through $Asn_{441}$ of SEQ ID NO: 8, designated rPH.2, and the prokaryotic polypeptide expression products of DNA encoding amino acid residues $Met_{46}$ through $Ile_{429}$ of SEQ ID NO: 8, designated rPH.9. Both the rPH.2 and rPH.9 products display less amino-terminal heterogeneity than, for example, the corresponding prokaryotic expression products of DNA encoding the full mature sequence of PAF-AH preceded by a translation initiation codon. Moreover, the rPH.9 product displays greater carboxy terminal homogeneity (consistency). The use of mammalian host cells is expected to provide for such post-translational modifications (e.g., myristolation, glycosylation, truncation, lipidation and tyrosine, serine orthreoninephosphorylation) as may be needed to confer optimal biological activity on recombinant expression products of the invention. PAF-AH products of the invention may be full length polypeptides, fragments or variants. Variants may comprise PAF-AH analogs wherein one or more of the specified (i.e., naturally encoded) amino acids is deleted or replaced or wherein one or more non-specified amino acids are added: (1) without loss of one or more of the enzymatic activities or immunological characteristics specific to PAF-AH; or (2) with specific disablement of a particular biological activity of PAF-AH. Proteins or other molecules that bind to PAF-AH may be used to modulate its activity.

Also comprehended by the present invention are antibody substances (e.g., monoclonal and polyclonal antibodies, single chain antibodies, chimeric antibodies, CDR-grafted antibodies and the like) and other binding proteins specific for PAF-AH. Specifically illustrating binding proteins of the invention are the monoclonal antibodies produced by hybridomas 90G11D and 90F2D which were deposited with the American Type Culture Collection (ATCC), 12301 Parklawn Drive, Rockville, Md. 20852 on Sep. 30, 1994 and were respectively assigned Accession Nos. HB 11724 and HB 11725. Also illustrating binding proteins of the invention is the monoclonal antibody produced by hybridoma 143A which was deposited with the ATCC on Jun. 1, 1995 and assigned Accession No. HB 11900. Proteins or other molecules (e.g., lipids or small molecules) which specifically bind to PAF-AH can be identified using PAF-AH isolated from plasma, recombinant PAF-AH, PAF-AH variants or cells expressing such products. Binding proteins are useful, in turn, in compositions for immunization as well as for purifying PAF-AH, and are useful for detection or quantification of PAF-AH in fluid and tissue samples by known immunological procedures. Anti-idiotypic antibodies specific for PAF-AH-specific antibody substances are also contemplated.

The scientific value of the information contributed through the disclosures of DNA and amino acid sequences of the present invention is manifest. As one series of examples, knowledge of the sequence of a cDNA for PAF-AH makes possible the isolation by DNA/DNA hybridization of genomic DNA sequences encoding PAF-AH and specifying PAF-AH expression control regulatory sequences such as promoters, operators and the like. DNA/DNA hybridization procedures carried out with DNA sequences of the invention under conditions of stringency standard in the art are likewise expected to allow the isolation of DNAs encoding allelic variants of PAF-AH, other structurally related proteins sharing one or more of the biochemical and/or immunological properties of PAF-AH, and non-human species proteins homologous to PAF-AH. The DNA sequence information provided by the present invention also makes possible the development, by homologous recombination or "knockout" strategies [see, e.g., Kapecchi, *Science*, 244: 1288–1292 (1989)], of rodents that fail to express a functional PAF-AH enzyme or that express a variant PAF-AH enzyme. Polynucleotides of the invention when suitably labelled are useful in hybridization assays to detect the capacity of cells to synthesize PAF-AH. Polynucleotides of the invention may also be the basis for diagnostic methods useful for identifying a genetic alteration(s) in the PAF-AH locus that underlies a disease state or states. Also made available by the invention are anti-sense polynucleotides relevant to regulating expression of PAF-AH by those cells which ordinarily express the same.

Administration of PAF-AH preparations of the invention to mammalian subjects, especially humans, for the purpose of ameliorating pathological inflammatory conditions is contemplated. Based on implication of the involvement of PAF in pathological inflammatory conditions, the administration of PAF-AH is indicated, for example, in treatment of asthma [Miwa et al., *J. Clin. Invest.*, 82: 1983–1991 (1988); Hsieh et al., *J. Allergy Clin. Immunol.*, 91: 650–657 (1993); and Yamashita et al., *Allergy*, 49: 60–63 (1994)], anaphylaxis [Venable et al., supra], shock [Venable et al., supra], reperfusion injury and central nervous system ischemia [Lindsberg et al. (1991), supra], antigen-induced arthritis [Zarco et al., *Clin. Exp. Immunol.*, 88: 318–323 (1992)], atherogenesis [Handley et al., *Drug Dev. Res.*, 7: 361–375 (1986)], Crohn's disease [Denizot et al., *Digestive Diseases and Sciences*, 37(3): 432–437 (1992)], ischemic bowel necrosis/necrotizing enterocolitis [Denizot et al., supra and Caplan et al., *Acta Paediatr., Suppl.* 396: 11–17 (1994)], ulcerative colitis (Denizot et al., supra), ischemic stroke [Satoh et al., Stroke, 23: 1090–1092 (1992)], ischemic brain injury [Lindsberg et al., *Stroke*, 21: 1452–1457 (1990) and Lindsberg et al. (1991), supra], systemic lupus erythematosus [Matsuzaki et al., *Clinica Chimica Acta*, 210: 139–144 (1992)], acute pancreatitis [Kald et al., *Pancreas*, 8(4): 440–442 (1993)], septicemia (Kald et al., supra), acute post streptococcal glomerulonephritis [Mezzano et al., *J. Am. Soc. Nephrol.*, 4: 235–242 (1993)], pulmonary edema resulting from IL-2 therapy [Rabinovici et al., *J. Clin. Invest.*, 89: 1669–1673 (1992)], allergic inflammation [Watanabe et al., Br. J. Pharmacol., 111: 123–130 (1994)], ischemic renal failure [Grino et al., Annals of Internal Medicine, 121(5): 345–347 (1994); preterm labor [Hoffman et al., Am. J. Obstet. Gynecol., 162(2): 525–528 (1990) and Maki et al., Proc. Natl. Acad. Sci. USA, 85: 728–732 (1988)]; adult respiratory distress syndrome [Rabinovici et al., J. Appl. Physiol., 74(4): 1791–1802 (1993); Matsumoto et al., Clin. Exp. Pharmacol. Physiol., 19 509–515 (1992); and Rodriguez-Roisin et al., J. Clin. Invest., 93: 188–194 (1994)]. Also contemplated is the use of PAF-AH preparations to treat human immunodeficiency virus (HIV) infection of the central nervous system. "Treatment" as used herein includes both prophylactic and therapeutic treatment.

Animal models for many of the foregoing pathological conditions have been described in the art. For example, a mouse model for asthma and rhinitis is described in Example 16 herein; a rabbit model for arthritis is described in Zarco et at., supra; rat models for ischemic bowel necrosis/necrotizing enterocolitis are described in Furukawa et al., Ped. Res., 34,(2): 237–241 (1993) and Caplan et al., supra; a rabbit model for stroke is described in Lindsberg et al., (1990), supra; a mouse model for lupus is described in Matsuzaki et al., supra; a rat model for acute pancreatitis is described in Kald et al., supra: a rat model for pulmonary edema resulting from IL-2 therapy is described in Rabinovici et al., supra; a rat model of allergic inflammation is described in Watanabe et al., supra); a canine model of renal allograft is described in Watson et al., Transplantation, 56(4): 1047–1049 (1993); and rat and guinea pig models of adult respiratory distress syndrome are respectively described in Rabinovici et al., supra. and Lellouch-Tubiana, Am. Rev. Respir. Dis., 137: 948–954 (1988).

Specifically contemplated by the invention are PAF-AH compositions for use in methods for treating a mammal susceptible to or suffering from PAF-mediated pathological conditions comprising administering PAF-AH to the mammal in an amount sufficient to supplement endogenous PAF-AH activity and to inactivate pathological amounts of PAF in the mammal.

Therapeutic/pharmaceutical compositions contemplated by the invention include PAF-AH products and a physiologically acceptable diluent or carrier and may also include other agents having anti-inflammatory effects. Dosage amounts indicated would be sufficient to supplement endogenous PAF-AH activity and to inactivate pathological amounts of PAF. For general dosage considerations see Remmington's Pharmaceutical Sciences, 18th Edition, Mack Publishing Co., Easton, Pa. (1990). Dosages will vary between about 0.1 to about 1000 μg PAF-AH/kg body weight. Therapeutic compositions of the invention may be administered by various routes depending on the pathological condition to be treated. For example, administration may be by intraveneous, subcutaneous, oral, suppository, and/or pulmonary routes.

For pathological conditions of the lung, administration of PAF-AH by the pulmonary route is particularly indicated. Contemplated for use in pulmonary administration are a wide range of delivery devices including, for example, nebulizers, metered dose inhalers, and powder inhalers, which are standard in the art. Delivery of various proteins to the lungs and circulatory system by inhalation of aerosol formulations has been described in Adjei et al., Pharm. Res., 7(6): 565–569 (1990) (leuprolide acetate); Braquet et al., J. Cardio. Pharm., 13(Supp. 5): s. 143–146 (1989) (endothelin-1); Hubbard et al., Annals of Internal Medicine, III(3), 206–212 (1989) (α1-antitrypsin); Smith et al., J. Clin. Invest., 84: 1145–1146 (1989) (α-1-proteinase inhibitor);

Debs et al., J. Immunol., 140: 3482–3488 (1933) (recombinant gamma interferon and tumor necrosis factor alpha); Patent Cooperation Treaty (PCT) International Publication No. WO 94/20069 published Sep. 15, 1994 (recombinant pegylated granulocyte colony stimulating factor).

BRIEF DESCRIPTION OF THE DRAWING

Numerous other aspects and advantages of the present invention will be apparent upon consideration of the following detailed description thereof, reference being made to the drawing wherein.

DETAILED DESCRIPTION

Figure 1:
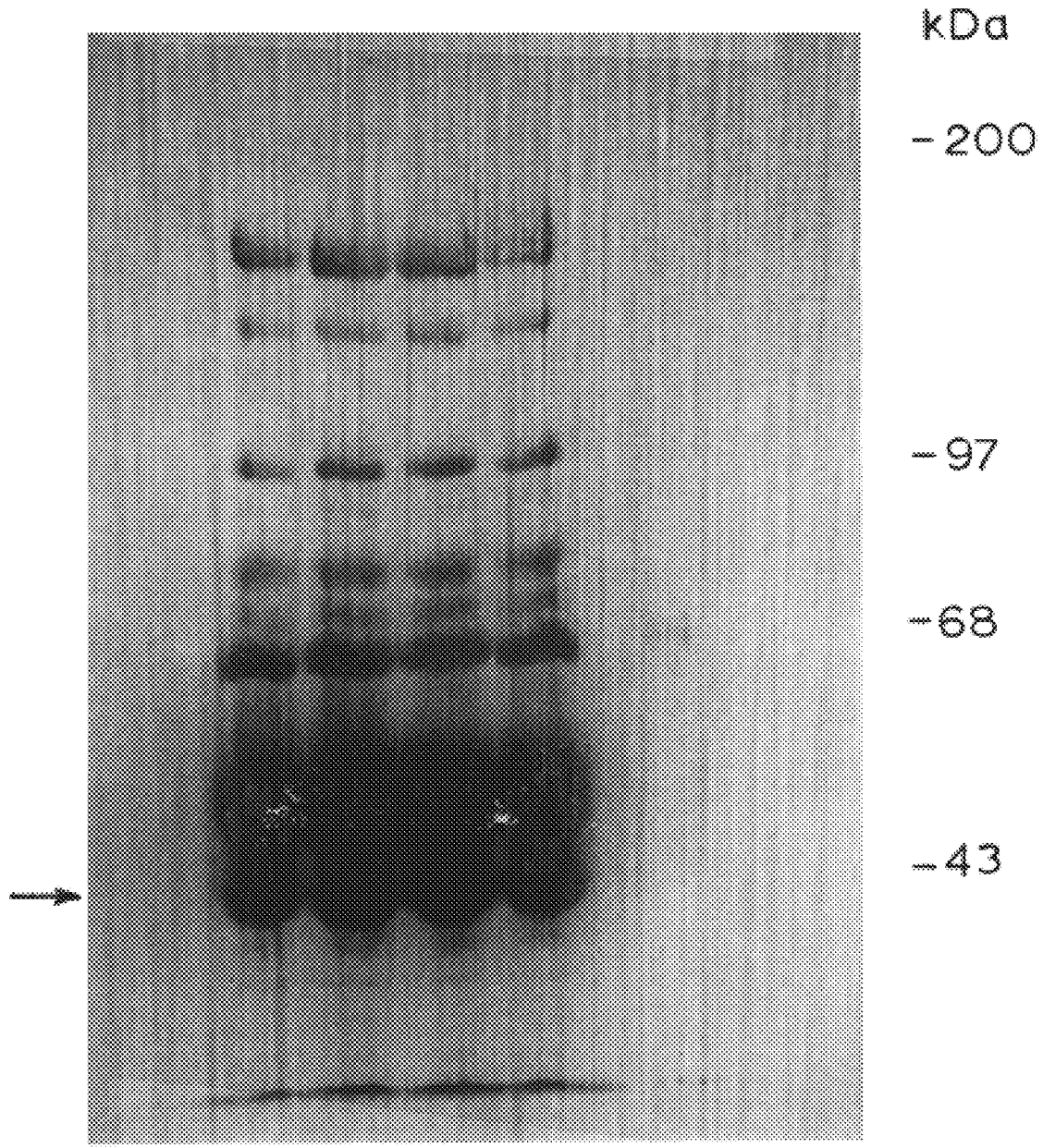
FIG. 1 is a photograph of a PVDF membrane containing PAF-AH purified from human plasma.

The following examples illustrate the invention. Example 1 presents a novel method for the purification of PAF-AH from human plasma. Example 2 describes amino acid microsequencing of the purified human plasma PAF-AH. The cloning of a full length cDNA encoding human plasma PAF-AH is described in Example 3. Identification of a putative splice variant of the human plasma PAF-AH gene is described in Example 4. The cloning of genomic sequences encoding human plasma PAF-AH is described in Example 5. Example 6 describes the cloning of canine, murine, bovine, chicken, rodent and macaque cDNAs homologous to the human plasma PAF-AH cDNA. Example 7 presents the results of an assay evidencing the enzymatic activity of recombinant PAF-AH transiently expressed in COS 7 cells. Example 8 describes the expression of full length, truncated and chimeric human PAF-AH DNAs in E. coli, S. cerevisiae and mammalian cells. Example 9 presents protocols for purification of recombinant PAF-AH from E. coli and assays confirming its enzymatic activity. Example 10 describes various recombinant PAF-AH products including amino acid substitution analogs and amino and carboxy-truncated products, and describes experiments demonstrating that native PAF-AH isolated from plasma is glycosylated. Results of a Northern blot assay for expression of human plasma PAF-AH RNA in various tissues and cell lines are presented in Example 11 while results of in situ hybridization are presented in Example 12. Example 13 describes the development of monoclonal and polyclonal antibodies specific for human plasma PAF-AH. Examples 14, 15, 16, 17, 18 and 19 respectively describe the in vivo therapeutic effect of administration of recombinant PAF-AH products of the invention on acute inflammation, pleurisy, asthma, necrotizing enterocolitis, adult respiratory distress syndrome and pancreatitis in animal models. Example 20 describes the in vitro effect of recombinant PAF-AH product on neurotoxicity associated with HIV infection. Example 21 presents the results of immunoassays of serum of human patients exhibiting a deficiency in PAF-AH activity and describes the identification of a genetic lesion in the patients which is apparently responsible for the deficiency.

EXAMPLE 1

PAF-AH was purified from human plasma in order to provide material for amino acid sequencing.

A. Optimization of Purification Conditions

Initially, low density lipoprotein (LDL) particles were precipitated from plasma with phosphotungstate and solubilized in 0.1% Tween 20 and subjected to chromatography on a DEAE column (Pharmacia, Uppsala, Sweden) according to the method of Stafforini et al. (1987), supra, but inconsistent elution of PAF-AH activity from the DEAE column required reevaluation of the solubilization and subsequent purification conditions.

Tween 20, CHAPS (Pierce Chemical Co., Rockford, Ill.) and octyl glucoside were evaluated by centrifugation and gel filtration chromatography for their ability to solubilize LDL particles. CHAPS provided 25% greater recovery of solubilized activity than Tween 20 and 300% greater recovery than octyl glucoside. LDL precipitate solubilized with 10 mM CHAPS was then fractionated on a DEAE Sepharose Fast Flow column (an anion exchange column; Pharmacia) with buffer containing 1 mM CHAPS to provide a large pool of partially purified PAF-AH ("the DEAE pool") for evaluation of additional columns.

The DEAE pool was used as starting material to test a variety of chromatography columns for utility in further purifying the PAF-AH activity. The columns tested included: Blue Sepharose Fast Flow (Pharmacia), a dye ligand affinity column; S-Sepharose Fast Flow (Pharmacia), a cation exchange column; Cu Chelating Sepharose (Pharmacia), a metal ligand affinity column; Fractogel S (EM Separations, Gibbstown, N.J.), a cation exchange column; and Sephacryl-200 (Pharmacia), a gel filtration column. These chromatographic procedures all yielded low, unsatisfactory levels of purification when operated in 1 mM CHAPS. Subsequent gel filtration chromatography on Sephacryl S-200 in 1 mM CHAPS generated an enzymatically active fraction which eluted over a broad size range rather than the expected 44 kDa approximate size. Taken together, these results indicated that the LDL proteins were aggregating in solution.

Different LDL samples were therefore evaluated by analytical gel filtration chromatography for aggregation of the PAF-AH activity. Samples from the DEAE pool and of freshly solubilized LDL precipitate were analyzed on Superose 12 (Pharmacia) equilibrated in buffer with 1 mM CHAPS. Both samples eluted over a very broad range of molecular weights with most of the activity eluting above 150 kDa. When the samples were then analyzed on Superose 12 equilibrated with 10 mM CHAPS, the bulk of the activity eluted near 44 kDa as expected for PAF-AH activity. However, the samples contained some PAF-AH activity in the high molecular weight region corresponding to aggregates.

Other samples eluted PAF-AH activity exclusively in the approximately 44 kDa range when they were subsequently tested by gel filtration. These samples were an LDL precipitate solubilized in 10 mM CHAPS in the presence of 0.5M NaCl and a fresh DEAE pool that was adjusted to 10 mM CHAPS after elution from the DEAE column. These data indicate that at least 10 mM CHAPS is required to maintain non-aggregated PAF-AH. Increase of the CHAPS concentration from 1 mM to 10 mM after chromatography on DEAE but prior to subsequent chromatographic steps resulted in dramatic differences in purification. For example, the degree of PAF-AH purification on S-Sepharose Fast Flow was increased from 2-fold to 10-fold. PAF-AH activity bound the Blue Sepharose Fast Flow column irreversibly in 1 mM CHAPS, but the column provided the highest level of purification in 10 mM CHAPS. The DEAE chromatography was not improved with prior addition of 10 mM CHAPS.

Chromatography on Cu Chelating Sepharose after the Blue Sepharose Fast Flow column concentrated PAF-AH activity 15-fold. It was also determined that PAF-AH activity could be recovered from a reduced SDS-polyacrylamide gel, as long as samples were not boiled. The activity of material eluted from the Cu Chelating Sepharose column when subjected to SDS-polyacrylamide gel electrophoresis coincided with a major protein band when the gel was silver stained.

B. PAF-AH Purification Protocol

The novel protocol utilized to purify PAF-AH for amino acid sequencing therefore comprised the following steps which were performed at 4° C. Human plasma was divided into 900 ml aliquots in 1 liter Nalgene bottles and adjusted to pH 8.6. LDL particles were then precipitated by adding 90 ml of 3.85% sodium phosphotungstate followed by 23 ml of 2M MgCl$_2$. The plasma was then centrifuged for 15 minutes at 3600 g. Pellets were resuspended in 800 ml of 0.2% sodium citrate. LDL was precipitated again by adding 10 g NaCl and 24 ml of 2M MgCl$_2$. LDL particles were pelleted by centrifugation for 15 minutes at 3600 g. This wash was repeated twice. Pellets were then frozen at −20° C. LDL particles from 5 L of plasma were resuspended in 5 L of buffer A (25 mM Tris-HCl, 10 mM CHAPS, pH 7.5) and stirred overnight. Solubilized LDL particles were centrifuged at 3600 g for 1.5 hours. Supernatants were combined and filtered with Whatman 113 filter paper to remove any remaining solids. Solubilized LDL supernatant was loaded on a DEAE Sepharose Fast Flow column (11 cm×10 cm; 1 L resin volume; 80 ml/minute) equilibrated in buffer B (25 mM Tris-HCl, 1 mM CHAPS, pH 7.5). The column was washed with buffer B until absorbance returned to baseline. Protein was eluted with an 8 L, 0–0.5M NaCl gradient and 480 ml fractions were collected. This step was necessary to obtain binding to the Blue Sepharose Fast Flow column below. Fractions were assayed for acetylhydrolase activity essentially by the method described in Example 4.

Active fractions were pooled and sufficient CHAPS was added to make the pool about 10 mM CHAPS. The DEAE pool was loaded overnight at 4 ml/minute onto a Blue Sepharose Fast Flow column (5 cm×10 cm; 200 ml bed volume) equilibrated in buffer A containing 0.5M NaCl. The column was washed with the equilibration buffer at 16 ml/minute until absorbance returned to baseline. PAF-AH activity was step eluted with buffer A containing 0.5M KSCN (a chaotropic salt) at 16 ml/minute and collected in 50 ml fractions. This step resulted in greater than 1000-fold purification. Active fractions were pooled, and the pool was adjusted to pH 8.0 with 1M Tris-HCl pH 8.0. The active pool from Blue Sepharose Fast Flow chromatography was loaded onto a Cu Chelating Sepharose column (2.5 cm×2 cm; 10 ml bed volume; 4 ml/minute) equilibrated in buffer C [25 mM Tris-HCl, 10 mM CHAPS, 0.5M NaCl, pH 8.0 (pH 7.5 also worked)], and the column was washed with 50 ml buffer C. PAF-AH activity was eluted with 100 ml 50 mM imidazole in buffer C and collected in 10 ml fractions. Fractions containing PAF-AH activity were pooled and dialyzed against buffer A. In addition to providing a 15-fold concentration of PAF-AH activity, the Cu Chelating Sepharose column gave a small purification. The Cu Chelating Sepharose pool was reduced in 50 mM DTT for 15 minutes at 37° C. and loaded onto a 0.75 mm, 7.5% polyacrylamide gel. Gel slices were cut every 0.5 cm and placed in disposable microfuge tubes containing 200 μl 25 mM Tris-HCl, 10 mM CHAPS, 150 mM NaCl. Slices were ground up and allowed to incubate overnight at 4° C. The supernatant of each gel slice was then assayed for PAF-AH activity to determine which protein band on SDS-PAGE contained PAF-AH activity. PAF-AH activity was found in an approximately 44 kDa band. Protein from a duplicate gel was electrotransferred to a PVDF membrane (Immobilon-P, Millipore) and stained with Coomassie Blue. A photograph of the PVDF membrane is presented in FIG. 1.

As presented in Table 1 below, approximately 200 μg PAF-AH was purified $2 \times 10^6$-fold from 5 L human plasma. In comparison, a $3 \times 10^4$-fold purification of PAF-AH activity is described in Stafforini et al. (1987), supra.

membrane containing the approximately 44 kDa band was cut in half such that the upper part and the lower part of the membrane were separately subjected to sequencing.

The N-terminal sequence obtained for the lower half of the membrane was:

SEQ ID NO: 1
F K D L G E E N F K A L V L I A F

A search of protein databases revealed this sequence to be a fragment of human serum albumin. The upper half of the same PVDF membrane was also sequenced and the N-terminal amino acid sequence determined was:

SEQ ID NO: 2
I Q V L M A A A S F G Q T K I P

This sequence did not match any protein in the databases searched and was different from the N-terminal amino acid sequence:

SEQ ID NO: 3
M K P L V V F V L G G which was reported for erythrocyte cytoplasmic PAF-AH in Stafforini et al. (1993), supra. The novel sequence (SEQ ID NO: 2) was utilized for cDNA cloning of human plasma PAF-AH as described below in Example 3.

EXAMPLE 3

A full length clone encoding human plasma PAF-AH was isolated from a macrophage cDNA library.

TABLE 1

| Sample | Vol. (ml) | Activity (cpm × $10^6$) | Total Activity (cpm × $10^9$) | Prot. Conc. (mg/ml) | Specific Activity (cpm × $10^6$) | % Recovery of Activity | | Fold Purification | |
|---|---|---|---|---|---|---|---|---|---|
| | | | | | | Step | Cum. | Step | Cum. |
| Plasma | 5000 | 23 | 116 | 62 | 0.37 | 100 | 100 | 1 | 1 |
| LDL | 4500 | 22 | 97 | 1.76 | 12 | 84 | 84 | 33 | 33 |
| DEAE | 4200 | 49 | 207 | 1.08 | 46 | 212 | 178 | 3.7 | 124 |
| Blue | 165 | 881 | 14 | 0.02 | 54200 | 70 | 126 | 1190 | $1.5 \times 10^5$ |
| Cu | 12 | 12700 | 152 | 0.15 | 82200 | 104 | 131 | 1.5 | $2.2 \times 10^5$ |
| SDS-PAGE | — | — | — | — | — | — | — | ~10 | $2.2 \times 10^6$ |

In summary, the following steps were unique and critical for successful purification of plasma PAF-AH for microsequencing: (1) solubilization and chromatography in 10 mM CHAPS, (2) chromatography on a blue ligand affinity column such as Blue Sepharose Fast Flow. (3) chromatography on a Cu ligand affinity column such as Cu Chelating Sepharose, and (4) elution of PAF-AH from SDS-PAGE.

EXAMPLE 2

For amino acid sequencing, the approximately 44 kDa protein band from the PAF-AH-containing PVDF membrane described in Example 1 was excised and sequenced using an Applied Biosystems 473A Protein sequencer. N-terminal sequence analysis of the approximately 44 kDa protein band corresponding to the PAF-AH activity indicated that the band contained two major sequences and two minor sequences. The ratio of the two major sequences was 1:1 and it was therefore difficult to interpret the sequence data.

To distinguish the sequences of the two major proteins which had been resolved on the SDS gel, a duplicate PVDF A. Construction of a Macrophage cDNA Library Poly $A^+$ RNA was harvested from peripheral blood monocyte-derived macrophages. Double-stranded, blunt-ended cDNA was generated using the Invitrogen Copy Kit (San Diego, Calif.) and BstXI adapters were ligated to the cDNA prior to insertion into the mammalian expression vector, pRc/CMV (Invitrogen). The resulting plasmids were introduced into E. coli strain XL-1 Blue by electroporation. Transformed bacteria were plated at a density of approximately 3000 colonies per agarose plate on a total of 978 plates. Plasmid DNA prepared separately from each plate was retained in individual pools and was also combined into larger pools representing 300,000 clones each.

B. Library Screening by PCR

The macrophage library was screened by the polymerase chain reaction utilizing a degenerate antisense oligonucleotide PCR primer based on the novel N-terminal amino acid sequence described in Example 2. The sequence of the primer is set out below in IUPAC nomenclature and where "I" is an inosine.

```
SEQ ID NO: 4
5' ACATGAATTCGGIATCYTTIGTYTGICCRAA 3'
```

The codon choice tables of Wada et al., *Nuc. Acids Res.*, 19S: 1981–1986 (1991) were used to select nucleotides at the third position of each codon of the primer. The primer was used in combination with a primer specific for either the SP6 or T7 promoter sequences, both of which flank the cloning site of pRc/CMV, to screen the macrophage library pools of 300,000 clones. All PCR reactions contained 100 ng of template cDNA, 1 μg of each primer, 0.125 mM of each dNTP, 10 mM Tris-HCl pH 8.4, 50 mM MgCl$_2$ and 2.5 units of Taq polymerase. An initial denaturation step of 94° C. for four minutes was followed by 30 cycles of amplification of 1 minute at 94° C., 1 minute at 60° C. and 2 minutes at 72° C. The resulting PCR product was cloned into pBluescript SK$^-$ (Stratagene, La Jolla, Calif.) and its nucleotide sequence determined by the dideoxy chain termination method. The PCR product contained the sequence predicted by the novel peptide sequence and corresponds to nucleotides 1 to 331 of SEQ ID NO: 7.

The PCR primers set out below, which are specific for the cloned PCR fragment described above, were then designed for identifying a full length clone.

```
Sense Primer (SEQ ID NO: 5)
5' TATTTCTAGAAGTGTGGTGGAACTCGCTGG 3'
Antisense Primer (SEQ ID NO: 6)
5' CGATGAATTCAGCTTGCAGCAGCCATCAGTAC 3'
```

PCR reactions utilizing the primers were performed as described above to first screen the cDNA pools of 300,000 clones and then the appropriate subset of the smaller pools of 3000 clones. Three pools of 3000 clones which produced a PCR product of the expected size were then used to transform bacteria.

C. Library Screening by Hybridization

DNA from the transformed bacteria was subsequently screened by hybridization using the original cloned PCR fragment as a probe. Colonies were blotted onto nitrocellulose and prehybridized and hybridized in 50% formamide, 0.75M sodium chloride, 0.075M sodium citrate, 0.05M sodium phosphate pH 6.5, 1% polyvinyl pyrolidine, 1% Ficoll, 1% bovine serum albumin and 50 ng/ml sonicated salmon sperm DNA. The hybridization probe was labeled by random hexamer priming. After overnight hybridization at 42° C., blots were washed extensively in 0.03M sodium chloride, 3 mM sodium citrate, 0.1% SDS at 42° C. The nucleotide sequence of 10 hybridizing clones was determined. One of the clones, clone sAH 406-3, contained the sequence predicted by the original peptide sequence of the PAF-AH activity purified from human plasma. The DNA and deduced amino acid sequences of the human plasma PAF-AH are set out in SEQ ID NOs: 7 and 8, respectively.

Clone sAH 406-3 contains a 1.52 kb insert with an open reading frame that encodes a predicted protein of 441 amino acids. At the amino terminus, a relatively hydrophobic segment of 41 residues precedes the N-terminal amino acid (the isoleucine at position 42 of SEQ ID NO: 8) identified by protein microsequencing. The encoded protein may thus have either a long signal sequence or a signal sequence plus an additional peptide that is cleaved to yield the mature functional enzyme. The presence of a signal sequence is one characteristic of secreted proteins. In addition, the protein encoded by clone sAH 406-3 includes the consensus GxSxG motif (amino acids 271–275 of SEQ ID NO: 8) that is believed to contain the active site serine of all known mammalian lipases, microbial lipases and serine proteases. See Chapus et al., *Biochimie*, 70: 1223–1224 (1988) and Brenner, *Nature*, 334: 528–530 (1988).

Table 2 below is a comparison of the amino acid composition of the human plasma PAF-AH of the invention as predicted from SEQ ID NO: 8 and the amino acid composition of the purportedly purified material described by Stafforini et al. (1987), supra.

TABLE 2

|           | Clone sAH 406-3 | Stafforini et al. |
|-----------|-----------------|-------------------|
| Ala       | 26              | 24                |
| Asp & Asn | 48              | 37                |
| Cys       | 5               | 14                |
| Glu & Gln | 36              | 42                |
| Phe       | 22              | 12                |
| Gly       | 29              | 58                |
| His       | 13              | 24                |
| Ile       | 31              | 17                |
| Lys       | 26              | 50                |
| Leu       | 40              | 26                |
| Met       | 10              | 7                 |
| Pro       | 15              | 11                |
| Arg       | 18              | 16                |
| Ser       | 27              | 36                |
| Thr       | 20              | 15                |
| Val       | 13              | 14                |
| Trp       | 7               | Not determined    |
| Tyr       | 14              | 13                |

The amino acid composition of the mature form of the human plasma PAF-AH of the invention and the amino acid composition of the previously purified material that was purportedly the human plasma PAF-AH are clearly distinct.

When alignment of the Hattori et al., supra nucleotide and deduced amino acid sequences of bovine brain cytoplasmic PAF-AH with the nucleotide and amino acid sequences of the human plasma PAF-AH of the invention was attempted, no significant structural similarity in the sequences was observed.

EXAMPLE 4

A putative splice variant of the human PAF-AH gene was detected when PCR was performed on macrophage and stimulated PBMC cDNA using primers that hybridized to the 5' untranslated region (nucleotides 31 to 52 of SEQ ID NO: 7) and the region spanning the translation termination codon at the 3' end of the PAF-AH cDNA (nucleotides 1465 to 1487 of SEQ ID NO: 7). The PCR reactions yielded two bands on a gel, one corresponding to the expected size of the PAF-AH cDNA of Example 3 and the other was about 100 bp shorter. Sequencing of both bands revealed that the larger band was the PAF-AH cDNA of Example 3 while the shorter band lacked exon 2 (Example 5 below) of the PAF-AH sequence which encodes the putative signal and pro-peptide sequences of plasma PAF-AH. The predicted catalytic triad and all cysteines were present in the shorter clone, therefore the biochemical activity of the protein encoded by the clone is likely to match that of the plasma enzyme.

To begin to assess the biological relevance of the PAF-AH splice variant that is predicted to encode a cytoplasmically active enzyme, the relative abundance of the two forms in blood monocyte-derived macrophages was assayed by RNase protection. Neither message was present in freshly isolated monocytes but both messages were found at day 2 of in vitro differentiation of the monocytes into macrophages and persisted through 6 days of culture. The quantity of the two messages was approximately equivalent throughout the differentiation period. In contrast, similar analyses of neural tissues revealed that only full length message predicted to encode the full length extracellular form of PAF-AH is expressed.

EXAMPLE 5

Genomic human plasma PAF-AH sequences were also isolated. The structure of the PAF-AH gene was determined by isolating lambda and P1 phage clones containing human genomic DNA by DNA hybridization under conditions of high stringency. Fragments of the phage clones were subcloned and sequenced using primers designed to anneal at regular intervals throughout the cDNA clone sAH 406-3. In addition, new sequencing primers designed to anneal to the intron regions flanking the exons were used to sequence back across the exon-intron boundaries to confirm the sequences. Exon/intron boundaries were defined as the points where the genomic and cDNA sequences diverged. These analyses revealed that the human PAF-AH gene is comprised of 12 exons.

Exons 1, 2, 3, 4, 5, 6, and part of 7 were isolated from a male fetal placental library constructed in lamda FIX (Stratagene). Phage plaques were blotted onto nitrocellulose and prehybridized and hybridized in 50% formamide, 0.75M sodium chloride, 75 mM sodium citrate, 50 mM sodium phosphate (pH 6.5), 1% polyvinyl pyrolidine, 1% Ficoll, 1% bovine serum albumin., and 50 ng/ml sonicated salmon sperm DNA. The hybridization probe used to identify a phage clone containing exons 2–6 and part of 7 consisted of the entire cDNA clone sAH 406-3. A clone containing exon 1 was identified using a fragment derived from the 5' end of the cDNA clone (nucleotides 1 to 312 of SEQ ID NO: 7). Both probes were labelled with $^{32}$P by hexamer random priming. After overnight hybridization at 42° C., blots were washed extensively in 30 mM sodium chloride, 3 mM sodium citrate, 0.1% SDS at 42° C. The DNA sequences of exons 1, 2, 3, 4, 5, and 6 along with partial surrounding intron sequences are set out in SEQ ID NOs: 9, 10, 11, 12, 13, and 14, respectively.

The remainder of exon 7 as well as exons 8, 9, 10, 11, and 12 were subcloned from a P1 clone isolated from a human P1 genomic library. P1 phage plaques were blotted onto nitrocellulose and prehybridized and hybridized in 0.75M sodium chloride, 50 mM sodium phosphate (pH 7.4), 5 mM EDTA, 1% polyvinyl pyrolidine, 1% Ficoll, 1% bovine serum albumin, 0.5% SDS, and 0.1 mg/ml total human DNA. The hybridization probe, labeled with $^{32}$P by hexamer random priming, consisted of a 2.6 kb EcoR1 fragment of genomic DNA derived from the 3' end of a lambda clone isolated above. This fragment contained exon 6 and the part of exon 7 present on the phage clone. After overnight hybridization at 65° C., blots were washed as described above. The DNA sequences of exons 7, 8, 9, 10, 11, and 12 along with partial surrounding intron sequences are set out in SEQ ID NOs: 15, 16, 17, 18, 19, and 20, respectively.

EXAMPLE 6

Full length plasma PAF-AH cDNA clones were isolated from mouse, canine, bovine and chicken spleen cDNA libraries and a partial rodent clone was isolated from a rat thymus cDNA library. The clones were identified by low stringency hybridization to the human cDNA (hybridization conditions were the same as described for exons 1 through 6 in Example 5 above except that 20% formamide instead of 50% form amide was used). A 1 kb HindIII fragment of the human PAF-AH sAH 406-3 cDNA clone (nucleotides 309 to 1322 of SEQ ID NO: 7) was used as a probe. In addition, a partial monkey clone was isolated from macaque brain cDNA by PCR using primers based on nucleotides 285 to 303 and 851 to 867 of SEQ ID NO: 7. The nucleotide and deduced amino acid sequences of the mouse, canine, bovine, chicken, rat, and macaque cDNA clones are set out in SEQ ID NOs: 21, 22, 23, 24, 25, and 26, respectively.

A comparison of the deduced amino acid sequences of the cDNA clones with the human cDNA clone results in the amino acid percentage identity values set out in Table 3 below.

TABLE 3

|        | Human | Dog | Mouse | Bovine | Chicken |
|--------|-------|-----|-------|--------|---------|
| Dog    | 80    | 100 | 64    | 82     | 50      |
| Mouse  | 66    | 64  | 100   | 64     | 47      |
| Monkey | 92    | 82  | 69    | 80     | 52      |
| Rat    | 74    | 69  | 82    | 69     | 55      |
| Bovine | 82    | 82  | 64    | 100    | 50      |
| Chicken| 50    | 50  | 47    | 50     | 100     |

About 38% of the residues are completely conserved in all the sequences. The most divergent regions are at the amino terminal end (containing the signal sequence) and the carboxyl terminal end which are shown in Example 10 as not critical for enzymatic activity. The Gly-Xaa-Ser-Xaa-Gly motif (SEQ ID NO: 27) found in neutral lipases and other esterases was conserved in the bovine, canine, mouse, rat and chicken PAF-AH. The central serine of this motif serves as the active site nucleophile for these enzymes. The predicted aspartate and histidine components of the active site (Example 10A) were also conserved. The human plasma PAF-AH of the invention therefore appears to utilize a catalytic triad and may assume the $\alpha/\beta$ hydrolase conformation of the neutral lipases even though it does not exhibit other sequence homology to the lipases.

Moreover, human plasma PAF-AH is expected to have a region that mediates its specific interaction with the low density and high density lipoprotein particles of plasma. Interaction with these particles may be mediated by the N-terminal half of the molecule which has large stretches of amino acids highly conserved among species but does not contain the catalytic triad of the enzyme.

EXAMPLE 7

To determine whether human plasma PAF-AH cDNA clone sAH 406-3 (Example 3) encodes a protein having PAF-AH activity, the pRc/CMV expression construct was transiently expressed in COS 7 cells. Three days following transfection by a DEAE Dextran method, COS cell media was assayed for PAF-AH activity.

Cells were seeded at a density of 300,000 cells per 60 mm tissue culture dish. The following day, the cells were incubated in DMEM containing 0.5 mg/ml DEAE dextran, 0.1 mM chloroquine and 5–10 μg of plasmid DNA for 2 hours. Cells were then treated with 10% DMSO in phosphate-buffered saline for 1 minute, washed with media and incubated in DMEM containing 10% fetal calf serum previously treated with diisopropyl fluorophosphate (DFP) to inactivate endogenous bovine serum PAF-AH. After 3 days of incubation, media from transfected cells were assayed for PAF-AH activity. Assays were conducted in the presence and absence of either 10 mM EDTA or 1 mM DFP to determine whether the recombinant enzyme was calcium-independent and inhibited by the serine esterase inhibitor DFP as previously described for plasma PAF-AH by Stafforini et al. (1987), supra. Negative controls included cells transfected with pRc/CMV either lacking an insert or having the sAH 406-3 insert in reverse orientation.

PAF-AH activity in transfectant supernatants was determined by the method of Stafforini et al. (1990), supra, with the following modifications. Briefly, PAF-AH activity was determined by measuring the hydrolysis of $^3$H-acetate from [acetyl-$^3$H] PAF (New England Nuclear, Boston, Mass.). The aqueous free $^3$H-acetate was separated from labeled substrate by reversed-phase column chromatography over octadecylsilica gel cartridges (Baker Research Products, Phillipsburg, Pa.). Assays were carried out using 10 µl transfectant supernatant in 0. 1M Hepes buffer, pH 7.2, in a reaction volume of 50 µl. A total of 50 pmoles of substrate were used per reaction with a ratio of 1:5 labeled: cold PAF. Reactions were incubated for 30 minutes at 37° C. and stopped by the addition of 40 µl of 10M acetic acid. The solution was then washed through the octadecylsilica gel cartridges which were then rinsed with 0.1M sodium acetate. The aqueous eluate from each sample was collected and counted in a liquid scintillation counter for one minute. Enzyme activity was expressed in counts per minute.

Figure 2:
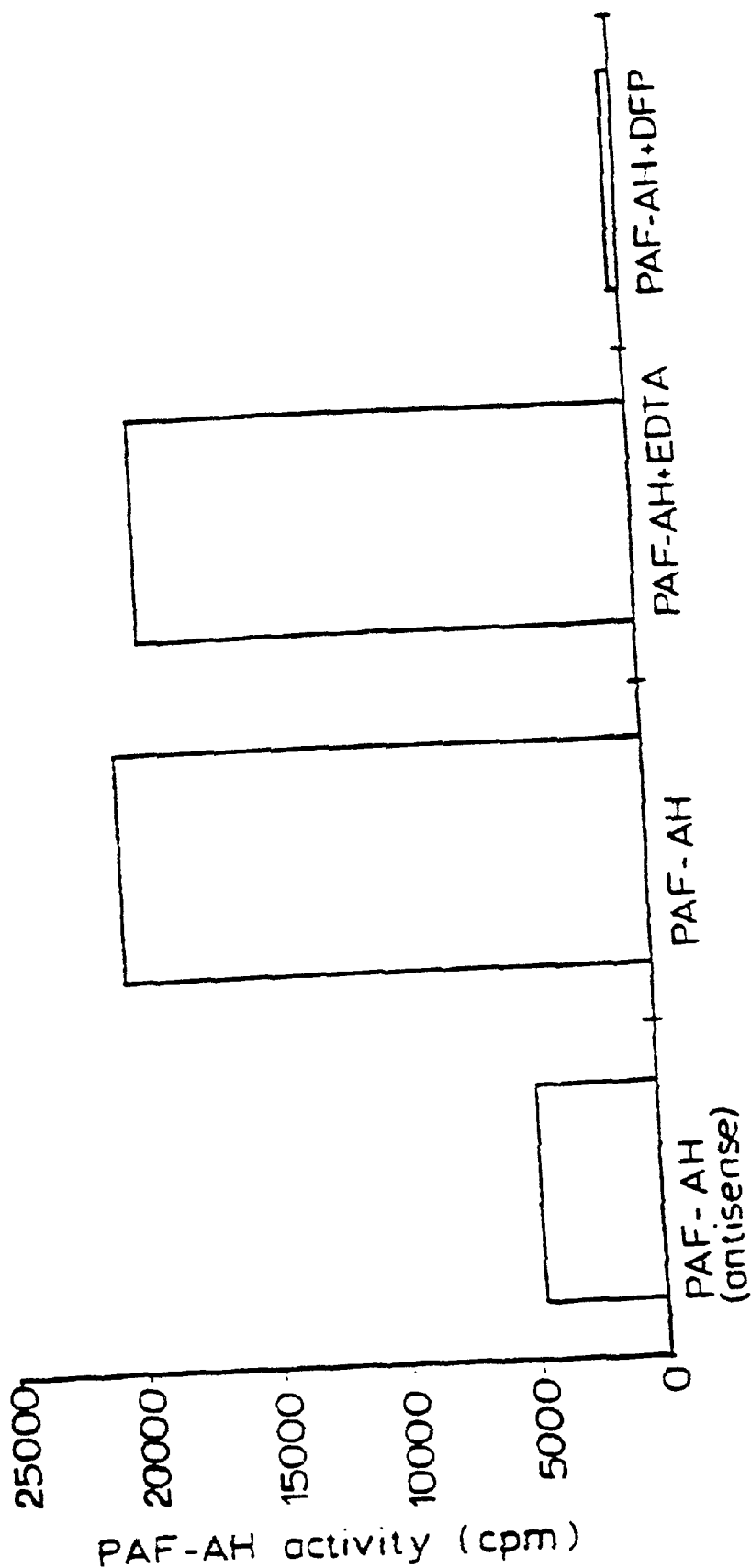
FIG. 2 is a graph showing the enzymatic activity of recombinant human plasma PAF-AH.

As shown in FIG. 2, media from cells transfected with sAH 406-3 contained PAF-AH activity at levels 4-fold greater than background. This activity was unaffected by the presence of EDTA but was abolished by 1 mM DFP. These observations demonstrate that clone sAH 406-3 encodes an activity consistent with the human plasma enzyme PAF-AH.

EXAMPLE 8

Full length and various truncated human plasma PAF-AH DNAs and a chimeric mouse-human PAF-AH DNA were expressed in E. coli and yeast and stably expressed in mammalian cells by recombinant methods.

A. Expression in E. coli

PCR was used to generate a protein coding fragment of human plasma PAF-AH cDNA from clone sAH 406-3 which was readily amenable to subcloning into an E. coli expression vector. The subcloned segment began at the 5' end of the human gene with the codon that encodes $Ile_{42}$ (SEQ ID NO: 8), the N-terminal residue of the enzyme purified from human plasma. The remainder of the gene through the native termination codon was included in the construct. The 5' sense PCR primer utilized was:

SEQ ID NO: 28
5TATTCTAGAATT<u>ATG</u>ATACAAGTATTAATGGCTGCTGCAAG

3' and contained an XbaI cloning site as well as a translation initiation codon (underscored). The 3' antisense primer utilized was:

SEQ ID NO: 29
5' ATTGATATCCTAATTGTATTTCTCTATTCCTG 3' and encompassed the termination codon of sAH 406-3 and contained an EcoRV cloning site. PCR reactions were performed essentially as described in Example 3. The resulting PCR product was digested with XbaI and EcoRV and subcloned into a pBR322 vector containing the Trp promoter [deBoer et al., PNAS, 80:21–25 (1983)] immediately upstream of the cloning site. E. coli strain XL-1 Blue was transformed with the expression construct, and cultured in L broth containing 100 µg/ml of carbenicillin. Transformants from overnight cultures were pelleted and resuspended in lysis buffer containing 50 mM Tris-HCl pH 7.5, 50 mM NaCl, 10 mM CHAPS, 1 mM EDTA, 100 µg/ml lysozyme, and 0.05 trypsin-inhibiting units (TIU)/ml Aprotinin. Following a 1 hour incubation on ice and sonication for 2 minutes, the lysates were assayed for PAF-AH activity by the method described in Example 4. E. coli transformed with the expression construct (designated trp AH) generated a product with PAF-AH activity. See Table 6 in Example 9.

Constructs including three additional promoters, the tacII promoter (deBoer, supra), the arabinose (ara) B promoter from Salmonella typhimurium [Horwitz et al., Gene, 14: 309–319 (1981)], and the bacteriophage T7 promoter, were also utilized to drive expression of human PAF-AH sequences in E. coli. Constructs comprising the Trp promoter (pUC trp AH), the tacII promoter (pUC tac AH), and the araB promoter (pUC ara AH) were assembled in plasmid pUC19 (New England Biolabs, Mass.) while the construct comprising the T7 promoter (pET AH) was assembled in plasmid pTE15B (Novagen, Madison, Wis.). A construct containing a hybrid promoter, pHAB/PH, consisting of the araB promoter fused to the ribosome binding sites of the T7 promoter region was also assembled in pET15B. All E. coli constructs produced PAF-AH activity within a range of 20 to 50 U/ml/OD$_{600}$. This activity corresponded to a total recombinant protein mass of $\geq$1% of the total cell protein.

Several E. coli expression constructs were also evaluated which produce PAF-AH with extended amino termini. The N-terminus of natural plasma PAF-AH was identified as $Ile_{42}$ by amino acid sequencing (Example 2). However, the sequence immediately upstream of $Ile_{42}$ does not conform to amino acids found at signal sequence cleavage sites [i.e., the "–3-1-rule" is not followed, as lysine is not found at position –1; see von Heijne, Nuc. Acids Res., 14:4683–4690 (1986)]. Presumably a more classical signal sequence ($M_1$-$A_{17}$ or $M_1$-$P_{21}$) is recognized by the cellular secretion system, followed by endoproteolytic cleavage. The entire coding sequence for PAF-AH beginning at the initiating methionine (nucleotides 162 to 1487 of SEQ ID NO: 7) was engineered for expression in E. coli using the trp promoter. As shown in Table 4. this construct made active PAF-AH, but expression was at about one fiftieth of the level of the original construct beginning at $Ile_{42}$. Another expression construct, beginning at $Val_{18}$ (nucleotides 213 to 1487 of SEQ ID NO: 7), produced active PAF-AH at about one third the level of the original construct. These results suggest that amino terminal end extensions are not critical or necessary for activity of recombinant PAF-AH produced in E. coli.

TABLE 4

| | PAF-AH activity (U/ml/OD$_{600}$) | |
|---|---|---|
| Construct | Lysate | Media |
| pUC trp AH (Ile$_{42}$ N-terminus) | 177.7 | 0.030 |
| pUC trp AH Met$_1$ | 3.1 | 0.003 |
| pUC trp AH Val$_{18}$ | 54.6 | 0.033 |

Truncated recombinant human PAF-AH products were also produced in E. coli using a low copy number plasmid and a promoter that can be induced by the addition of ambinose to the culture. One such N-terminally truncated PAF-AH product is the recombinant expression product of DNA encoding amino acid residues Met$_{46}$ through Asn$_{441}$ of the polypeptide encoded by full length PAF-AH cDNA (SEQ ID NO: 8), and is designated rPH.2. The plasmid used for production of rPH.2 in bacterial cells was pBAR2/PH.2, a pBR322-based plasmid that carries (1) nucleotides 297 to 1487 of SEQ ID NO: 7 encoding human PAF-AH beginning with the methionine codon at position 46, (2) the araB-C promoters and araC gene from the arabinose operon of *Salinonella typhimurium*, (3) a transcription termination sequence from the bacteriophage T7, and (4) a replication origin from bacteriophage f1.

Specifically, pBAR2/PH.2 included the following segments of DNA: (1) from the destroyed AatII site at position 1994 to the EcoRI site at nucleotide 6274, vector sequence containing an origin of replication and genes encoding resistance to either ampicillin or tetracycline derived from the bacterial plasmid pBR322; (2) from the EcoRI site at position 6274 to the XbaI site at position 131, DNA from the *Salmonella typhimurium* arabinose operon (Genbank accession numbers M11045, M11046, M11047, J01797); (3) from the XbaI site at position 131 to the NcoI site at position 170, DNA containing a ribosome binding site from pET-21b (Novagen, Madison, Wis.); (4) from the NcoI site at position 170 to the XhoI site at position 1363, human PAF-AH cDNA sequence; and (5) from the XhoI site at position 1363 to the destroyed AatII site at position 1993, a DNA fragment from pET-21b (Novagen) that contains a transcription termination sequence from bacteriophae T7 and an origin of replication from bacteriophage f1.

Another PAF-AH product, designated rPH.9, is the recombinant expression product of DNA encoding amino acid residues $Met_{46}$ through $Ile_{429}$ of the polypeptide encoded by full length PAF-AH cDNA (SEQ ID NO: 8). The DNA encoding rPH.9 was inserted into the same vector used for production of rPH.2 in bacterial cells. This plasmid was designated pBAR2/PH.9 and specifically included the following segments of DNA: (1) from the destroyed AatII site at position 1958 to the EcoRI site at nucleotide 6239 of the vector sequence containing an origin of replication and genes encoding resistance to either ampicillin or tetracycline derived from the bacterial plasmid pBR322; (2) from the EcoRI site at position 6239 to the XbaI site at position 131, DNA from the *Salmonella typhimurium* arabinose operon (Genbank accession numbers M11045, M11046, M11047, J01797); (3) from the XbaI site at position 131 to the NcoI site at position 170, DNA containing a ribosome binding site from pET-21b (Novagen, Madison, Wis.); (4) from the NcoI site at position 170 to the XhoI site at position 1328, human PAF-AH DNA sequence; (5) from the XhoI site at position 1328 to the destroyed AatII site at position 1958, a DNA fragment from pET-21b (Novagen, Madison, Wis.) that contains a transcription termination sequence from bacteriophage T7 and a origin of replication from bacteriophage f1.

Expression of PAF-AH products in pBAR2/PH.2 and pBAR2/PH.9 is under the control of the araB promoter, which is tightly repressed in the presence of glucose and absence of arabinose, but functions as a strong promoter when L-arabinose is added to cultures depleted of glucose. Selection for cells containing the plasmid can be accomplished through the addition of either ampicillin (or related antibiotics) or tetracycline to the culture medium. A variety of *E. coli* strains can be used as a host for recombinant expression of PAF-AH products, including but not limited to strains prototrophic for arabinose metabolism such as W3110, DH5α, BL21, C600, JM101 and their derivatives, strains containing mutations reducing proteolysis such as CAG629, KY1429, and strains defective in their ability to degrade arabinose such as SB7219 and MC1061. The advantage of using a strain that is unable to break down arabinose is that the inducer (arabinose) for production of PAF-AH is not depleted from the medium during the induction period, resulting in higher levels of PAF-AH compared to that obtained with strains that are capable of metabolizing arabinose. Any suitable media and culturing conditions may be used to express active PAF-AH products in various *E. coli* strains. For example, either rich media formulations such as LB, EDM295 (a M9 based minimum medium supplemented with yeast extract and acid hydrolysed casein), or "defined" media such as A675, an A based minimal medium set at pH 6.75 employing glycerol as a carbon source and supplemented with trace elements and vitamins, permit substantial production of rPAF-AH products. Tetracycline is included in the media to maintain selection of the plasmid.

The plasmid pBAR2/PH.2 was transformed into the *E. coli* strain MC1061 (ATCC 53338), which carries a deletion of the arabinose operon and thereby cannot metabolize arabinose. MC1061 is also a leucine autograph and was cultivated by batch-fed process using a defined media containing casino acids that complement the leucine mutation.

The *E. coli* M1061 cells transformed with pBAR2/PH.2 were grown at 30° C. in batch media containing 2 gm/L glucose. Glucose serves the dual purpose of carbon source for cell growth, and repressor of the arabinose promoter. When batch glucose levels were depleted (<50 mg/L), a nutrient feed (containing 300 gm/L glucose) was started. The feed was increased linearly for 16 hours at a rate which limited acid bi-product formation. At this point, the nutrient feed was switched to media containing glycerol instead of glucose. Simultaneously, 500 gm/L L-arabinose was added to a final concentration of 5 gm/L. The glycerol feed was kept at a constant feed rate for 22 hours. Cells were harvested using hollow-fiber filtration to concentrate the suspension approximately 10-fold. Cell paste was stored at −70° C. A final cell mass of about 80 gm/L was obtained ($OD_{600}$=50–60) with a PAF-AH activity of 65–70 U/OD/ml representing about 10% of total cell protein. The final culture volume of about 75 liters contained 50–60 gm PAF-AH.

High level production of rPAF-AH products can be achieved when pBAR2/PH.2 or PH.9 is expressed by strains SB7219 or MC1061. Other strains deficient in arabinose degradation are suitable for high cell density production. Preferably, the cells are cultured under the following conditions. Exponentially growing SB7219; pBAR2/PH.2 and SB7219; pBAR2/PH.9 strains are seeded into fermentors containing batch medium containing 2 g/L glucose. Once glucose is consumed, the tanks are fed with a glycerol solution containing trace elements, vitamins, magnesium and ammonium salt to maintain healthy exponential growth. The tanks are maintained at 30° C., provided air to supply oxygen and agitated to maintain the dissolved oxygen level above about 15% saturation. When the cell density of the culture is above 110 g/L (wet cell mass), constant feed rate is imposed and a bolus addition of L-arabinose is added to the culture (about 0.5% final). Product formation is observed for 16–22 hours. The cultures typically achieve 40–50 g/L (dry cell weight). Cells are harvested by centrifugation, stored at −70° C., and rPAF-AH product purified for analysis. Specific productivities in excess of 150 units/ml/$OD_{600}$ are routinely obtained.

B. Expression in Yeast Cells

Recombinant human PAF-AH was also expressed in *Saccharomyces cerevisiae*. The yeast ADH2 promoter was used to drive rPAF-AH expression and produced 7 U/ml/$OD_{600}$ (Table 5 below).

TABLE 5

| Construct | Promoter | Strain | Enzyme Activity (U/ml/OD) |
|---|---|---|---|
| pUC tac AH | tac | E. coli W3110 | 30 |
| pUC trp AH | trp | E. coli W3110 | 40 |
| pUC ara AH | araB | E. coli W3110 | 20 |
| pET AH | T7 | E. coli BL21 (DE3) (Novagen) | 50 |
| pHAB/PH | araB/T7 | E. coli XL-1 | 34 |
| pBAR2/PH.2 | araB | MC1061 | 90 |
| pYep ADH2 AH | ADH2 | Yeast BJ2.28 | 7 |

C. Expression of PAF-AH in Mammalian Cells

1. Expression of Human PAF-AH cDNA Constructs

Plasmids constructed for expression of PAF-AH, with the exception of pSFN/PAFAH.1, employ a strong viral promoter from cytomegalovirus, a polyadenylation site from the bovine growth hormone gene, and the SV40 origin of replication to permit high copy number replication of the plasmid in COS cells. Plasmids were electroporated into cells.

A first set of plasmids was constructed in which the 5' flanking sequence (pDC1/PAFAH.1) or both the 5' or 3' flanking sequences (PDC1/PAFAH.2) of the human PAF-AH cDNA were replaced with flanking sequences from other genes known to be expressed at high levels in mammalian cells. Transfection of these plasmids into COS, CHO or 293 cells led to production of PAF-AH at about the same level (0.01 units/ml or 2–4 fold above background) as that cited for clone sAH 406-3 in Example 7 after transient transfection of COS cells. Another plasmid was constructed which included a Friend spleen focus-forming virus promoter instead of the cytomegalovirus promoter. The human PAF-AH cDNA was inserted into plasmid pmH-neo [Hahn et al., *Gene*, 127: 267 (1993)] under control of the Friend spleen focus-forming virus promoter. Transfection of the myeloma cell line NS0 with the plasmid which was designated pSFN/PAFAH.1 and screening of several hundred clones resulted in the isolation of two transfectants (4B11 and 1C11) that made 0.15–0.5 units/ml of PAF-AH activity. Assuming a specific activity of 5000 units/milligram, the productivity of these two NS0 transfectants corresponds to about 0.1 mg/liter.

2. Expression of Mouse-Human Chimeric PAF-AH Gene Constructs

A construct (pRc/MS9) containing the cDNA encoding mouse PAF-AH in the mammalian expression vector pRc/CMV resulted in production of secreted PAF-AH at the level of 5–10 units/ml (1000 fold above background) after transfection into COS cells. Assuming that the specific activity of the mouse PAF-AH is about the same as that of the human enzyme, the mouse cDNA is therefore expressed at a 500–1000 fold higher level than is the human PAF-AH cDNA.

To examine the difference between the expression levels of human and mouse PAF-AH in COS cells, two mouse-human chimeric genes were constructed and tested for expression in COS cells. The first of these constructs, pRc/PH.MHC1, contains the coding sequence for the N-terminal 97 amino acids of the mouse PAF-AH polypeptide (SEQ ID NO: 21) fused to the C-terminal 343 amino acids of human PAF-AH in the expression vector pRc/CMV (Invitrogen, San Diego, Calif.). The second chimeric gene, in plasmid pRc/PH.MHC2, contains the coding sequence for the N-terminal 40 amino acids of the mouse PAF-AH polypeptide fused to the C-terminal 400 residues of human PAF-AH in pRc/CMV. Transfection of COS cells with pRc/PH.MHC1 led to accumulation of 1–2 units/ml of PAF-AH activity in the media. Conditioned media derived from cells transfected with pRc/PH.MHC2 was found to contain only 0.01 units/ml of PAF-AH activity. From these experiments, it appears that the difference in expression level between mouse and human PAF-AH genes is attributable at least in part to the polypeptide segment between the residues 40 and 97, or the corresponding RNA or DNA segment encoding this region of the PAF-AH protein.

3. Recoding of the First 290 bp of the PAF-AH Coding Sequence

One hypothesis for the low level of human PAF-AH synthesized in transfected mammalian cells is that the codons utilized by the natural gene are suboptimal for efficient expression. However, it does not seem likely that codon usage can account for 500–1000 fold difference in expression levels between the mouse and human genes because optimizing codons generally has at most only a 10-fold effect on expression. A second hypothesis to explain the difference between the mouse and human PAF-AH expression levels is that the human PAF-AH mRNA in the 5' coding region forms a secondary structure that leads to either relatively rapid degradation of the mRNA or causes inefficient translation initiation or elongation.

To test these hypotheses, a synthetic fragment encoding the authentic human PAF-AH protein from the amino-terminus to residue 96 but in which most of the codons have been substituted ("recoded" ) with a codon of a different sequence but encoding the same amino acid was constructed. Changing the second codon from GTG to GTA resulted in the creation of an Asp718 site, which was at one end of the synthetic fragment and which is present in the mouse cDNA. The other end of the fragment contained the BamHi site normally found at codon 97 of the human gene. The approximately 290 bp Asp718BamHI fragment was derived from a PCR fragment that was made using the dual asymmetric PCR approach for construction of synthetic genes described in Sandhu et al., *Biotechniques*, 12: 14–16 (1992). The synthetic Asp718/BamHI fragment was ligated with DNA fragments encoding the remainder of the human PAF-AH molecule beginning with nucleotide 453 of SEQ ID NO: 7 such that a sequence encoding authentic human PAF-AH enzyme was inserted into the mammalian expression vector pRc/CMV (Invitrogen, San Diego) to create plasmid pRc/HPH.4. The complete sequence of the recoded gene is set out in SEQ ID NO: 30. The 5' flanking sequence adjacent to the human PAF-AH coding sequence in pRc/HPH.4 is from that of a mouse cDNA encoding PAF-AH in pRc/MS9 (nucleotides 1 to 116 of SEQ ID NO: 21).

To test expression of human PAF-AH from pRc/HPH.4, COS cells were transiently transfected with pRc/HPH.4 (recoded human gene), pRc/MS9 (mouse PAF-AH), or pRc/PH.MHC1 (mouse-human hybrid 1). The conditioned media from the transfected cells were tested for PAF-AH activity and found to contain 5.7 units/ml (mouse gene), 0.9 units/ml (mouse-human hybrid 1), or 2.6 units/ml (recoded human gene). Thus, the strategy of recoding the first 290 bp of coding sequence of human PAF-AH was successful in boosting expression levels of human PAF-AH from a few nanograms/ml to about 0.5 microgram/ml in a transient COS cell transfection. The recoded PAF-AH gene from pRc/HPH.4 will be inserted into a mammalian expression vector containing the dihydrofolate reductase (DHFR) gene and DHFR-negative chinese hamster ovary cells will be transfected with the vector. The transfected cells will be subjected to methotrexate selection to obtain clones making high levels of human PAF-AH due to gene amplification.

EXAMPLE 9

Recombinant human plasma PAF-AH (beginning at $Ile_{42}$) expressed in *E. coli* was purified to a single Coomassie-stained SDS-PAGE band by various methods and assayed for activities exhibited by the native PAF-AH enzyme.

A. Purification of Recombinant PAF-AH

The first purification procedure utilized is similar to that described in Example 1 for native PAF-AH. The following steps were performed at 4° C. Pellets from 50 ml PAF-AH producing *E. coli* (transformed with expression construct trp AH) were lysed as described in Example 8. Solids were removed by centrifugation at 10,000 g for 20 minutes. The supernatant was loaded at 0.8 ml/minute onto a Blue Sepharose Fast Flow column (2.5 cm×4 cm; 20 ml bed volume) equilibrated in buffer D (25 mM Tris-HCl, 10 mM CHAPS, 0.5M NaCl, pH 7.5). The column was washed with 100 ml buffer D and eluted with 100 ml buffer A containing 0.5M KSCN at 3.2 ml/minute. A 15 ml active fraction was loaded onto a 1 ml Cu Chelating Sepharose column equilibrated in buffer D. The column was washed with 5 ml buffer D followed by elution with 5 ml of buffer D containing 100 mM imidazole with gravity flow. Fractions containing PAF-AH activity were analyzed by SDS-PAGE.

The results of the purification are shown in Table 6 wherein a unit equals $\mu$mol PAF hydrolysis per hour. The purification product obtained at 4° C. appeared on SDS-PAGE as a single intense band below the 43 kDa marker with some diffuse staining directly above and below it. The recombinant material is significantly more pure and exhibits greater specific activity when compared with PAF-AH preparations from plasma as described in Example 1.

When the same purification protocol was performed at ambient temperature, in addition to the band below the 43 kDa marker, a group of bands below the 29 kDa marker correlated with PAF-AH activity of assayed gel slices. These lower molecular weight bands may be proteolytic fragments of PAF-AH that retain enzymatic activity.

A different purification procedure was also performed at ambient temperature. Pellets (100 g) of PAF-AH-producing *E. coli* (transformed with the expression construct pUC trp AH) were resuspended in 200 ml of lysis buffer (25 mM Tris, 20 mM CHAPS, 50 mM NaCl, 1 mM EDTA, 50 $\mu$g/ml benzamidine, pH 7.5) and lysed by passing three times through a microfluidizer at 15,000 psi. Solids were removed by centrifugation at 14,300×g for 1 hour. The supernatant was diluted 10-fold in dilution buffer [25 mM MES (2-[N-morpholino] ethanesulfonic acid), 10 mM CHAPS, 1 mM EDTA, pH 4.9] and loaded at 25 ml/minute onto an S Sepharose Fast Flow Column (200 ml) (a cation exchange column) equilibrated in Buffer E (25 mM MES, 10 mM CHAPS, 1 mM EDTA, 50 mM NaCl, pH 5.5). The column was washed with 1 liter of Buffer E, eluted with 1M NaCl, and the eluate was collected in 50 ml fractions adjusted to pH 7.5 with 0.5 ml of 2M Tris base. Fractions containing PAF-AH activity were pooled and adjusted to 0.5M NaCl. The S pool was loaded at 1 ml/minute onto a Blue Sepharose Fast Flow column (2.5 cm×4 cm; 20 ml) equilibrated in Buffer F (25 mM Tris, 10 mM CHAPS, 0.5M NaCl, 1 mM EDTA, pH 7.5). The column was washed with 100 ml Buffer F and eluted with 100 ml Buffer F containing 3M NaCl at 4 ml/minute. The Blue Sepharose Fast Flow chromatography step was then repeated to reduce endotoxin levels in the sample. Fractions containing PAF-AH activity were pooled and dialyzed against Buffer G (25 mM Tris pH 7.5, 0.5M NaCl, 0.1% Tween 80, 1 mM EDTA).

The results of the purification are shown in Table 7 wherein a unit equals $\mu$mol PAF hydrolysis per hour.

TABLE 6

| Sample | Volume (ml) | Activity (units/ ml) | Total Act. (units × $10^3$) | Prot Conc (mg/mL) | Specific Activity (units/ mg) | % Recovery of Activity Step | % Recovery of Activity Cum. | Fold Purification Step | Fold Purification Cum. |
|---|---|---|---|---|---|---|---|---|---|
| Lysate | 4.5 | 989 | 4451 | 15.6 | 63 | 100 | 100 | 1 | 1 |
| Blue | 15 | 64 | 960 | 0.07 | 914 | 22 | 22 | 14.4 | 14.4 |
| Cu | 1 | 2128 | 2128 | 0.55 | 3869 | 220 | 48 | 4.2 | 61 |

TABLE 7

| Sample | Volume (ml) | Activity (units/ ml) | Total Act. (units × $10^3$) | Prot Conc (mg/mL) | Specific Activity (units/ mg) | % Recovery of Activity Step | % Recovery of Activity Cum. | Fold Purification Step | Fold Purification Cum. |
|---|---|---|---|---|---|---|---|---|---|
| Lysate | 200 | 5640 | 1128 | 57.46 | 98 | 100 | 100 | 1 | 1 |
| S | 111 | 5742 | 637 | 3.69 | 1557 | 57 | 56 | 16 | 16 |
| Blue | 100 | 3944 | 394 | 0.84 | 4676 | 35 | 62 | 3 | 48 |

The purification product obtained appeared on SDS-PAGE as a single intense band below the 43 kDa marker with some diffuse staining directly above and below it. The recombinant material is significantly more pure and exhibits greater specific activity when compared with PAF-AH preparations from plasma as described in Example 1.

Yet another purification procedure contemplated by the present invention involves the following cell lysis, clarification, and first column steps. Cells are diluted 1:1 in lysis buffer (25 mM Tris pH 7.5, 150 mM NaCl, 1% Tween 80, 2 mM EDTA). Lysis is performed in a chilled microfluidizer at 15,000–20,000 psi with three passes of the material to yield >99% cell breakage. The lysate is diluted 1:20 in dilution buffer (25 mM Tris pH 8.5, 1 mM EDTA) and applied to a column packed with Q-Sepharose Big Bead chromatography media (Pharmacia) and equilibrated in 25 mM Tris pH 8.5, 1 mM EDTA, 0.015% Tween 80. The eluate is diluted 1:10 in 25 mM MES pH 5.5, 1.2M Ammonium sulfate, 1 mM EDTA and applied to Butyl Sepharose chromography media (Pharmacia) equilibrated in the same buffer. PAF-AH activity is eluted in 25 mM MES pH 5.5, 0.1% Tween 80, 1 mM EDTA.

Still another method contemplated by the invention for purifying enzymatically-active PAF-AH from *E.coli* includes the steps of: (a) preparing an *E.coli* extract which yields solubilized PAF-AH supernatant after lysis in a buffer containing CHAPS; (b) dilution of the said supernatant and application to a anion exchange column equilibrated at about pH 8.0; (c) eluting PAF-AH enzyme from said anion exchange column; (d) applying said adjusted eluate from said anion exchange column to a blue dye ligand affinity column; (e) eluting the said blue dye ligand affinity column using a buffer comprising 3.0M salt; (f) dilution of the blue dye eluate into a suitable buffer for performing hydroxylapatite chromatography; (g) performing hydroxylapatite chromatography where washing and elution is accomplished using buffers (with or without CHAPS); (h) diluting said hydroxylapatite eluate to an appropriate salt concentration for cation exchange chromatography; (i) applying said diluted hydroxylapatite eluate to a cation exchange column at a pH ranging between approximately 6.0 to 7.0; (j) elution of PAF-AH from said cation exchange column with a suitable formulation buffer; (k) performing cation exchange chromatography in the cold; and (l) formulation of PAF-AH in liquid or frozen form in the absence of CHAPS.

Preferably in step (a) above the lysis buffer is 25 mM Tris, 100 mM NaCl, 1 mM EDTA, 20 mM CHAPS, pH 8.0; in step (b) the dilution of the supernatant for anion exchange chromatography is 3–4 fold into 25 mM Tris, 1 mM EDTA, 10 mM CHAPS, pH 8.0 and the column is a Q-Sepharose column equilibrated with 25 mM Tris, 1 mM EDTA, 50 mM NaCl, 10 mM CHAPS, pH 8.0; in step (c) the anion exchange column is eluted using 25 mM Tris, 1 mM EDTA, 350 mM NaCl, 10 mM CHAPS, pH 8.0; in step (d) the eluate from step (c) is applied directly onto a blue dye affinity column; in step (e) the column is eluted with 3M NaCl, 10 mM CHAPS, 25 mM Tris, pH 8.0 buffer; in step (f) dilution of the blue dye eluate for hydroxylapatite chromatography is accomplished by dilution into 10 mM sodium phosphate, 100 mM NaCl, 10 mM CHAPS, pH 6.2; in step (g) hydroxylapatite chromatography is accomplished using a hydroxylapatite column equilibrated with 10 mM sodium phosphate, 100 mM NaCl, 10 mM CHAPS and elution is accomplished using 50 mM sodium phosphate, 100 mM NaCl (with or without) 10 mM CHAPS, pH 7.5; in step (h) dilution of said hydroxylapatite eluate for cation exchange chromatography is accomplished by dilution into a buffer ranging in pH from approximately 6.0 to 7.0 comprising sodium phosphate (with or without CHAPS); in step (i) a S Sepharose column is equilibrated with 50 mM sodium phosphate, (with or without) 10 mM CHAPS, pH 6.8; in step (j) elution is accomplished with a suitable formulation buffer such as potassium phosphate 50 mM, 12.5 mM aspartic acid, 125 mM NaCl, pH 7.5 containing 0.01% Tween-80; and in step (k) cation exchange chromatography is accomplished at 2–8° C. Examples of suitable formulation buffers for use in step (l) which stabilize PAF-AH include 50 mM potassium phosphate, 12.5 mM Aspartic acid, 125 mM NaCl pH 7.4 (approximately, with and without the addition of Tween-80 and or Pluronic F68) or 25 mM potassium phosphate buffer containing (at least) 125 mM NaCl, 25 mM arginine and 0.01% Tween-80 (with or without Pluronic F68 at approximately 0.1 and 0.5%).

B. Activity of Recombinant PAF-AH

The most remarkable property of the PAF acetylhydrolase is its marked specificity for substrates with a short residue at the sn-2 position of the substrate. This strict specificity distinguishes PAF acetylhydrolase from other forms of $PLA_2$. Thus, to determine if recombinant PAF-AH degrades phospholipids with long-chain fatty acids at the sn-2 position, hydrolysis of 1-palmitoyl-2-arachidonoyl-sn-glycero-3-phosphocholine (arachidonoylPC) was assayed since this is the preferred substrate for a well-characterized form of $PLA_2$. As predicted from previous studies with native PAF-AH, this phospholipid was not hydrolyzed when incubated with recombinant PAF-AH. In additional experiments, arachidonoylPC was included in a standard PAF hydrolysis assay at concentrations ranging from 0 to 125 $\mu$M to determine whether it inhibited the hydrolysis of PAF by recombinant PAF-AH. There was no inhibition of PAF hydrolysis even at the highest concentration of PAF-AH, which was 5-fold greater than the concentration of PAF. Thus, recombinant PAF-AH exhibits the same substrate selectivity as the native enzyme; long chain substrates are not recognized. Moreover, recombinant PAF-AH enzyme rapidly degraded an oxidized phospholipid (glutaroylPC) which had undergone oxidative cleavage of the sn-2 fatty acid. Native plasma PAF-AH has several other properties that distinguish it from other phospholipases including calcium-independence and resistance to compounds that modify sulfhydryl groups or disrupt disulfides.

Both the native and recombinant plasma PAF-AH enzymes are sensitive to DFP, indicating that a serine comprises part of their active sites. An unusual feature of the native plasma PAF acetylhydrolase is that it is tightly associated with lipoproteins in circulation, and its catalytic efficiency is influenced by the lipoprotein environment. When recombinant PAF-AH of the invention was incubated with human plasma (previously treated with DFP to abolish the endogenous enzyme activity), it associated with low and high density lipoproteins in the same manner as the native activity. This result is significant because there is substantial evidence that modification of low density lipoproteins is essential for the cholesterol deposition observed in atheromas, and that oxidation of lipids is an initiating factor in this process. PAF-AH protects low density lipoproteins from modification under oxidizing conditions in vitro and may have such a role in vivo. Administration of PAF-AH is thus indicated for the suppression of the oxidation of lipoproteins in atherosclerotic plaques as well as to resolve inflammation.

These results all confirm that the cDNA clone sAH 406-3 encodes a protein with the activities of the the human plasma PAF acetylhydrolase.

EXAMPLE 10

Various other recombinant PAF-AH products were expressed in *E. coli*. The products included PAF-AH analogs having single amino acid mutations and PAF-AH fragments.

A. PAF-AH Amino Acid Substitution Products

PAF-AH is a lipase because it hydrolyses the phospholipid PAF. While no obvious overall similarity exists between PAF-AH and other characterized lipases, there are conserved residues found in comparisons of structurally characterized lipases. A serine has been identified as a member of the active site. The serine, along with an aspartate residue and a histidine residue, form a catalytic triad which represents the active site of the lipase. The three residues are not adjacent in the primary protein sequence, but structural studies have demonstrated that the three residues are adjacent in three dimensional space. Comparisons of structures of mammalian lipases suggest that the aspartate residue is generally twenty-four amino acids C-terminal to the active site serine. In addition, the histidine is generally 109 to 111 amino acids C-terminal to the active site serine.

By site-directed mutagenesis and PCR, individual codons of the human PAF-AH coding sequence were modified to encode alanine residues and were expressed in *E. coli*. As shown in Table 8 below wherein, for example, the abbreviation "S108A" indicates that the serine residue at position 108 was changed to an alanine, point mutations of $Ser_{273}$, $Asp_{296}$, or $His_{351}$ completely destroy PAF-AH activity. The distances between active site residues is similar for PAF-AH (Ser to Asp, 23 amino acids; Ser to His, 78 amino acids) and other lipases. These experiments demonstrate that $Ser_{273}$, $Asp_{296}$, and $His_{351}$ are critical residues for activity and are therefore likely candidates for catalytic triad residues. Cysteines are often critical for the functional integrity of proteins because of their capacity to form disulfide bonds. The plasma PAF-AH enzyme contains five cysteines. To determine whether any of the five is critical for enzyme activity, each cysteine was mutated individually to a serine and the resulting mutants were expressed in *E. coli*. Preliminary activity results using partially purified preparations of these recombinantly produced mutants are shown below in the second column of Table 8, while results using more purified preparations are shown below in the third column of Table 8. The data show that all of the cysteine mutants had largely equivalent activity, so that none of the cysteines appears to be necessary for PAF-AH activity. Other point mutations also had little or no effect on PAF-AH catalytic activity. In Table 8, "++++" represents wild type PAF-AH activity of about 40–60 $U/ml/OD_{600}$, "+++" represents about 20–40 $U/ml/OD_{600}$ activity, "++" represents about 10–20 $U/ml/OD_{600}$ activity, "+" represents 1–10 $U/ml/OD_{600}$ activity, and "−" indicates <1 $U/ml/OD_{600}$ activity.

TABLE 8

| Mutation | PAF-AH activity | Specific PAF-AH activity of purified preparations |
| --- | --- | --- |
| Wild type | ++++ | 6.9 mmol/mg/hr |
| S108A | ++++ | |
| S273A | − | |
| D286A | − | |
| D286N | ++ | |
| D296A | − | |
| D304A | ++++ | |
| D338A | ++++ | |
| H351A | − | |
| H395A, H399A | ++++ | |
| C67S | +++ | 5.7 mmol/mg/hr |
| C229S | + | 6.5 mmol/mg/hr |
| C291S | + | 5.9 mmol/mg/hr |
| C334S | ++++ | 6.8 mmol/mg/hr |
| C407S | +++ | 6.4 mmol/mg/hr |
| C67S, C334S, C407S | | 6.8 mmol/mg/hr |

B. PAF-AH Fragment Products

Figure 3:
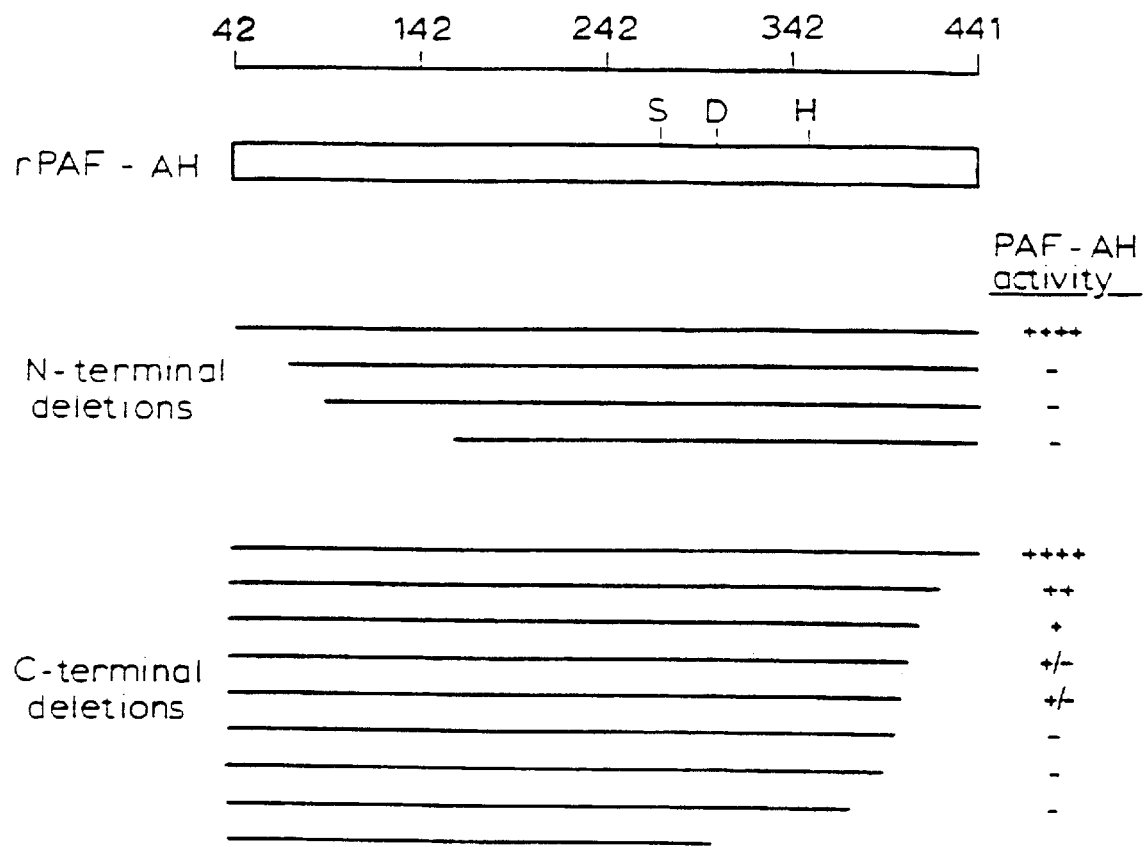
FIG. 3 is a schematic drawing depicting recombinant PAF-AH fragments and their catalytic activity.

C-terminal deletions were prepared by digesting the 3' end of the PAF-AH coding sequence with exonuclease III for various amounts of time and then ligating the shortened coding sequence to plasmid DNA encoding stop codons in all three reading frames. Ten different deletion constructs were characterized by DNA sequence analysis, protein expression, and PAF-AH activity. Removal of twenty-one to thirty C-terminal amino acids greatly reduced catalytic activity and removal of fifty-two residues completely destroyed activity. See FIG. 3.

Similar deletions were made at the amino terminal end of PAF-AH. Fusions of PAF-AH with *E. coli* thioredoxin at the N-terminus were prepared to facilitate consistent high level expression PAF-AH activity [LaVallie et al., *Bio/technology*, 11:187–193 (1993)]. Removal of nineteen amino acids from the naturally processed N-terminus ($Ile_{42}$) reduced activity by 99% while removal of twenty-six amino acids completely destroyed enzymatic activity in the fusion protein. See FIG. 3. Deletion of twelve amino acids appeared to enhance enzyme activity about four fold.

In subsequent purifications of PAF-AH from fresh human plasma by a method similar to that described in Example 1 (Microcon 30 filter from Amicon were utilized to concentrate Blue sepharose eluate instead of a Cu column), two N-termini in addition to $Ile_{42}$ were identified, $Ser_{35}$ and $Lys_{55}$. The heterogeneity may be the natural state of the enzyme in plasma or may occur during purification.

The purified material described above was also subject to analysis for glycosylation. Purified native PAF-AH was incubated in the presence or absence of N-Glycanase, an enzyme that removes N-linked carbohydrates from glycoproteins. The treated PAF-AH samples were electrophoresed through a 12% SDS polyacrylamide gel then visualized by Western blotting using rabbit polyclonal antisera. Protein not treated with N-Glycanase migrated as a diffuse band of 45–50 kDa whereas the protein treated with the glycanase migrated as a tight band of about 44 kDa, demonstrating that native PAF-AH is glycosylated.

N-terminal heterogeneity was also observed in purified preparations of recombinant PAF-AH ($Ile_{42}$ N-terminus). These preparations were a mixture of polypeptides with N-termini beginning at $Ala_{47}$, $Ile_{42}$, or the artificial initiating $Met_{-1}$ adjacent to $Ile_{42}$.

1. Preliminary comparison of PAF-AH fragments with PAF-AH

In view of the observed heterogeneity of recombinantly produced PAF-AH, other recombinant products were prepared and tested for homogeneity after recombinant expression and purification. The composition of the recombinant expression products of pBAR2/PH.2 and pBAR2/PH.9 in *E. coli* strain MC1061 was analyzed at different time points during the production phase of cell fermentation. Partially purified samples of the recombinant PH.2 and PH.9 from cells collected at time points ranging between 5 and 22 hours after induction of protein expression were analyzed by matrix assisted laser desorption ionization mass spectrometry (MALDI-MS).

When the PH.2 expression vector was utilized, two peaks were observed in the spectrum of the partially purified protein at a mass value expected for rPAF-AH protein. Two peaks were observed at all time points, with greater heterogeneity being observed at time points when fermentation is stressed as indicated by an accumulation of acetate and/or a depletion of oxygen in the media. The accuracy of the MALDI-MS technique in this mass range was approximately ±0.3%, about the mass of one amino acid. The higher mass peak observed was consistent with the presence of the expected full length translation product for the PH.2 vector, minus the translation initiating methionine which is expected to be post-translationally removed. The lower mass peak was approximately 1200 atomic mass units less.

When the PH.9 expression vector was utilized, a single peak predominated in the spectrum of the partially purified protein at a mass value expected for rPAF-AH protein. This single peak was observed at all time points, with no increase in heterogeneity seen at different time points. The observed mass of this protein was consistent with the presence of the expected full length translation product for the PH.9 vector, minus the initiating methionine.

2. Purification of PAF-AH fragments

Recombinantly expressed rPH.2 (the expression product of DNA encoding $Met_{46}$-$Asn_{441}$) and rPH.9 (the expression product of DNA encoding $Met_{46}$-$Ile_{429}$) preparations were purified for further comparison with purified rPAF-AH (expression product of DNA encoding $Ile_{42}$-$Asn_{441}$). rPH.9 was produced by E. coli strain SB7219 and purified generally according to the zinc chelate purification procedure described above, while rPH.2 was produced by E. coli strain MC1061 and purified as described below. The transformed cells were lysed by dilution of the cell paste with lysis buffer (100 mM succinate, 100 mM NaCl, 20 mM CHAPS, pH 6.0). The slurry was mixed and lysed by high pressure disruption. The lysed cells were centrifuged and the supernatant containing rPH.2 was retained. The clarified supernatant was diluted 5-fold in 25 mM sodium phosphate buffer containing, 1 mM EDTA, 10 mM CHAPS, pH 7.0. The diluted supernatant was then applied to the Q Sepharose column. The column was washed first with 3 column volumes of 25 mM sodium phosphate buffer containing 1 mM EDTA, 50 mM NaCl, 10 mM CHAPS, pH 7.0 (Wash 1), then washed with 10 column volumes of 25 mM Tris buffer containing 1 mM EDTA, 10 mM CHAPS, pH 8.0 (Wash 2) and with 10 column volumes of 25 mM Tris buffer containing 1 mM EDTA, 100 mM NaCl, 10 mM CHAPS, pH 8.0 (Wash 3). Elution was accomplished with 25 mM Tris buffer containing 1 mM EDTA, 350 mM NaCl, 10 mM CHAPS, pH 8.0. The Q Sepharose eluate was diluted 3-fold in 25 mM Tris, 1 mM EDTA, 10 mM CHAPS, pH 8.0 then applied to a Blue Sepharose column. The column was washed first with 10 column volumes of 25 mM Tris, 1 mM EDTA, 10 mM CHAPS, pH 8.0. The column was then washed with 3 column volumes of 25 mM Tris, 0.5 M NaCl, 10 mM CHAPS, pH 8.0. Elution was accomplished with 25 mM Tris, 3.0 M NaCl, 10 mM CHAPs, pH 8.0. The Blue Sepharose eluate was diluted 5-fold in 10 mM sodium phosphate, 10 mM CHAPS, pH 6.2 then applied to the chromatography column. The column was washed with 10 column volumes of 10 mM sodium phosphate, 100 mM NaCl, 0.1% Pluronic F68, pH 6.2. rPH.2 was eluted with 120 mM sodium phosphate, 100 mM NaCl, 0.1% Pluronic F-68, pH 7.5. The hydroxyapatite eluate was diluted 6-fold with 10 mM sodium phosphate, 0.1% Pluronic F68, pH 6.8. The diluted hydroxyapatite eluate was adjusted to pH 6.8 using 0.5 N succinic acid and then applied to a SP Sepharose column. The SP Sepharose column was washed with 10 column volumes 50 mM sodium phosphate, 0.1% Fluronic F68, pH 6.8 and eluted with 50 mM sodium phosphate, 125 mM NaCl, 0.1% Pluronic F68, pH 7.5. The eluted rPH.2 was formulated by diluting to a final concentration of 4 mg/ml in 50 mM sodium phosphate, 125 mM NaCl, 0.15% Pluronic F68, pH 7.5, and Tween 80 was added to a final concentration of 0.02% Tween 80. The formulated product was then filtered through a $0.2\mu$ membrane and stored prior to use.

3. Comparison of PAF-AH fragments with PAF-AH by sequencing

The purified rPH.2 and rPH.9 preparations were compared with purified rPAF-AH preparations by N-terminal sequencing using an Applied Biosystems Model 473A Protein Sequencer (Applied Biosystems, Foster City, Calif.) and by C-terminal sequencing using a Hewlett-Packard Model G1009A C-terminal Protein Sequencer. The rPH.2 preparation had less N-terminal heterogeneity compared to rPAF-AH. The N-terminus analysis of the rPH.9 preparation was similar to that of rPH.2, but less C-terminal heterogeneity was observed for the rPH.9 preparation relative to rPH.2.

The purified rPH.2 preparation contained a major sequence with an N-terminus of $Ala_{47}$ (about 86–89%) and a minor sequence with an N-terminus of $Ala_{48}$ (about 11–14%), with the ratio of the two N-termini being fairly consistent under different fermentation conditions. The purified rPH.9 preparation also contained a major sequence with an N-terminus of $Ala_{47}$ (about 83–90%) and a minor sequence with an N-terminus of $Ala_{48}$ (about 10–17%). In contrast, attempts to produce in bacteria the polypeptide beginning at $Ile_{42}$ (rPAF-AH) resulted in a varying mixture of polypeptides with N-termini beginning at $Ala_{47}$ (20–53%), $Ile_{42}$ (8–10%), or at the artificial initiating $Met_{-1}$ methionine (37–72%) adjacent to $Ile_{42}$. For rPH.2 and rPH.9, the initiating methionine is efficiently removed by an amino-terminal peptidase after bacterial synthesis of the polypeptide, leaving the alanine at position 47 (or the alanine at position 48) as the N-terminal residue.

C-terminal sequencing was carried out on one lot of rPH.2, which was observed to have a C-terminus of HOOC-Asn-Tyr as the major sequence (about 80%), consistent with the predicted HOOC-$Asn_{441}$-$Tyr_{440}$ C-terminus of the translation product, while about 20% was HOOC-Leu. After the rPH.2 preparation had been fractionated by SDS-PAGE, additional sequencing of the primary and secondary bands yielded a C-terminal sequence of HOOC-Leu-Met from a lower secondary band ($AH_L$, described below in section B.5.) consistent with a product that is 10 amino acids shorter than the full length translation product, as well as low levels of HOOC-His. Further peptide mapping has shown that additional C-termini are present in some lots of PH.2 protein. The C-terminus of rPH.9 was primarily HOOC-Ile-His (about 78 to 91%, depending on the lot) by direct sequencing, consistent with the predicted HOOC-$Ile_{429}$-$His_{428}$ C-terminus of the translation product. There appears to be some background ("noise") in this technique, so low levels of other sequences could not be ruled out.

4. Comparison of PAF-AH fragments with PAF-AH by MALDI-MS

Figure 4:
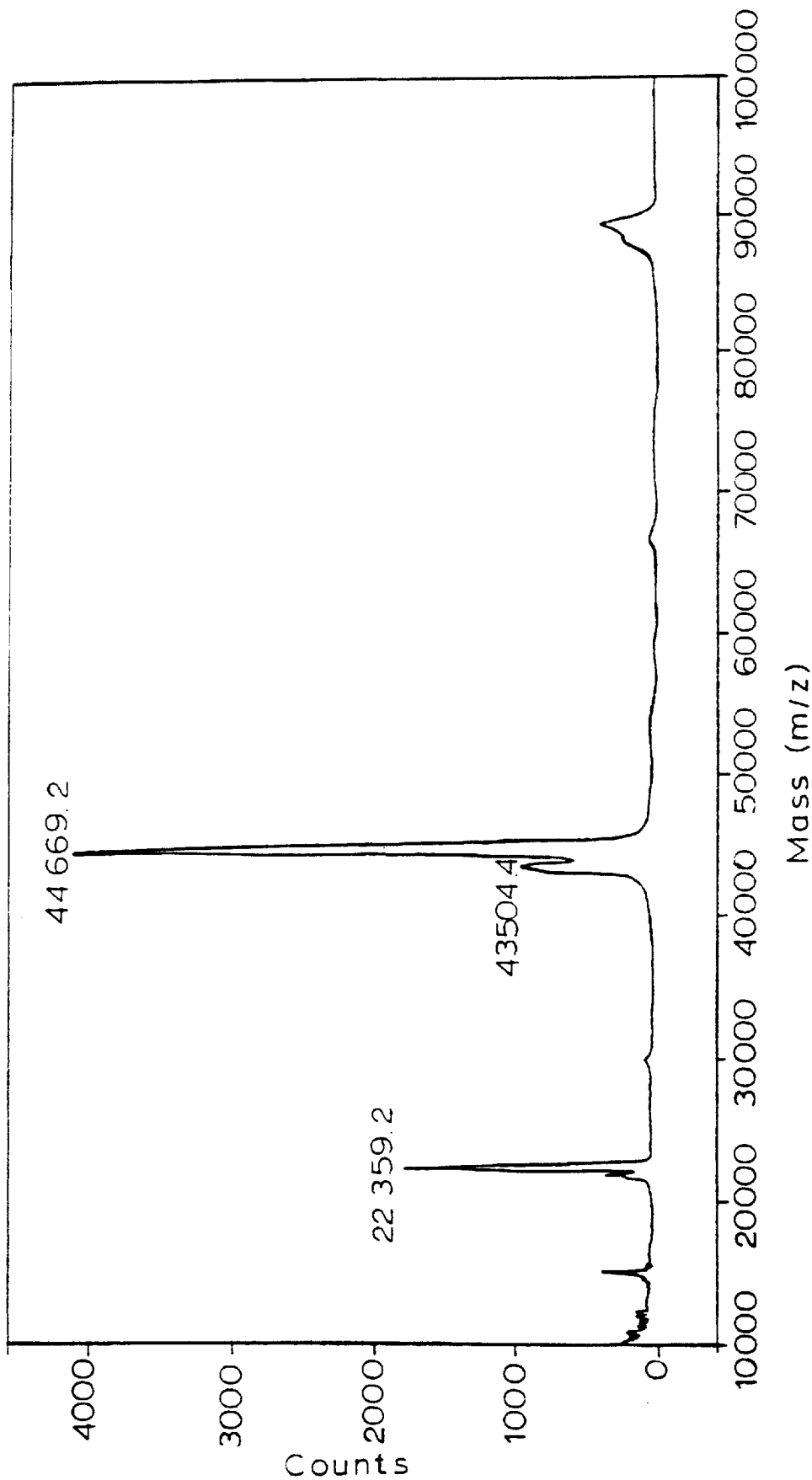
FIG. 4 depicts mass spectroscopy results for a recombinant PAF-AH product, rPH.2.
Figure 5:
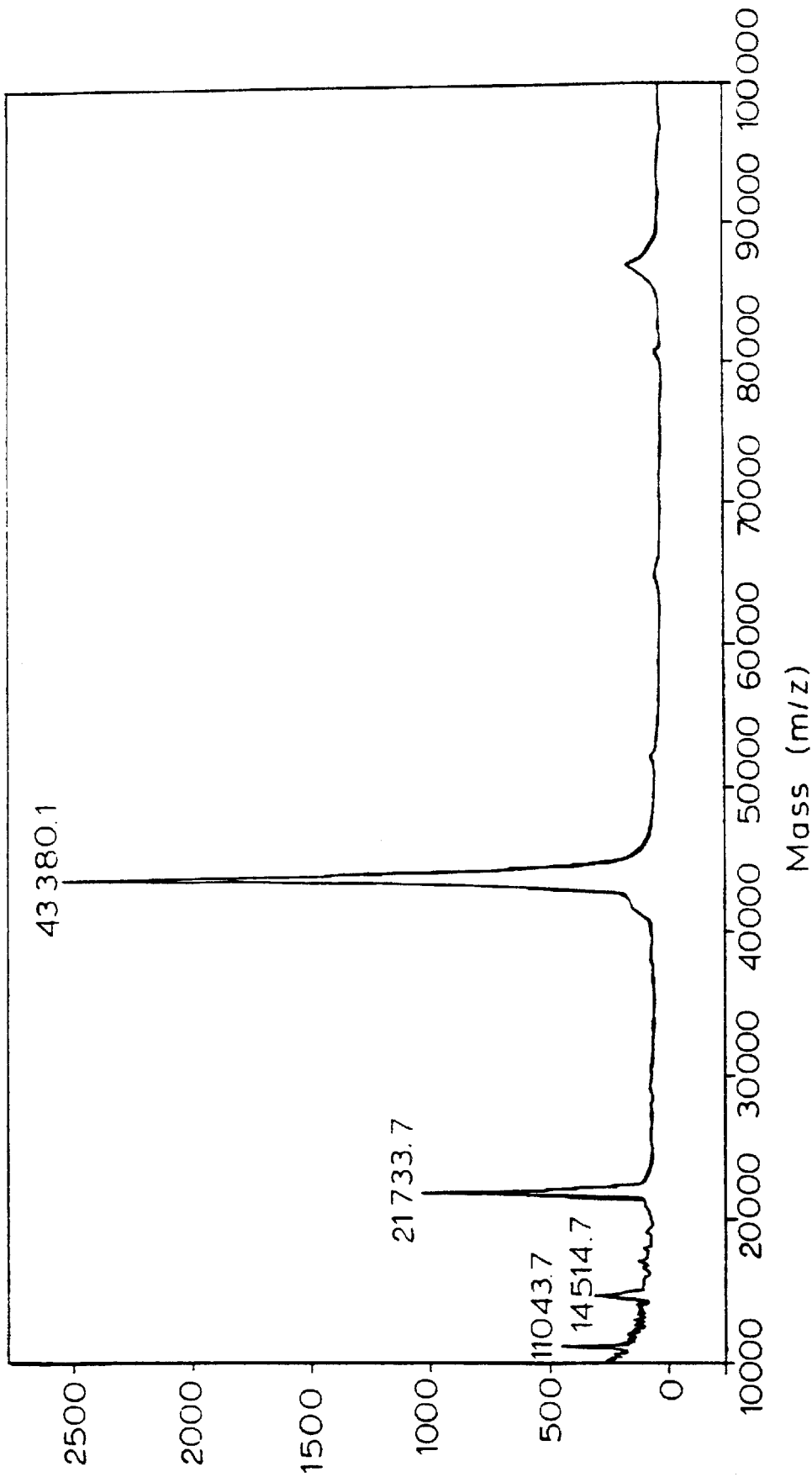
FIG. 5 depicts mass spectroscopy results for a recombinant PAF-AH product, rPH.9.

MALDI-MS was performed on purified rPH.2 and rPH.9 preparations. The rPH.2 spectrum exhibited two peaks in the spectrum at a mass value expected for the rPAF-AH product (see FIG. 4), similar to the pattern observed with the partially purified protein in section B.1. above. The secondary, lower molecular weight peak was typically present at approximately 20% to 30% of the total. The rPH.9 spectrum showed a predominant peak at a mass consistent with that expected for the full length translation product for the PH.9 vector, minus the translation initiating methionine (see FIG. 5). A small slightly lower molecular weight shoulder peak was also observed for rPH.9 that represented approximately 5% of the total.

5. Comparison of PAF-AH fragments with PAF-AH by SDS-PAGE

Sodium dodecyl sulfate-polyacrylamide electrophoresis (SDS-PAGE) was performed on purified rPAF-AH, rPH.2 and rPH.9 preparations. A complicated banding pattern was observed for rPH.2 around the electrophoretic migration range expected for the rPAF-AH product, based on protein molecular weight standards. One, or in some gels, two predominant bands were seen, with readily observed secondary bands above and below the primary band. These upper secondary, middle primary and lower secondary bands, respectively, were termed $AH_U$, $AH_M$ and $AH_L$. All of these bands reacted with an anti-rPAF-AH monoclonal antibody on Western blot and have thus been identified as rPAF-AH related products. The upper secondary band $AH_U$ increased in intensity over time with storage of the protein and presumably represents a modified form of the rPAF-AH product. The SDS-PAGE of the rPAF-AH preparation is similar to that of rPH.2. There are two major bands that migrate near the expected molecular weight for rPAF-AH, as well as a minor band above and a shadow below the major bands. In contrast, rPH.9 displayed a single predominant band on SDS-PAGE with no apparent splitting. Faint bands at a slightly lower molecular weight and at an expected dimer position were also seen. No $AH_U$-like band was observed.

The composition of the purified rPH.2 and rPH.9 preparations was also analyzed on 2D gels (isoelectric focusing (IEF) in urea followed by SDS-PAGE in the second dimension). For rPH.9, the 2D gels showed five main spots separated in the IEF direction. The charge heterogeneity appeared consistent between lots of rPH.9. In contrast, the 2D gel pattern of rPH.2 was more complicated as it contained approximately 15 spots separated in the IEF and SDS-PAGE dimensions.

6. Comparison of activity of PAF-AH framents with PAF-AH

Purified rPH.2 and rPH.9 have enzymatic activity indistinguishable from that of endogenous PAF-AH purified from serum, and rPH.2 and rPH.9 bind to lipropotein in a similar manner as purified endogenous PAF-AH.

EXAMPLE 11

A preliminary analysis of expression patterns of human plasma PAF-AH mRNA in human tissues was conducted by Northern blot hybridization.

RNA was prepared from human cerebral cortex, heart, kidney, placenta, thymus and tonsil using RNA Stat 60 (Tel-Test "B", Friendswood, Tex.). Additionally, RNA was prepared from the human hematopoietic precursor-like cell line, THP-1 (ATCC TIB 202), which was induced to differentiate to a macrophage-like phenotype using the phorbol ester phorbolmyristylacetate (PMA). Tissue RNA and RNA prepared from the premyelocytic THP-1 cell line prior to and 1 to 3 days after induction were electrophoresed through a 1.2% agarose formaldehyde gel and subsequently transferred to a nitrocellulose membrane. The full length human plasma PAF-AH cDNA, sAH 406-3, was labelled by random priming and hybridized to the membrane under conditions identical to those described in Example 3 for library screening. Initial results indicate that the PAF-AH probe hybridized to a 1.8 kb band in the thymus, tonsil, and to a lesser extent, the placental RNA.

PAF is synthesized in the brain under normal physiological as well as pathophysiological conditions. Given the known pro-inflammatory and potential neurotoxic properties of the molecule, a mechanism for localization of PAF synthesis or for its rapid catabolism would be expected to be critical for the health of neural tissue. The presence of PAF acetylhydrolase in neural tissues is consistent with it playing such a protective role. Interestingly, both a bovine heterotrimeric intracellular PAF-AH [the cloning of which is described in Hattori et al., *J. Biol. Chem.*, 269(37): 23150–23155 (1994)] and PAF-AH of the invention have been identified in the brain. To determine whether the two enzymes are expressed in similar or different compartments of the brain, the human homologue of the bovine brain intracellular PAF-AH cDNA was cloned, and its mRNA expression pattern in the brain was compared by Northern blotting to the mRNA expression pattern of the PAF-AH of the invention by essentially the same methods as described in the foregoing paragraph. The regions of the brain examined by Northern blotting were the cerebellum, medulla, spinal cord, putamen, amygdala, caudate nucleus, thalamus, and the occipital pole, frontal lobe and temporal lobe of the cerebral cortex. Message of both enzymes was detected in each of these tissues although the heterotrimeric intracellular form appeared in greater abundance than the secreted form. Northern blot analysis of additional tissues further revealed that the heterotrimeric intracellular form is expressed in a broad variety of tissues and cells, including thymus, prostate, testis, ovary, small intestine, colon, peripheral blood leukocytes, macrophages, brain, liver, skeletal muscle, kidney, pancreas and adrenal gland. This ubiquitous expression suggests that the heterotrimeric intracellular PAF-AH has a general housekeeping function within cells.

The expression of PAF-AH RNA in monocytes isolated from human blood and during their spontaneous differentiation into macrophages in culture was also examined. Little or no RNA was detected in fresh monocytes, but expression was induced and maintained during differentiation into macrophages. There was a concomitant accumulation of PAF-AH activity in the culture medium of the differentiating cells. Expression of the human plasma PAF-AH transcript was also observed in the THP-1 cell RNA at 1 day but not 3 days following induction. THP-1 cells did not express mRNA for PAF-AH in the basal state.

EXAMPLE 12

PAF-AH expression in human and mouse tissues was examined by in situ hybridization.

Human tissues were obtained from National Disease Research Interchange and the Cooperative Human Tissue Network. Normal mouse brain and spinal cord, and EAE stage 3 mouse spinal cords were harvested from S/JLJ mice. Normal S/JLJ mouse embryos were harvested from eleven to eighteen days after fertilization.

The tissue sections were placed in Tissue Tek II cryomolds (Miles Laboratories, Inc., Naperville, Ill.) with a small amount of OCT compound (Miles, Inc., Elkhart, Ind.). They were centered in the cryomold, the cryomold filled with OCT compound, then placed in a container with 2-methylbutane [$C_2H_5CH(CH_3)_2$, Aldrich Chemical Company, Inc., Milwaukee, Wis.] and the container placed in liquid nitrogen. Once the tissue and OCT compound in the cryomold were frozen, the blocks were stored at −80° C.

until sectioning. The tissue blocks were sectioned at 6 μm thickness and adhered to Vectabond (Vector Laboratories, Inc., Burlingame, Calif.) coated slides and stored at −70° C. and placed at 50° C. for approximately 5 minutes to warm them and remove condensation and were then fixed in 4% paraformaldehyde for 20 minutes at 4° C., dehydrated (70%, 95%, 100% ethanol) for 1 minute at 4° C. in each grade, then allowed to air dry for 30 minutes at room temperature. Sections were denatured for 2 minutes at 70° C. in 70% formamide/2× SSC, rinsed twice in 2× SSC, dehydrated and then air dried for 30 minutes. The tissues were hybridized in situ with radiolabeled single-stranded mRNA generated from DNA derived from an internal 1 Kb HindIII fragment of the PAF-AH gene (nucleotides 308 to 1323 of SEQ ID NO: 7) by in vitro RNA transcription incorporation $^{35}$S-UTP (Amersham) or from DNA derived from the heterotrimeric intracellular PAF-AH cDNA identified by Hattori et al. The probes were used at varying lengths from 250–500 bp. Hybridization was carried out overnight (12–16 hours) at 50° C; the $^{35}$S-labeled riboprobes ($6\times10^5$ cpm/section), tRNA (0.5 μg/section) and diethylpyrocarbonate (depc)-treated water were added to hybridization buffer to bring it a final concentration of 50% formamide, 0.3M NaCl, 20 mM Tris pH 7.5, 10% dextran sulfate, 1× Denhardt's solution, 100 mM dithiothretol (DTT) and 5 mM EDTA. After hybridization, sections were washed for 1 hour at room temperature in 4× SSC/10 mM DTT, then for 40 minutes at 60° C. in 50% formamide/1× SSC/10 mM DTT, 30 minutes at room temperature in 2× SSC, and 30 minutes at room temperature in 0.1× SSC. The sections were dehydrated, air dried for 2 hours, coated with Kodak NTB2 photographic emulsion, air dried for 2 hours, developed (after storage at 4° C. in complete darkness) and counterstained with hematoxylinleosin.

A. Brain

Cerebellum. In both the mouse and the human brains, strong signal was seen in the Purkinje cell layer of the cerebellum, in basket cells, and individual neuronal cell bodies in the dentate nucleus (one of the four deep nuclei in the cerebellum). Message for the heterotrimeric intracellular PAF-AH was also observed in these cell types. Additionally, plasma PAF-AH signal was seen on individual cells in the granular and molecular layers of the grey matter.

Hippocampus. In the human hippocampus section, individual cells throughout the section, which appear to be neuronal cell bodies, showed strong signal. These were identified as polymorphic cell bodies and granule cells. Message for the heterotrimeric intracellular PAF-AH was also observed in hippocampus.

Brain stem. On both human and mouse brain stem sections, there was strong signal on individual cells in the grey matter.

Cortex. On human cortex sections taken from the cerebral, occipital, and temporal cortexes, and on mouse whole brain sections, individual cells throughout the cortex showed strong signal. These cells were identified as pyramidal, stellate and polymorphic cell bodies. There does not appear to be differentiation in the expression pattern in the different layers of the cortex. These in situ hybridization results are different from the results for cerebral cortex obtained by Northern blotting. The difference is likely to result from the greater sensitivity of in situ hybridization compared to that of Northern blotting. As in the cerebellum and hippocampus, a similar pattern of expression of the heterotrimeric intracellular PAF-AH was observed.

Pituitary. Somewhat weak signal was seen on scattered individual cells in the pars distalis of the human tissue section.

B. Human Colon

Both normal and Crohn's disease colons displayed signal in the lymphatic aggregations present in the mucosa of the sections, with the level of signal being slightly higher in the section from the Crohn's disease patient. The Crohn's disease colon also had strong signal in the lamina propria. Similarly, a high level of signal was observed in a diseased appendix section while the normal appendix exhibited a lower but still detectable signal. The sections from the ulcerative colitis patient showed no evident signal in either the lymphatic aggregations or the lamina propria.

C. Human Tonsil and Thymus

Strong signal was seen on scattered groups of individual cells within the germinal centers of the tonsil and within the thymus.

D. Human Lymph Node

Strong signal was observed on the lymph node section taken from a normal donor, while somewhat weak signal was observed in the lymph nodules of the section from a donor with septic shock.

E. Human Small Intestine

Both normal and Crohn's disease small intestine had weak signal in the Peyer's patches and lamina propria in the sections, with the signal on the diseased tissue slightly higher.

F. Human Spleen and Lung

Signal was not observed on any of the spleen (normal and splenic abcess sections) or lung (normal and emphysema sections) tissues.

G. Mouse Spinal Cord

In both the normal and EAE stage 3 spinal cords, there was strong signal in the grey matter of the spinal cord, with the expression being slightly higher in the EAE stage 3 spinal cord. In the EAE stage 3 spinal cord, cells in the white matter and perivascular cuffs, probably infiltrating macrophages and/or other leukocytes, showed signal which was absent in the normal spinal cord.

F. Mouse Embryos

In the day 11 embryo signal was apparent in the central nervous system in the fourth ventricle, which remained constant throughout the embryo time course as it developed into the cerebellum and brain stem. As the embryos matured, signal became apparent in central nervous system in the spinal cord (day 12), primary cortex and ganglion Gasseri (day 14), and hypophysis (day 16). Signal was observed in the peripheral nervous system (beginning on day 14 or 15) on nerves leaving the spinal cord, and, on day 17, strong signal appeared around the whiskers of the embryo. Expression was also seen in the liver and lung at day 14, the gut (beginning on day 15), and in the posterior portion of the mouth/throat (beginning on day 16). By day 18, the expression pattern had differentiated into signal in the cortex, hindbrain (cerebellum and brain stem), nerves leaving the lumbar region of the spinal cord, the posterior portion of the mouth/throat, the liver, the kidney, and possible weak signal in the lung and gut.

G. Summary

PAF-AH mRNA expression in the tonsil, thymus, lymph node, Peyer's patches, appendix, and colon lymphatic aggregates is consistent with the conclusions that the probable predominant in vivo source of PAF-AH is the macrophage because these tissues all are populated with tissue macrophages that serve as phagocytic and antigen-processing cells.

Expression of PAF-AH in inflamed tissues would be consistent with the hypothesis that a role of monocyte-derived macrophages is to resolve inflammation. PAF-AH would be expected to inactivate PAF and the pro-inflammatory phospholipids, thus down-regulating the inflammatory cascade of events initiated by these mediators.

PAF has been detected in whole brain tissue and is secreted by rat cerebellar granule cells in culture. In vitro and in vivo experiments have demonstrated that PAF binds a specific receptor in neural tissues and induces functional and phenotypic changes such as calcium mobilization, upregulation of transcription activating genes, and differentiation of the neural precursor cell line, PC12. These observations suggested a physiologic role for PAF in the brain, and consistent with this, recent experiments using hippocampal tissue section cultures and PAF analogs and antagonists have implicated PAF as an important retrograde messenger in hippocampal long term potentiation. Therefore, in addition to its pathological effect in inflammation, PAF appears to participate in routine neuronal signalling processes. Expression of the extracellular PAF-AH in the brain may serve to regulate the duration and magnitude of PAF-mediated signalling.

EXAMPLE 13

Monoclonal antibodies specific for recombinant human plasma PAF-AH were generated using *E. coli* produced PAF-AH as an immunogen.

Mouse #1342 was injected on day 0, day 19, and day 40 with recombinant PAF-AH. For the prefusion boost, the mouse was injected with the immunogen in PBS, four days later the mouse was sacrificed and its spleen removed sterilely and placed in 10 ml serum free RPMI 1640. A single-cell suspension was formed by grinding the spleen between the frosted ends of two glass microscope slides submerged in serum free RPMI 1640, supplemented with 2 mM L-glutamine, 1 mM sodium pyruvate, 100 units/ml penicillin, and 100 $\mu$g/ml streptomycin (RPMI) (Gibco, Canada). The cell suspension was filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from 3 naive Balb/c mice were prepared in a similar manner. NS-1 myeloma cells, kept in log phase in RPMI with 11% fetal bovine serum (FBS) (Hyclone Laboratories, Inc., Logan, Utah) for three days prior to fusion, were centrifuged at 200 g for 5 minutes, and the pellet was washed twice as described in the foregoing paragraph.

One×10$^8$ spleen cells were combined with 2.0×10$^7$ NS-1 cells, centrifuged and the supernatant was aspirated. The cell pellet was dislodged by tapping the tube and 1 ml of 37° C. PEG 1500 (50% in 75 mM Hepes, pH 8.0) (Boehringer Mannheim) was added with stirring over the course of 1 minute, followed by adding 7 ml of serum free RPMI over 7 minutes. An additional 8 ml RPMI was added and the cells were centrifuged at 200 g for 10 minutes. After discarding the supernatant, the pellet was resuspended in 200 ml RPMI containing 15% FBS, 100 $\mu$M sodium hypoxanthine, 0.4 $\mu$M aminopterin, 16 $\mu$M thymidine (HAT) (Gibco), 25 units/ml IL-6 (Boehringer Mannheim) and 1.5×10$^6$ thymocytes/m and plated into 10 Corning flat bottom 96 well tissue culture plates (Coming, Corning N.Y.).

On days 2, 4, and 6, after the fusion, 100 $\mu$l of medium was removed from the wells of the fusion plates and replaced with fresh medium. On day 8, the fusion was screened by ELISA, testing for the presence of mouse IgG binding to recombinant PAF-AH. Immulon 4 plates (Dynatech, Cambridge, Mass.) were coated for 2 hours at 37° C. with 100 ng/well recombinant PAF-AH diluted in 25 mM TRIS, pH 7.5. The coating solution was aspirated and 200$\mu$l/well of blocking solution [0.5% fish skin gelatin (Sigma) diluted in CMF-PBS] was added and incubated for 30 minutes at 37° C. Plates were washed three times with PBS with 0.05% Tween 20 (PBST) and 50 $\mu$l culture supernatant was added. After incubation at 37° C. for 30 minutes, and washing as above, 50 $\mu$l of horseradish peroxidase conjugated goat anti-mouse IgG(fc) (Jackson ImmunoResearch, West Grove, Pa.) diluted 1:3500 in PBST was added. Plates were incubated as above, washed four times with PBST and 100 $\mu$L substrate, consisting of 1 mg/ml o-phenylene diamine (Sigma) and 0.1 $\mu$l/ml 30% H$_2$O$_2$ in 100 mM Citrate, pH 4.5, was added. The color reaction was stopped in 5 minutes with the addition of 50 $\mu$l of 15% H$_2$SO$_4$. A$_{490}$ was read onn a plate reader (Dynatech).

Selected fusion wells were cloned twice by dilution into 96 well plates and visually scoring the number of colonies/well after 5 days. Hybridomas cloned were 90D1E, 90E3A, 90E6C, 90G11D (ATCC HB 11724), and 90F2D (ATCC HB 11725).

The monoclonal antibodies produced by hybridomas were isotyped using the Isostrip system (Boehringer Mannheim, Indianapolis, Ind.). Results showed that the monoclonal antibodies produced by hybridomas from fusion 90 were all IgG$_1$.

All of the monoclonal antibodies produced by hybridomas from fusion 90 functioned well in ELISA assays but were unable to bind PAF-AH on Western blots. To generate antibodies that could recognize PAF-AH by Western, mouse #1958 was immunized with recombinant enzyme. Hybridomas were generated as described for fusion 90 but were screened by Western blotting rather than ELISA to identify Western-competent clones.

For Western analyses, recombinant PAF-AH was mixed with an equal volume of sample buffer containing 125 mM Tris, pH 6.8, 4% SDS, 100 mM dithiothreitol and 0.05% bromphenol blue and boiled for five minutes prior to loading onto a 12% SDS polyacrylamide gel (Novex). Following electrophoresis at 40 mAmps, proteins were electrotransferred onto a polyvinylidene fluoride membrane (Pierce) for 1 hour at 125 V in 192 mM glycine, 25 mM Tris base, 20% methanol, and 0.01% SDS. The membrane was incubated in 20 mM Tris, 100 mM NaCl (TBS) containing 5% bovine serum albumin (BSA, Sigma) overnight at 4° C. The blot was incubated 1 hour at room temperature with rabbit polyclonal antisera diluted 1/8000 in TBS containing 5% BSA, and then washed with TBS and incubated with alkaline phosphatase-conjugated goat anti-mouse IgG in TBS containing 5% BSA for 1 hour at room temperature. The blot was again washed with TBS then incubated with 0.02% 5-bromo-4-chloro-3-indolyl phosphate and 0.03% nitroblue tetrazolium in 100 mM Tris-HCl, pH 9.5, 100 mM NaCl, and 5 mM MgCl$_2$. The reaction was stopped with repeated water rinses.

Selected fusion wells, the supernatants of which were positive in Western analyses, were processed as described above. Hybridoma 143A reacted with PAF-AH in Western blots and was cloned (ATCC HB 11900).

Polyclonal antisera specific for human plasma PAF-AH was raised in rabbits by three monthly immunizations with 100 $\mu$g of purified recombinant enzyme in Fruend's adjuvant.

EXAMPLE 14

Experimental studies were performed to evaluate the in vivo therapeutic effects of recombinant PAF-AH of the invention on acute inflammation using a rat foot edema model [Henriques et al., *Br. J. Pharmacol.*, 106: 579–582 (1992)]. The results of these studies demonstrated that rPAF-AH blocks PAF-induced edema. Parallel studies were done to compare the effectiveness of PAF-AH with two commercially available PAF antagonists.

A. Preparation of PAF-AH

*E. coli* transformed with the PAF-AH expression vector puc trp AH were lysed in a microfluidizer, solids were centrifuged out and the cell supernatants were loaded onto a S-Sepharose column (Pharmacia). The column was washed extensively with buffer consisting of 50 mM NaCl, 10 mM CHAPS, 25 mM MES and 1 mM EDTA, pH 5.5. PAF-AH was eluted by increasing the NaCl concentration of the buffer to 1M. Affinity chromatography using a Blue Sepharose column (Pharmacia) was then used as an additional purification step. Prior to loading the PAF-AH preparation on the Blue Sepharose column, the sample was diluted 1:2 to reduce the NaCl concentration to 0.5M and the pH was adjusted to 7.5. After washing the Blue Sepharose column extensively with buffer consisting of 0.5M NaCl, 25 mM tris, 10 mM CHAPS and 1 mM EDTA, pH 7.5 the PAF-AH was eluted by increasing the NaCl concentration to 3.0M.

Purity of PAF-AH isolated in this manner was generally 95% as assessed by SDS-PAGE with activity in the range of 5000–10,000 U/ml. Additional quality controls done on each PAF-AH preparation included determining endotoxin levels and hemolysis activity on freshly obtained rat erythrocytes. A buffer containing 25 mM Tris, 10 mM CHAPS, 0.5M NaCl, pH 7.5 functioned as storage media of the enzyme as well as carrier for administration. Dosages used in experiments were based on enzyme activity assays conducted immediately prior to experiments.

B. Induction of Edema

Six to eight-week-old female Long Evans rats (Charles River, Wilmington, Mass.), weighing 180–200 grams, were used for all experiments. Prior to experimental manipulations, animals were anesthetized with a mixture of the anesthetics Ketaset (Fort Dodge Laboratories, Fort Dodge, Iowa), Rompun (Miles, Shawnee Mission, Kans.), and Ace promazine (Aveco, Fort Dodge, Iowa) administered subcutaneously at approximately 2.5 mg Ketaset, 1.6 mg Rompun, 0.2 mg Ace Promazine per animal per dose. Edema was induced in the foot by administration of either PAF or zymosan as follows. PAF (Sigma #P-1402) was freshly prepared for each experiment from a 19.1 mM stock solution stored in chloroform/methanol (9:1) at $-20°$ C. Required volumes were dried down under $N_2$, diluted 1:1000 in a buffer containing 150 mM NaCl, 10 mM Tris pH 7.5, and 0.25% BSA, and sonicated for five minutes. Animals received 50 $\mu$l PAF (final dose of 0.96 nmoles) subcutaneously between the hind foot pads, and edema was assessed after 1 hour and again after 2 hours in some experiments. Zymosan A (Sigma #A-8800) was freshly prepared for each experiment as a suspension of 10 mg/ml in PBS. Animals received 50 $\mu$l of zymosan (final dose of 500 $\mu$g) subcutaneously between the hind foot pads and edema was assessed after 2 hours.

Edema was quantitated by measuring the foot volume immediately prior to administration of PAF or zymosan and at indicated time point post-challenge with PAF or zymosan. Edema is expressed as the increase in foot volume in milliliters. Volume displacement measurements were made on anesthetized animals using a plethysmometer (UGO Basile, model #7150) which measures the displaced water volume of the immersed foot. In order to insure that foot immersion was comparable from one time point to the next, the hind feet were marked in indelible ink where the hairline meets the heel. Repeated measurements of the same foot using this technique indicate the precision to be within 5%.

C. PAF-AH Administration Routes and Dosages

PAF-AH was injected locally between the foot pads, or systematically by IV injection in the tail vein. For local administration rats received 100 $\mu$l PAF-AH (4000–6000 U/ml) delivered subcutaneously between the right hind foot pads. Left feet served as controls by administration of 100 $\mu$l carrier (buffered salt solution). For systemic administration of PAF-AH, rats received the indicated units of PAF-AH in 300 $\mu$l of carrier administered IV in the tail vein. Controls received the appropriate volume of carrier IV in the tail vein.

D. Local Administration of PAF-AH

Figure 6:
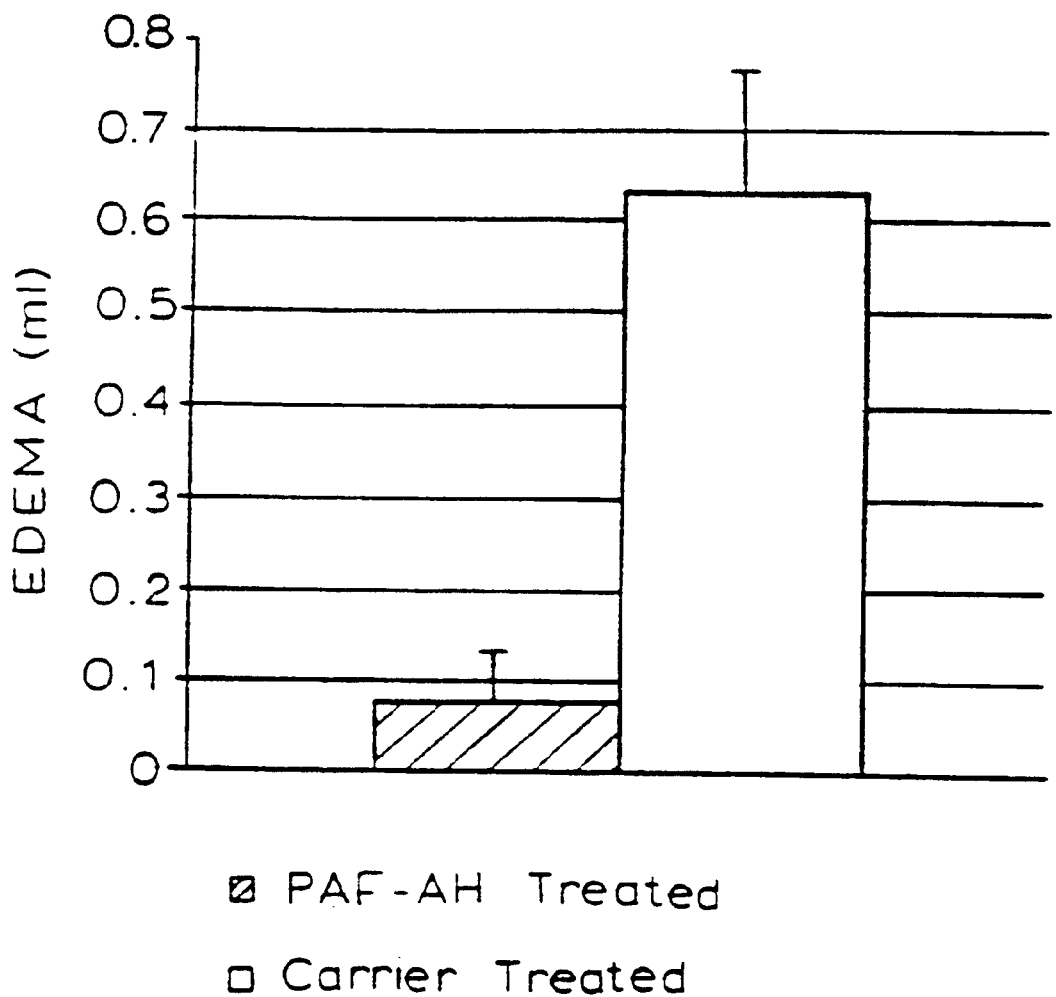
FIG. 6 is a bar graph illustrating blockage of PAF-induced rat foot edema by locally administered recombinant PAF-AH of the invention.

Rats (N=4) were injected with 100 $\mu$l of PAF-AH (4000–6000 U/ml) subcutaneously between the right foot pads. Left feet were injected with 100 $\mu$l carrier (buffered salt solution). Four other rats were injected only with carrier. All rats were immediately challenged with PAF via subcutaneous foot injection and foot volumes assessed 1 hour post-challenge. FIG. 6, wherein edema is expressed as average increase in foot volume (ml)±SEM for each treatment group, illustrates that PAF-induced foot edema is blocked by local administration of PAF-AH. The group which received local PAF-AH treatment prior to PAF challenge showed reduced inflammation compared to the control injected group. An increase in foot volume of 0.08 ml±0.08 (SEM) was seen in the PAF-AH group as compared to 0.63±0.14 (SEM) for the carrier treated controls. The increase in foot volume was a direct result of PAF injection as animals injected in the foot only with carrier did not exhibit an increase in foot volume.

E. Intravenous Administration of PAF-AH

Figure 7:
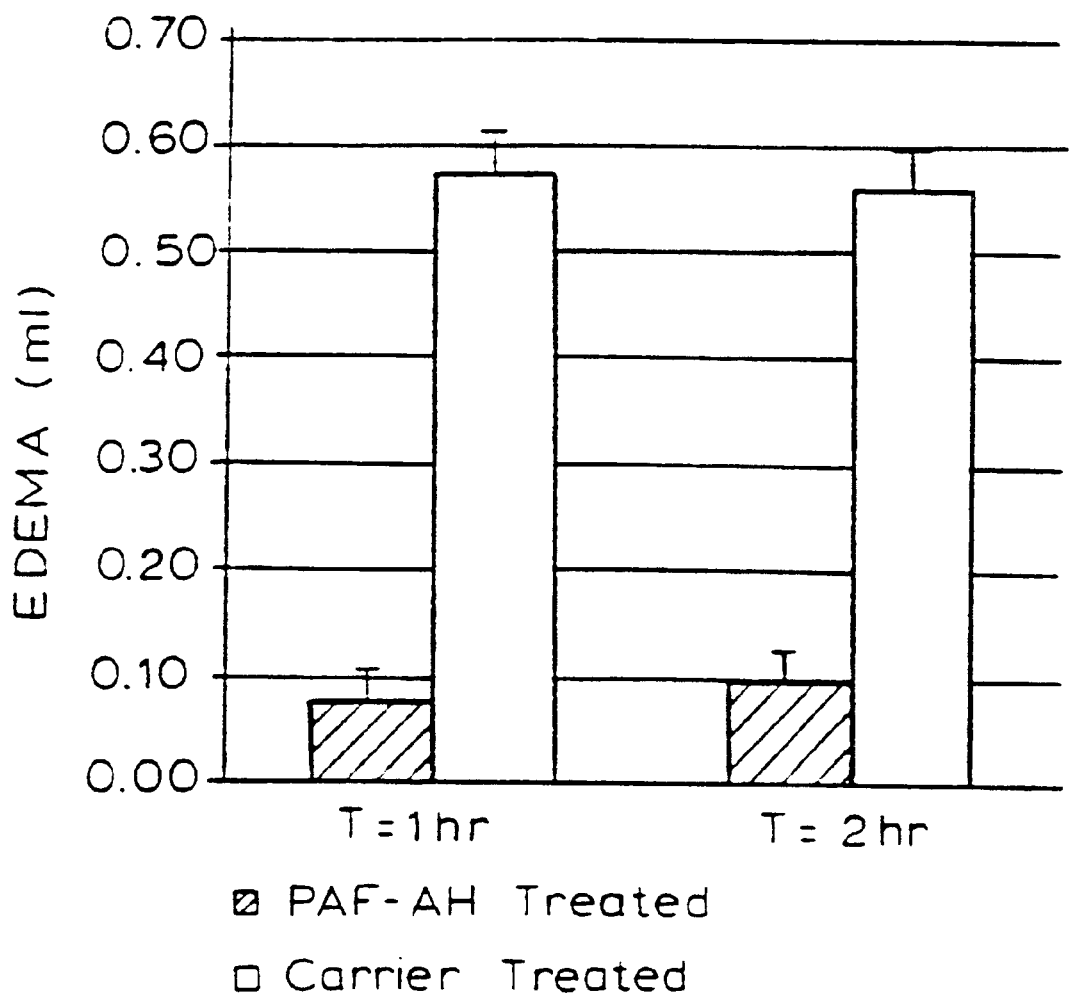
FIG. 7 is a bar graph illustrating blockage of PAF-induced rat foot edema by intravenously administered PAF-AH.

Rats (N=4 per group) were pretreated IV with either PAF-AH (2000 U in 300 $\mu$l carrier) or carrier alone. 15 minutes prior to PAF challenge. Edema was assessed 1 and 2 hours after PAF challenge. FIG. 7, wherein edema is expressed as average increase in volume (ml)±SEM for each treatment group, illustrates that IV administration of PAF-AH blocked PAF induced foot edema at one and two hours post challenge. The group which received 2000 U of PAF-AH given by the IV route showed a reduction in inflammation over the two hour time course. Mean volume increase for the PAF-AH treated group at two hours was 0.10 ml±0.08 (SEM), versus 0.56 ml±0.11 for carrier treated controls.

F. Comparison of PAF-AH Protection in Edema Induced by PAF or Zymosan

Figure 8:
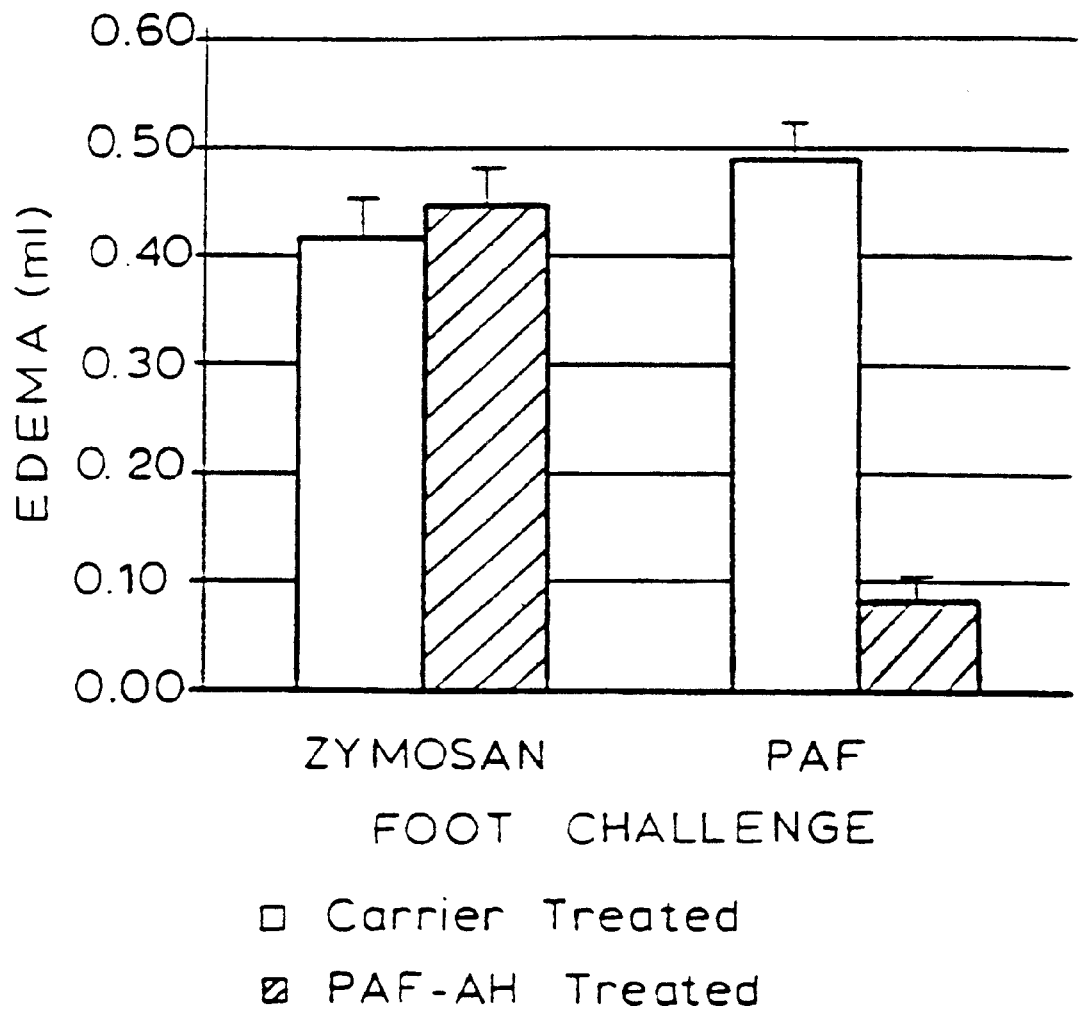
FIG. 8 is a bar graph showing that PAF-AH blocks PAF-induced edema but not zymosan A-induced edema.

Rats (N=4 per group) were pretreated IV with either PAF-AH (2000 U in 300 $\mu$l carrier) or carrier alone. Fifteen minutes after pretreatment, groups received either PAF or zymosan A, and foot volume was assessed after 1 and 2 hours, respectively. As shown in FIG. 8, wherein edema is expressed as average increase in volume (ml)±SEM for each treatment group, systemic administration of PAF-AH (2000 U) was effective in reducing PAF-induced foot edema, but failed to block zymosan induced edema. A mean increase in volume of 0.08±0.02 was seen in the PAF-AH treated group versus 0.49±0.03 for the control group.

G. Effective Dose Titration of PAF-AH Protection

Figure 9A:
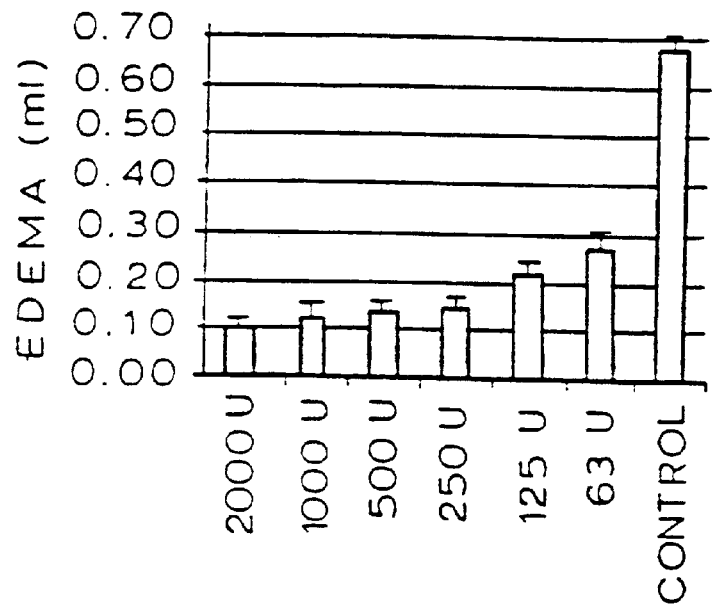
FIGS. 9A and 9B present dose response results of PAF-AH anti-inflammatory activity in rat food edema.
Figure 9B:
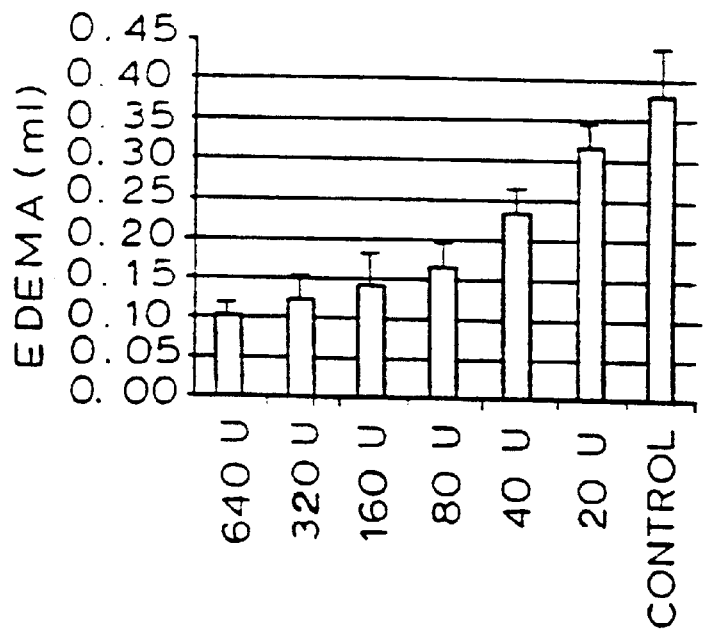

In two separate experiments, groups of rats (N=3 to 4 per group) were pretreated IV with either serial dilutions of PAF-AH or carrier control in a 300 $\mu$l volume, 15 minutes prior to PAF challenge. Both feet were challenged with PAF (as described above) and edema was assessed after 1 hour. FIG. 9 wherein edema is expressed as average increase in volume (ml)±SEM for each treatment group, illustrates the increase in protection from PAF-induced edema in rats injected with increasing dosages of PAF-AH. In the experiments, the $ID_{50}$ of PAF-AH given by the IV route was found to be between 40 and 80 U per rat.

H. In Vivo Efficacy of PAF-AH as a Function of Time After Administration

Figure 10A:
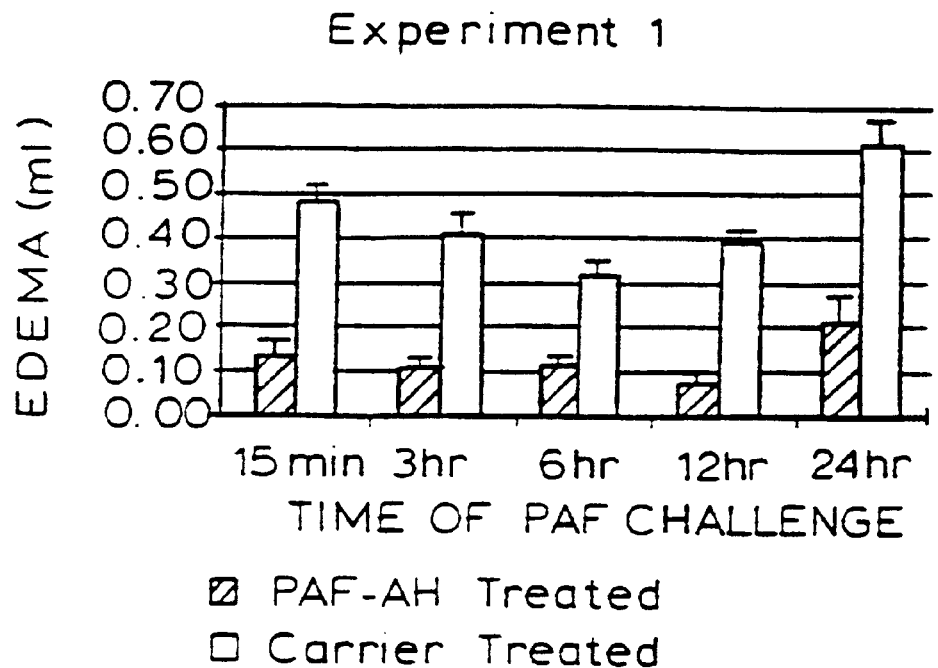
FIGS. 10A and 10B present results indicating the in vivo efficacy of a single dose of PAF-AH over time.
Figure 10B:
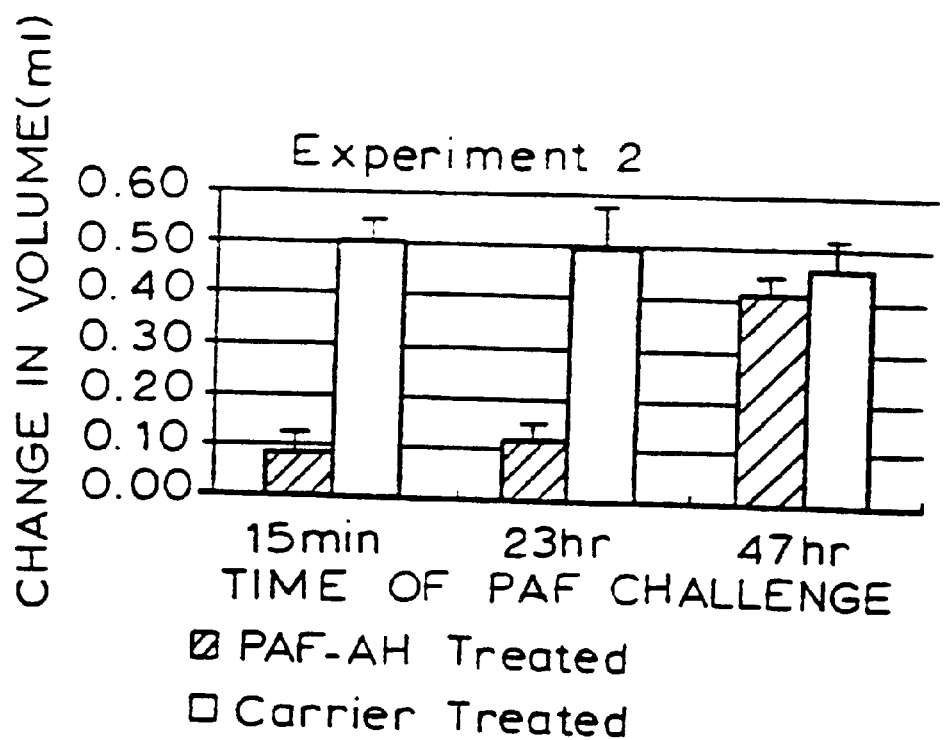

In two separate experiments, two groups of rats (N=3 to 4 per group) were pretreated IV with either PAF-AH (2000 U in 300 µl carrier) or carrier alone. After administration, groups received PAF at time points ranging from 15 minutes to 47 hours post PAF-AH administration. Edema was then assessed 1 hour after PAF challenge. As shown in FIG. 10, wherein edema is expressed as average increase in volume (ml)±SEM for each treatment group, administration of 2000 U of PAF-AH protects rats from PAF induced edema for at least 24 hours.

I. Pharmacokinetics of PAF-AH

Figure 11:
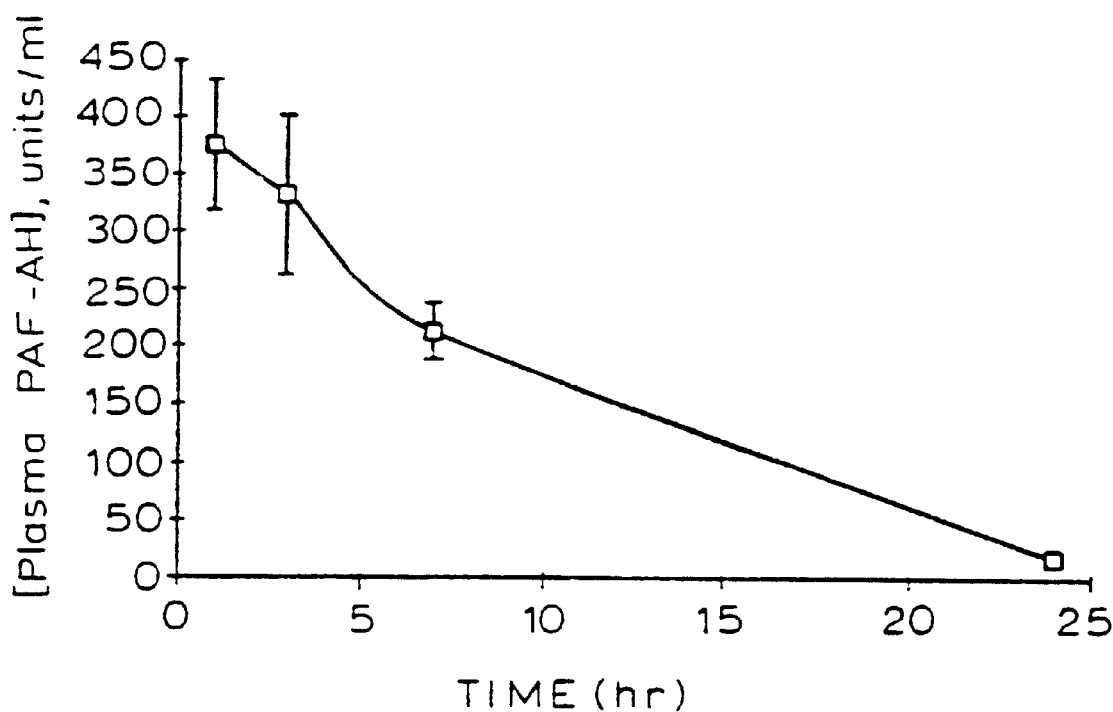
FIG. 11 is a line graph representing the pharmacokinetics of PAF-AH in rat circulation.

Four rats received 2000 U of PAF-AH by IV injection in a 300 µl volume. Plasma was collected at various time points and stored at 4° C. and plasma concentrations of PAF-AH were determined by ELISA using a double mAb capture assay. In brief, monoclonal antibody 90G11D (Example 13) was diluted in 50 mM carbonate buffer pH 9.6 at 100 ng/ml and immobilized on Immulon 4 ELISA plates overnight at 4° C. After extensive washing with PBS containing 0.05% Tween 20, the plates were blocked for 1 hour at room temperature with 0.5% fish skin gelatin (Sigma) diluted in PBS. Serum samples diluted in PBS with 15 mM CHAPS were added in duplicate to the washed ELISA plate and incubated for 1 hour at room temperature. After washing, a biotin conjugate of monoclonal antibody 90F2D (Example 13) was added to the wells at a concentration of 5 µg/ml diluted in PBS and incubated for 1 hour at room temperature. After washing, 50 µl of a 1:1000 dilution of ExtraAvidin (Sigma) was added to the wells and incubated for 1 hour at room temperature. After washing, wells were developed using OPD as a substrate and quantitated. Enzyme activity was then calculated from a standard curve. FIG. 11, wherein data points represent means±SEM, shows that at one hour plasma enzyme levels approached the predicted concentration based on a 5–6 ml plasma volume for 180–200 gram rats, mean=374 U/ml±58.2. Beyond one hour plasma levels steadily declined, reaching a mean plasma concentration of 19.3 U/ml±3.4 at 24 hours, which is still considerably higher than endogenous rat PAF-AH levels which have been found to be approximately 4 U/ml by enzymatic assays.

J. Effectiveness of PAF-AH Versus PAF Antagonists

Figure 12:
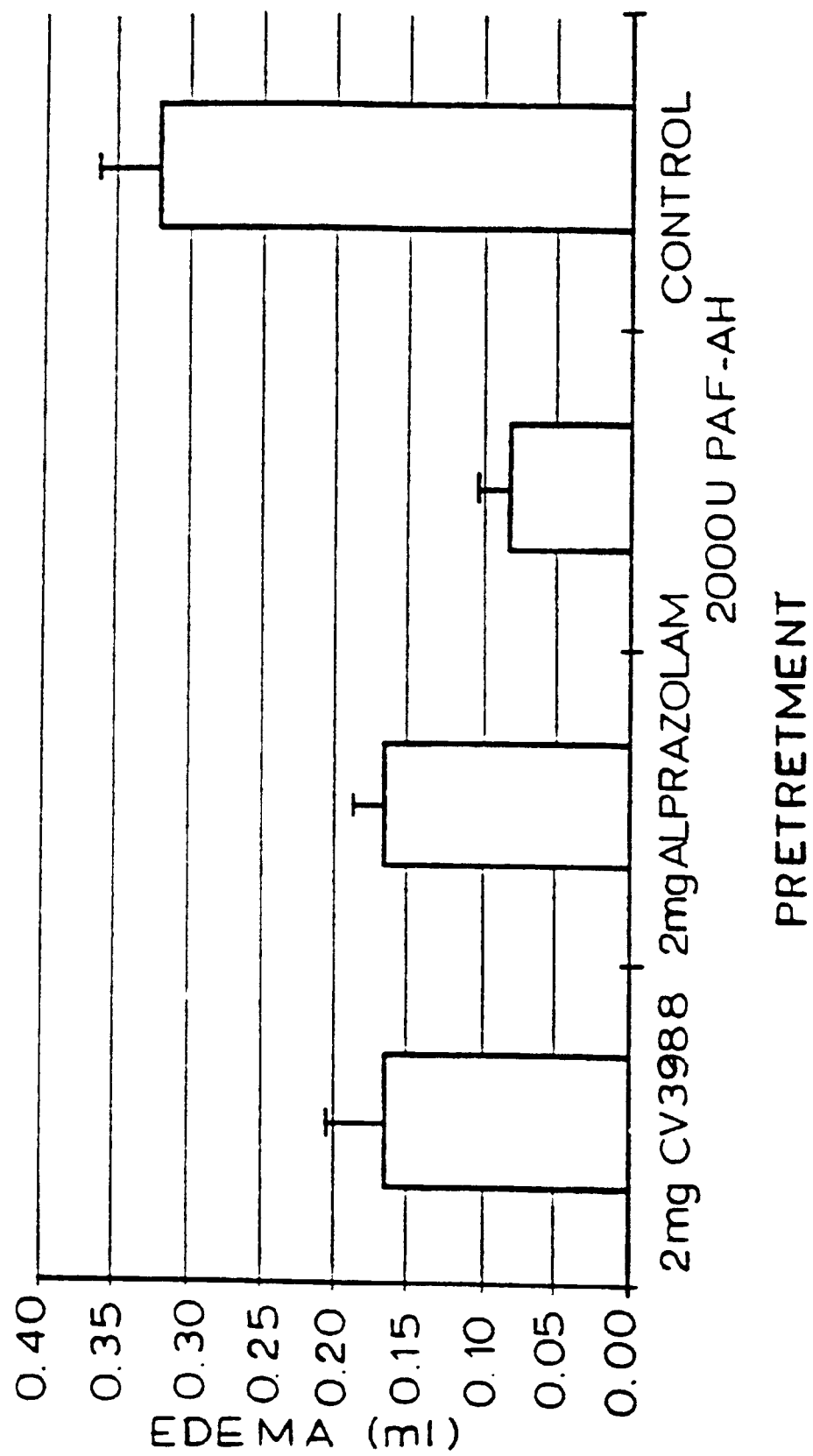
FIG. 12 is a bar graph showing the anti-inflammatory effects of PAF-AH in comparison to the lesser effects of PAF antagonists in rat foot edema.

Groups of rats (N=4 per group) were pretreated with one of three potential antiinflammatories: the PAF antagonist CV3988 (Biomol #L-103) administered IP (2 mg in 200 µl EtOH), the PAF antagonist Alprazolam (Sigma #A-8800) administered IP (2 mg in 200 µl EtOH), or PAF-AH (2000 U) administered IV. Control rats were injected IV with a 300 µl volume of carrier. The PAF antagonists were administered IP because they are solubilized in ethanol. Rats injected with either CV3988 or Alprazolam were challenged with PAF 30 minutes after administration of the PAF antagonist to allow the PAF antagonist to enter circulation, while PAF-AH and carrier-treated rats were challenged 15 minutes after enzyme administration. Rats injected with PAF-AH exhibited a reduction in PAF-induced edema beyond that afforded by the established PAF antagonists CV3988 and Alprazolam. See FIG. 12 wherein edema is expressed as average increase in volume (ml)±SEM for each treatment group.

In summary, rPAF-AH is effective in blocking edema mediated by PAF in vivo. Administration of PAF-AH products can be either local or systemic by IV injection. In dosing studies, IV injections in the range of 160–2000 U/rat were found to dramatically reduce PAF mediated inflammation, while the $ID_{50}$ dosage appears to be in the range of 40–80 U/rat. Calculations based on the plasma volume for 180–200 gram rats predicts that a plasma concentration in the range of 25–40 U/ml should block PAF-elicited edema. These predictions are supported by preliminary pharmacokinetic studies. A dosage of 2000 U of PAF-AH was found to be effective in blocking PAF mediated edema for at least 24 hours. At 24 hours following administration of PAF-AH plasma concentrations of the enzyme were found to be approximately 25 U/ml. PAF-AH was found to block PAF-induced edema more effectively than the two known PAF antagonists tested.

Collectively, these results demonstrate that PAF-AH effectively blocks PAF induced inflammation and may be of therapeutic value in diseases where PAF is the primary mediator.

EXAMPLE 15

Recombinant PAF-AH of the invention was tested in a second in vivo model, PAF-induced pleurisy. PAF has previously been shown to induce vascular leakage when introduced into the pleural space [Henriques et al., supra]. Female rats (Charles River, 180–200 g) were injected in the tail vein with 200 µl of 1% Evans blue dye in 0.9% with 300 µl recombinant PAF-AH (1500 µmol/ml/hour, prepared as described in Example 14) or with an equivalent volume of control buffer. Fifteen minutes later the rats received an 100 µl injection of PAF (2.0 mol) into the pleural space. One hour following PAF challenge, rats were sacrificed and the pleural fluid was collected by rinsing the cavity with 3 ml heparinized phosphate buffered saline. The degree of vascular leak was determined by the quantity of Evans blue dye in the pleural space which was quantitated by absorbance at 620 nm. Rats pretreated with PAF-AH were found to have much less vascular leakage than control animals (representing more than an 80% reduction in inflammation).

The foregoing results support the treatment of subjects suffering from pleurisy with recombinant PAF-AH enzyme of the invention.

EXAMPLE 16

Recombinant PAF-AH enzyme of the invention was also tested for efficacy in a model of antigen-induced eosinophil recruitment. The accumulation of eosinophils in the airway is a characteristic feature of late phase immune responses which occur in asthma, rhinitis and eczema. BALB/c mice (Charles River) were sensitized by two intraperitoneal injections consisting of 1 µg of ovalbumin (OVA) in 4 mg of aluminum hydroxide (Imject alum, Pierce Laboratories, Rockford, Ill.) given at a 2 week interval. Fourteen days following the second immunization, the sensitized mice were challenged with either aerosolized OVA or saline as a control.

Prior to challenge mice were randomly placed into four groups, with four mice/group. Mice in groups 1 and 3 were pretreated with 140 µl of control buffer consisting of 25 mM tris, 0.5M NaCl, 1 mM EDTA and 0.1% Tween 80 given by intravenous injection. Mice in groups 2 and 4 were pretreated with 750 units of PAF-AH (activity of 5,500 units/ml given in 140 µl of PAF-AH buffer). Thirty minutes following administration of PAF-AH or buffer, mice in groups 1 and 2 were exposed to aerosolized PBS as described below, while mice in groups 3 and 4 were exposed to aerosolized OVA.

Twenty-four hours later mice were treated a second time with either 140 μl of buffer (groups 1 and 3) or 750 units of PAF-AH in 140 μl of buffer (groups 2 and 4) given by intravenous injection.

Eosinophil infiltration of the trachea was induced in the sensitized mice by exposing the animals to aerosolized OVA. Sensitized mice were placed in 50 ml conical centrifuge tubes (Corning) and forced to breath aerosolized OVA (50 mg/ml) dissolved in 0.9% saline for 20 minutes using a nebulizer (Model 646, DeVilbiss Corp., Somerset, Pa.). Control mice were treated in a similar manner with the exception that 0.9% saline was used in the nebulizer. Forty-eight hours following the exposure to aerosolized OVA or saline, mice were sacrificed and the tracheas were excised. Tracheas from each group were inbeded in OCT and stored at −70° until sections were cut.

To evaluate eosinophil infiltration of the trachea, tissue sections from the four groups of mice were stained with either Luna solution and hematoxylin-eosin solution or with peroxidase. Twelve 6 μm thick sections were cut from each group of mice and numbered accordingly. Odd numbered sections were stained with Luna stain as follows. Sections were fixed in formal-alcohol for 5 minutes at room temperature, rinsed across three changes of tap water for 2 minutes at room temperature then rinsed in two changed of $dH_2O$ for 1 minute at room temperature. Tissue sections were stained with Luna stain 5 minutes at room temperature (Luna stain consisting of 90 ml Weigert's Iron hematoxylin and 10 ml of 1% Biebrich Scarlet). Stained slides were dipped in 1% acid alcohol six times, rinsed in tap water for 1 minute at room temperature, dipped in 0.5% lithium carbonate solution five times and rinsed in running tap water for 2 minutes at room temperature. Slides were dehydrated across 70%–95%–100% ethanol 1 minute each, at room temperature, then cleared in two changes of xylene for 1 minute at room temperature and mounted in Cytoseal 60.

For the peroxidase stain, even numbered sections were fixed in 4° C. acetone for 10 minutes and allowed to air dry. Two hundred μl of DAB solution was added to each section and allowed to sit 5 minutes at room temperature. Slides were rinsed in tap water for 5 minutes at room temperature and 2 drops of 1% osmic acid was applied to each section for 3–5 seconds. Slides were rinsed in tap water for 5 minutes at room temperature and counterstained with Mayers hematoxylin at 25° C. at room temperature. Slides were then rinsed in running tap water for 5 minutes and dehydrated across 70%–95%–100% ethanol 1 minute each at room temperature. Slides were cleared through two changes of xylene for 1 minute each at room temperature and mounted in Cytoseal 60.

The number of eosinophils in the submucosal tissue of the trachea was evaluated. Trachea from mice from groups 1 and 2 were found to have very few eosinophils scattered throughout the submucosal tissue. As expected tracheas from mice in group 3, which were pretreated with buffer and exposed to nebulized OVA, were found to have large numbers of eosinophils throughout the submucosal tissue. In contrast, the tracheas from mice in group 4, which were pretreated with PAF-AH and exposed to nebulized OVA were found to have very few eosinophils in the submucosal tissue comparable to what was seen in the two control groups, groups 1 and 2.

Thus, therapeutic treatment with PAF-AH of subjects exhibiting a late phase immune response involving the accumulation of eosinophils in the airway, such as that which occurs in asthma and rhinitis is indicated.

EXAMPLE 17

A PAF-AH product of the invention was also tested in two different rat models for treatment of necrotizing enterocolitis (NEC), an acute hemorrhagic necrosis of the bowel which occurs in low birth weight infants and causes a significant morbidity and mortality. Previous experiments have demonstrated that treatment with glucocorticoids decreases the incidence of NEC in animals and in premature infants, and the activity of glucocorticoids has been suggested to occur via an increase in the activity of plasma PAF-AH.

A. Activity in Rats With NEC Induced by PAF Challenge

1. Prevention of NEC

A recombinant PAF-AH product, rPH.2 (25,500 units in 0.3 ml, groups 2 and 4), or vehicle/buffer alone (25 mM tris, 0.5M NaCl, 1 mM EDTA and 0.1% Tween 80) (groups 1 and 3) was administered into the tail veins of female Wistar rats (n=3) weighing 180–220 grams. Either BSA (0.25%) saline (groups 1 and 2) or PAF (0.2 μg/100 gm) suspended in BSA saline (groups 3 and 4) was injected into the abdominal aorta at the level of the superior mesenteric artery 15 minutes after rPH.2 or vehicle injection as previously described by Furukawa, et al. [*J. Pediatr.Res.* 34:237–241 (1993)]. The small intestines were removed after 2 hours from the ligament of Trietz to the cecum, thoroughly washed with cold saline and examined grossly. Samples were obtained from microscopic examination from the upper, middle and lower portions of the small intestine. The tissues were fixed in buffered formalin and the sample processed for microscopic examination by staining with hematoxylin and eosin. The experiment was repeated three times.

Gross findings indicated a normal appearing bowel in groups treated with the vehicle of BSA saline. Similarly, rPH.2 injected in the absence of PAF had no effect on the gross findings. In contrast, the injection of PAF into the descending aorta resulted in rapid, severe discoloration and hemorrhage of the serosal surface of the bowel. A similar hemorrhage was noted when a section of the small bowel was examined on the mucosal side and the intestine appeared to be quite necrotic. When rPH.2 was injected via the tail vein 15 minutes prior to the administration of PAF into the aorta, the bowel appeared to be normal.

Upon microscopic examination, the intestine obtained from groups 1, 2 and 4 demonstrated a normal villous architecture and a normal population of cells within the lamina propria. In contrast, the group treated with PAF alone showed a full thickness necrosis and hemorrhage throughout the entire mucosa.

The plasma PAF-AH activities were also determined in the rats utilized in the experiment described above. PAF-AH activity was determined as follows. Prior to the tail vein injection, blood samples were obtained. Subsequently blood samples were obtained from the vena cava just prior to the injection of PAF and at the time of sacrifice. Approximately 50 μl of blood was collected in heparinized capillary tubes. The plasma was obtained following centrifugation (980×g for 5 minutes). The enzyme was assayed as previously described by Yasuda and Johnston *Endocrinology*, 130:708–716 (1992).

The mean plasma PAF-AH activity of all rats prior to injection was found to be 75.5±2.5 units (1 unit equals 1 nmoles×min$^{-1}$×ml$^{-1}$ plasma). The mean plasma PAF-AH activities 15 minutes following the injection of the vehicle were 75.2±2.6 units for group 1 and 76.7±3.5 units for group 3. After 15 minutes, the plasma PAF-AH activity of the animals injected with 25,500 units rPH.2 was 2249±341 units for group 2 and 2494±623 units for group 4. The activity of groups 2 and 4 remained elevated (1855±257 units) until the time of sacrifice (2¼ hours after rPH.2 injection) (Group 2=1771±308; Group 4=1939±478). These results indicate that plasma PAF-AH activity of the rats which were injected with the vehicle alone (groups 1 and 3) did not change during the course of the experiment. All the animals receiving the PAF injection alone developed NEC while all rats that were injected with rPH.2 followed by PAF injection were completely protected.

2. Dose-Dependency of Prevention of NEC

In order to determine if the protection against NEC in rats was dose dependent, animals were treated with increasing doses of rPH.2 15 minutes prior to PAF administration. Initially, rPH.2, ranging from 25.5 to 25,500 units were administered into the tail vein of rats. PAF (0.4 μg in 0.2 ml of BSA-saline) was subsequently injected into the abdominal aorta 15 minutes after the administration of rPH.2. The small intestine was removed and examined for NEC development 2 hours after PAF administration. Plasma PAF-AH activity was determined prior to the exogenous administration of the enzyme, and 15 minutes and 2¼ hours after rPH.2 administration. The results are the mean of 2–5 animals in each group.

Gross findings indicated that all rats receiving less than 2,000 units of the enzyme developed NEC. Plasma PAF-AH activity in animals receiving the lowest protective amount of enzyme (2040 units) was 363 units per ml of plasma after 15 minutes, representing a five-fold increase over basal levels. When rPH.2 was administered at less than 1,020 total units, resultant plasma enzyme activity averaged approximately 160 or less, and all animals developed NEC.

3. Duration of Protection Against NEC

In order to determine the length of time exogenous PAF-AH product afforded protection against development of NEC, rats were injected once with a fixed amount of the enzyme via the tail vein and subsequently challenged with PAF at various time points. rPH.2 (8,500 units in 0.3 ml) or vehicle alone was administered into the tail vein of rats, and PAF (0.36 μg in 0.2 ml of BSA-saline) was injected into the abdominal aorta at various times after the enzyme administration. The small intestines were removed 2 hours after the PAF injection for gross and histological examinations in order to evaluate for NEC development. Plasma PAF-AH activities were determined at various times after enzyme administration and two hours after PAF administration. The mean value±standard error for enzyme activity was determined for each group.

Results indicated that none of the rats developed NEC within the first eight hours after injection of rPH.2, however 100% of the animals challenged with PAF at 24 and 48 hours following injection of the enzyme developed NEC.

4. Reversal of NEC

In order to determine if administration of PAF-AH product was capable of reversing development of NEC induced by PAF injection, 25,500 units of enzyme was administered via injection into the vena cava two minutes following PAF administration (0.4 μg). None of the animals developed NEC. However, when rPH.2 was administered via this route 15 minutes after the PAF injection, all animals developed NEC, consistent with the rapid time course of NEC development as induced by the administration of PAF previously reported Furukawa et al. [supra].

The sum of these observations indicate that a relatively small (five-fold) increase in the plasma PAF-AH activity is capable of preventing NEC. These observations combined with previous reports that plasma PAF-AH activity in fetal rabbits [Maki, et al., *Proc.Natl.Acad.Sci.* (USA) 85:728–732 (1988)] and premature infants [Caplan, et al., *J. Pediatr.* 116:908–964 (1990)] has been demonstrated to be relatively low suggests that prophylactic administration of human recombinant PAF-AH products to low birth weight infants may be useful in treatment of NEC.

B. Activity in a Neonatal Model of NEC

The efficacy of a PAF-AH product, rPH.2, was evaluated as follows in an NEC model in which newborn rats are stressed by formula feeding and asphyxia, two common risk factors for the disease in humans. In this model, approximately 70–80% of the animals develop gross and microscopic intestinal injury similar to neonatal NEC by the third day of life. Newborn rats were obtained from pregnant Sprague-Dawley rats (Harlan Sprague-Dawley, Indianapolis, Ind.) that were anesthetized with $CO_2$ and delivered via abdominal incision. Newborn animals were collected, dried, and maintained in a neonatal incubator during the entire experiment.

First, separate groups of animals were used to assess the dosing and absorption characteristics of rPH.2. Normal newborn rat pups were given one of three different enteral or intraperitoneal doses of rPH.2 (3λ, 15λ, or 75λ) at time 0, and blood was collected at 1 hour, 6 hours, or 24 hours later for assessment of plasma PAF-AH activity. PAF-AH activity was measured using a substrate incubation assay [Gray et al., *Nature*, 374:549 (1995)] and an ELISA utilizing an anti-human rPAF-AH monoclonal antibody for each sample (90F2D and 90G11D, described in Example 13). For selected samples, immunohistochemical analysis was performed using two different monoclonal antibodies developed against human rPAF-AH (90F2D and 90G11D, described in Example 13). Immunohistochemistry was done with standard techniques using a 1:100 dilution of the antibody and overnight incubations.

Following enteral dosing of rPH.2 in normal newborn rats, there was no measurable plasma PAF-AH activity at any time point using either the substrate incubation assay or the ELISA technique. With intraperitoneal administration of rPH.2, significant circulating PAF-AH activity was measurable using both methods by 1 hour after dosing, and this activity peaked at 6 hours. Higher doses of rPH.2 (from 3 to 75μ, 10 to 250 U) resulted in higher plasma PAF-AH activity. Immunohistochemical analysis revealed the presence of rPAF-AH product in the epithelial cells of the intestinal mucosa following enteral administration. The reactivity clustered mostly in the intestinal villi with minimal staining present in the crypt cells. There was more staining in the ileum than jejunum, and some rPAF-AH product was immunochemically identified in portions of colon. There was no demonstrable staining in any control samples or in specimens recovered from animals dosed via the intraperitoneal route. Thus, enteral administration of rPAF-AH product resulted in local mucosal epithelial accumulation of the enzyme without any measurable systemic absorption, while, in contrast, intraperitoneal administration of rPAF-AH product resulted in high circulating enzyme levels but no local mucosal accumulation.

In the NEC model, NEC was induced in newborn rats according to Caplan et al., *Pediatr. Pathol.*, 14:1017–1028 (1994). Briefly, animals were fed with newborn puppy formula reconstituted from powder (Esbiliac, Borden Inc) every three hours via a feeding tube. The feeding volume began at 0.1 ml/feed initially and advanced as tolerated to 0.4 ml/feed by the 4th day of the protocol. All animals were challenged with asphyxial insults twice daily by breathing 100% nitrogen for 50 seconds in a closed plastic chamber followed by exposure to cold (4° C.) for 10 minutes. Bowel and bladder function was stimulated with gentle manipulation after every feeding. Animals were maintained for 96 hours or until they showed signs of distress. Morbid animals had abdominal distention, bloody stools, respiratory distress, cyanosis, and lethargy, and were euthanized via decapitation. After sacrifice, the intestine of each rat was examined grossly for signs of necrosis and then formalin-fixed for later histological analysis. Specimens were paraffin-embedded, sectioned with a microtome, stained with hematoxylin and eosin, and examined in a blinded fashion by two observers. Intestinal injury was scored as 1+ for epithelial cell lifting or separation, 2+ for sloughing of epithelial cells to mid villous level, 3+ for necrosis of entire villi, and 4+ for transmural necrosis.

To assess the efficacy of rPH.2, three different groups of rats were treated with the compound via enteral delivery, intraperitoneal delivery or both. The rPH.2 preparation had 0.8 mg/ml protein and approximately 4000 Units/mg PAF-AH activity, with a <0.5 EU/mg endotoxin/protein ratio. Enterally dosed animals were given 25λ (80 U) of rPH.2 via the orogastric tube diluted into each feeding (every three hours). Intraperitoneally dosed animals were given 75λ by intraperitoneal injection twice daily. Control animals received appropriate volumes of buffer (20 mM $NaPO_4$, pH 7.4) without the rPH.2 and were studied simultaneously with each experimental group. Mortality and signs of NEC were evaluated for each treatment group, and differences were analyzed statistically using Fischer's Exact test. A p-value of <0.05 was considered significant. Results are shown in Table 9 below.

TABLE 9

|  | NEC | Death |
| --- | --- | --- |
| Control (i.p. admin.) | 7/10 | 8/10 |
| rPH.2 (240 U i.p. twice daily) | 6/11 | 8/11 |
| Control (enteral admin.) | 19/26 | 21/26 |
| rPH.2 (80 U enterally every 3 hours) | 6/26 | 7/26 |
| Control (i.p. + enteral admin.) | 10/17 | 12/17 |
| rPH.2 (240 U i.p. twice daily and 80 U enterally every 3 hours) | 3/14 | 7/14 |

Data represent cumulative results from four different experiments for i.p. dosing, four experiments for enteral dosing, and three experiments for i.p. + enteral dosing.

Enteral rPH.2 administration significantly reduced the incidence of both NEC and death compared to control animals. Results from four different enterally-dosed experiments showed that pretreatment with rPH.2 decreased NEC from 19/26 (control) to 6/26 (p<0.001). Intestinal injury was variable among treated and control animals, but in most cases was characterized by midvillous necrosis in some segments, total villous necrosis in other areas, occasional areas of transmural necrosis, and remaining portions of normal intestinal histology. The worst degree of NEC in treated animals and control animals with intestinal injury was similar (median score 2.8 in controls vs. 2.4 in rPH.2-treated rats, p>0.05).

Intraperitoneal dosing with rPH.2 had no significant impact on NEC or death in this model. The onset of symptoms was similar between this group and controls (40±5 hours in controls vs 36±7 hours in rPH.2-treated rats) and the degree of NEC in both groups was similar (median score 2.6 in controls vs. 2.5 in rPH.2-treated rats).

Additional experiments were done in which rats were dosed both enterally and intraperitoneally with rPH.2 at the same doses as the single treatment groups (25λ of rPH.2 in each feeding every three hours, plus 75λ by intraperitoneal injection twice daily). Results are shown above in Table 9. Although there were no significant differences between treated and control groups in the incidence of death, the rPH.2 treatment significantly reduced the incidence of NEC (10/17 in controls vs. 3/14 in rPH.2-treated rats, p=0.04). Of note, 6 out of the 7 animals who died in the rPH.2-treated group had positive blood cultures for *E. coli* obtained just prior to death.

These results further support the protective role of PAF-AH products in a neonatal model of non-PAF-induced NEC. Enteral treatment with rPAF-AH product prevented NEC while intraperitoneal treatment at these doses had no demonstrable effect. These findings suggest that PAF-AH product supplementation for formula-fed premature newborns at risk for NEC may reduce the incidence of this disease.

EXAMPLE 18

The efficacy of PAF-AH product in a guinea pig model of acute respiratory distress syndrome (ARDS) was examined.

Platelet-activating factor (PAF) injected intravenously into guinea pigs produces a profound lung inflammation reminiscent of early ARDS in humans. Within minutes after intravenous administration of PAF, the lung parenchyma becomes congested with constricted bronchi and bronchioles [Lellouch-Tubiana et al., supra. Platelets and polymorphonuclear neutrophils begin to marginate and cellular aggregates are easily identified along arterioles of the lung [Lellouch-Tubiana, *Br. J. Exp Path.*, 66:345–355 (1985)]. PAF infusion also damages bronchial epithelia cells which dissociate from the airway walls and accumulate in the airway lumens. This damage to airway epithelial cells is consistent with hyaline membrane formation that occurs in humans during the development of ARDS. Margination of the neutrophils and platelets is quickly followed by diapedesis of these cells into the alveolar septa and alveolar spaces of the lung. Cellular infiltrates elicited by PAF are accompanied by significant vascular leakage resulting in airway edema [Kirsch, *Exp. Lung Res.*, 18:447–459 (1992)]. Evidence of edema is further supported by in vitro studies where PAF induces a dose-dependent (10–1000 ng/ml) extravasation of $^{125}I$ labeled fibrinogen in perfused guinea pig lungs [Basran, *Br. J. Pharmacol.*, 77:437 (1982)].

Based on the above observations, an ARDS model in guinea pigs was developed. A cannula is placed into the jugular vein of anaesthetized male Hartly guinea pigs (approximately 350–400 grams) and PAF diluted in a 500 μl volume of phosphate buffered saline with 0.25% bovine serum albumin as a carrier (PBS-BSA) is infused over a 15 minute period of time at a total dosage ranging from 100–400 ng/kg. At various intervals following PAF infusion, animals are sacrificed and lung tissue is collected. In guinea pigs infused with PAF, dose dependent lung damage and inflammation is clearly evident by 15 minutes and continues to be present at 60 minutes. Neutrophils and red blood cells are present in the alveolar spaces of PAF treated guinea pigs but absent in control or sham infused animals. Evidence of epithelial cell damage is also evident and reminiscent of hyaline membrane formation in human ARDS patients. Protein determinations done on bronchoalveolar lavage (BAL) samples taken from guinea pigs infused with PAF shows a dramatic accumulation of protein in the inflamed lung, clear evidence of vascular leakage.

rPH.2 was found to completely protect against PAF mediated lung injury in the guinea pig model of ARDS. Groups of guinea pigs were pretreated with either rPH.2 (2000 units in 500 μl) or 500 μl of the PAF-AH buffer only. Fifteen minutes later these guinea pigs were infused with 400 ng/kg PAF in a 500 μl volume, infused over a 15 minute period. In addition, a sham group of guinea pigs was infused with 500 µl of PBS-BSA. At the completion of the PAF infusion the animals were sacrificed and BAL fluid was collected by lavaging the lungs 2× with 10 ml of saline containing 2 µ/ml heparin to prevent clotting. To determine protein concentration in the BAL, samples were diluted 1:10 in saline and the OD 280 was determined. BAL fluid from sham guinea pigs was found to have a protein concentration of 2.10±1.3 mg/ml. In sharp contrast, BAL fluid from animals infused with PAF was found to have a protein concentration of 12.55±1.65 mg/ml. In guinea pigs pretreated with rPH.2, BAL fluid was found to have a protein concentration of 1.13±0.25 mg/ml which is comparable to the sham controls and demonstrates that PAF-AH product completely blocks lung edema in response to PAF.

EXAMPLE 19

The efficacy of a PAF-AH product, rPH.2, was evaluated in two different models of acute pancreatitis.

A. Activity in a Rat Pancreatitis Model

Male Wistar rats (200–250 g) were purchased from Charles River Laboratories (Wilmington, Mass.). They were housed in a climate controlled room at 23±2° C. with a 12 hour light/dark cycle and fed standard laboratory chow with water ad libitum. Animals were randomly assigned to either control or experimental groups. Rats were anesthetized with 50 mg/kg pentobarbital sodium intraperitoneally, and a polyvinyl catheter (size V3, Biolab products, Lake Havasu, Ariz.) was placed by cutdown into the jugular vein. The catheter was tunneled subcutaneously to exit in the dorsal cervical area, and the animals were allowed to recover from anesthesia. The rats were given free access to water but were fasted overnight. Experiments were performed the next day on conscious animals. During the interim, catheter patency was maintained by constant infusion of saline (0.2 ml/h). On the day of the experiment, the animals were intravenously injected with rPH.2 or vehicle control, followed by an infusion of either (1) 5 µg/kg per hour of caerulein for 3.5 hours, or (2) 10 µg/kg per hour of caerulein for 5 hours, (Research Plus, Bayonne, N.J.). Immediately after completion of the infusion, the animals were anesthetized with pentobarbital sodium, their abdomens were opened, and 5 ml of blood aspirated from the inferior vena cava for subsequent assays. They were then sacrificed by exsanguination. Serum amylase, serum lipase and serum bilirubin were measured, and the pancreas was harvested. Pieces of pancreas were either fixed in a 4% phosphate buffered formaldehyde solution for histological examination or immediately deep frozen at −80° C. for measurements of myeloperoxidase activity. Additional pieces of pancreas were assessed for pancreatic water content and pancreatic amylase and trypsin as described below. Myeloperoxidase activity, a measure of neutrophil sequestration, was assessed in the pancreas and lung as described below. Pulmonary vascular permeability was also assessed as described below. Statistical analysis of the data was accomplished using unpaired Student's t-test. The data reported represent means+S.E.M. of at least three different experiments. Differences in the results were considered significant when p<0.05.

1. Pancreatic water content

Pancreas pieces were blotted dry and weighed (wet weight), and were then desiccated for 34 hrs at 120° C. and reweighed (dry weight). Pancreatic water content was calculated as the difference between wet and dry weight and expressed as a percentage of the pancreatic wet weight. A rise in pancreatic water content was considered to indicate the development of edema.

2. Serum and Pancreatic Amylase

Amylase activity in serum was measured using 4,6-ethylidene $(G_7)$-p-nitrophenyl $(G_1)$-$\alpha_1$D-maltoplaside (ET-$G_7$PNP) (Sigma Chemical Co., St. Louis, Mo.) as substrate according to Pierre et al., Clin. Chem., 22:1219 (1976). Amylase activity in pancreatic tissue homogenized in 10 mM phosphate buffer, pH 7.4, was measured using the same method.

3. Pancreatic Trypsin

Trypsin activity was measured fluorimetrically using Boc-Gin-Ala-Arg-MCA as the substrate. Briefly, 200 µl of the sample and 2.7 ml of 50 mM Tris-buffer (pH 8.0) containing 150 mM NaCl, 1 mM $CaCl_2$ and 0.1% bovine serum albumin were mixed in a cuvette. One hundred µl of substrate was added to the sample after 20 seconds of preincubation to start the reaction. The fluorescence reading was taken (excitation 380 nm, emission 440 nm) and expressed as slope. To allow pooling of data from different experiments trypsin activity in the fractions was expressed as percent of total trypsin activity.

4. Histology and Morphometry

For light microscopy, complete random cross-sections of the head, body and tail of the pancreas were fixed in 10% neutral phosphate-buffered formalin. Paraffin embedded-5 µm sections were stained with hematoxylin-eosin (H&E) and examined in a blinded fashion by an experienced morphologist. Acinar cell injury/necrosis was defined as either (a) the presence of acinar cell ghosts or (b) vacuolization and swelling of acinar cells and destruction of the histo-architecture of whole or parts of the acini, both of which had to be associated with an inflammatory reaction. The amount of acinar cell injury/necrosis and the total area occupied by acinar tissue were each quantitated morphometrically using computerized planimetric image analysis video unit (model CCD-72, Dage-MT1, Michigan city, Ind.) equipped with NIH-1200 image analysis software. Ten randomly chosen microscopic fields (125×) were examined for each tissue sample. The extent of acinar cell injury/necrosis was expressed as the percent of total acinar tissue which was occupied by areas which met the criteria for injury/necrosis.

5. Pancreas and Lung Myeloperoxidase (MPO) Activity Measurement

Neutrophil sequestration in pancreas and lung was evaluated by measurement of tissue myeloperoxidase activity. Tissue samples harvested at the time of sacrifice were stored at −70° C. until the time of assay. Samples (50 mg) were thawed and homogenized in 1 mL of 20 mM phosphate buffer (pH 7.4) and centrifuged (10,000×g, 10 min 4° C.). The resulting pellet was resuspended in 50 mM phosphate buffer (pH 6.0) containing 0.5% hexadecyltrimethylammonium bromide (Sigma, St. Louis, Mo.) and subjected to four cycles of freezing-thawing. The suspension was then further disrupted by sonication for 40 sec. and centrifuged (10,000× g, 5 min. at 4 ° C.). A reaction mixture consisting of the extracted enzyme, 1.6 mM tetramethylbenzidine (Sigma Chemical Co., St. Louis, Mo.), 80 mM sodium phosphate buffer (pH 5.4) and 0.3 mM hydrogen peroxide was incubated at 37° C. for 110 sec, and the absorbance was measured at 655 nm in a CobasBio autoanalyzer. This absorbance was then corrected for the fraction dry weight of the tissue sample.

6. Measurement of Pulmonary Vascular Permeability

Obstruction of the common biliopancreatic duct also typically results in severe pancreatitis-associated lung injury quantifiable by lung vascular permeability and histological examination.

Two hours before the animals were killed, an intravenous bolus injection of 5 mg/kg fluorescein isothiocyanate albumin (FITC-albumin, Sigma Chemical Co., St. Louis, Mo.) was given. Pulmonary microvascular permeability was evaluated by quantifying the leakage of FITC-albumin from the vascular compartment into the bronchoalveolar space. Briefly, just after sacrifice, the right bronchus was blocked using a clamp and the trachea exposed. Subsequently, the right lung was lavaged by using a cannula inserted into the trachea. Three washes of saline (60 ml lavage) were pooled and the FITC fluorescence in serum and lavage was measured at excitation 494 nm and emission 520 nm. The fluorescence ratio of lavage fluid to blood was calculated and taken as a measure of microvascular permeability in the lung. The lung was also stained with H&E and examined histologically.

7. Effect of Caerulein and rPH.2 administration

Infusion of caerulein alone at 5 $\mu$g/kg/h for 3.5 hours resulted in a typical mild secretagogue-induced pancreatitis in the rats, which was characterized by hyperamylasemia, pancreatic edema as measured by pancreatic water content, and histological changes including marked acinar cell vacuolization and pancreatic edema. Saline infusion in control animals did not result in any of these biochemical or histological changes. Administration of rPH.2 intravenously at doses of 5, 10 or 20 mg/kg 30 min. before the start of caerulein infusion did not significantly alter the magnitude of the changes in pancreatic edema (water content) and histology that were induced by infusion of caerulein alone. Administration of rPH.2 also had no effect on caerulein-induced activation of pancreatic trypsinogen or amylase content.

Infusion of a higher dose of caerulein, 10 $\mu$g/kg/h for 5 hours, to rats resulted in a more severe pancreatitis, characterized relative to the controls by a more pronounced increase in serum amylase activity and pancreatic edema, a marked increase in pancreatic MPO activity, and a significant increase in trypsinogen activation and amylase activity in the pancreas. Pancreatic histology indicated not only pancreatic edema and acinar cell vacuolization but also some patchy necrosis and a few infiltrating cells.

Administration of rPH.2 (5 or 10 mg/kg intravenously) 30 min. before the start of caerulein (10 $\mu$g/kg/h) infusion ameliorated the magnitude of many of the pancreatic changes induced by the infusion of caerulein alone. Results are shown in Table 10 below. rPH.2 treatment at a dose of 5 mg/kg resulted in decrease of serum amylase activity (from 10984±1412 to 6763±1256). The higher 10 mg/kg dose of rPH.2 did not result in further improvement of hyperamylasemia. Treatment with either 5 or 10 mg/kg rPH.2 also resulted in some decrease in caerulein-induced development of pancreatic edema as measured by water content (90.61±0.27 for caerulein alone vs. 88.21±0.61 for caerulein +5 mg/kg rPH.2). The 5 mg/kg dose of rPH.2 provided a significant amelioration of pancreatic MPO activity (2.92±0.32 fold increase over controls for caerulein alone vs. 1.19±0.21 for caerulein with rPH.2, $p<0.05$). Higher doses of rPH.2 did not result in further improvement of MPO activity. Neither dose of rPH.2 significantly altered the extent of trypsinogen activation or the amylase content in the pancreas. Pancreatic histology indicated some improvement in microscopic necrosis and infiltration after rPH.2 pretreatment.

Pancreatitis associated lung injury has been observed both clinically and in several models of pancreatitis. Infusion of caerulein at 5 $\mu$g/kg/h for 3.5 h, which resulted in a mild form of pancreatitis, did not result in significant injury to the lungs. However, infusion of caerulein at 10 $\mu$g/kg/h for 5 hours, which resulted in more severe pancreatitis, also resulted in lung injury quantified by increased lung vascular permeability (0.31±0.04 to 0.79±0.09), lung MPO activity (indicating neutrophil sequestration) and neutrophil infiltration on histological examination.

Administration of rPH.2 at a dose of 5 mg/kg 30 min prior to caerulein infusion significantly ameliorated the rise in lung MPO activity induced by the infusion of caerulein alone (3.55±0.93 for caerulein alone vs. 1.51±0.26 for caerulein with rPH.2). rPH.2 treatment significantly decreased the severity of microscopic changes observed in the luig tissue after caerulein infusion. The caerulein-induced increase in lung vascular permeability was reduced by rPH.2 treatment, although not statistically significant. The higher 10 mg/kg dose of rPH.2 was no more effective than the lower dose in decreasing the severity of caerulein-induced lung injury.

TABLE 10

|  | Control (no CER) | Caerulein (CER) 10 $\mu$g/kg/h | CER + 5 mg/kg rPH.2 | CER + 10 mg/kg rPH.2 |
|---|---|---|---|---|
| Serum Amylase (U/l) | 961 ± 174 | 10984 ± 1412 | 6763 ± 1256 | 8576 ± 1024 |
| Pancreas Water Content (% wet weight) | 72.71 ± 0.64 | 90.61 ± 0.27 | 88.21 ± 0.61 | 89.00 ± 0.94 |
| Pancreas MPO (fold increase over control) | 1.0 | 2.92 ± 0.32 | 1.19 ± 0.21 | 1.42 ± 0.19 |
| Pancreas Trypsin Activity (1000 × slope/ $\mu$g DNA | 0.12 ± 0.06 | 9.70 ± 2.50 | 8.33 ± 1.75 | 9.15 ± 1.28 |
| Pancreas Amylase Content (U/$\mu$g DNA) | 0.28 ± 0.06 | 0.42 ± 0.07 | 0.45 ± 0.04 | 0.46 ± 0.044 |
| Lung Vascular Permeability (Lavage/Serum %) | 0.31 ± 0.04 | 0.79 ± 0.09 | 0.70 ± 0.09 | 0.70 ± 0.07 |
| Lung MPO (fold increase over control) | 1.0 | 3.55 ± 0.93 | 1.51 ± 0.26 | 1.64 ± 0.22 |

B. Activity in an Opossum Pancreatitis Model

Healthy, randomly trapped American opossums (*Didelphis virginiana*) of either sex (2.0 kg to 4.0 kg) were obtained from Scott-Haas and housed in climate controlled rooms at 23±2° C. with a 12 hour light/dark cycle and fed a standard laboratory chow with water ad libitum. After an overnight fast, the animals were anesthetized with 50mg/kg sodium-pentobarbital i.p. (Veterinary Laboratories Inc., lenexa, Kans.). A celiotomy was performed through a midline incision under sterile conditions and the common bile pancreatic duct was ligated in all animals to induce acute necrotizing pancreatitis. Additionally, the cystic duct was ligated to prevent the gallbladder from serving as a bile reservoir. The animals were randomly assigned to either control or experimental groups. Starting at Day 2 after ligation of the pancreatic duct, the experimental group received 5 mg/kg body weight per day of rPH.2 (supplied in a 4 mg/ml solution) intravenously via the tail vein, while the control group received an intravenous injection of the same volume of placebo vehicle only. After 1 and 2 days of treatment (at Day 3 and Day 4 after ligation of the pancreatic duct) the animals were euthanized by a sodium-pentobarbital overdose. Blood samples were drawn from the heart for measurements of serum amylase, serum lipase and serum bilirubin, and the pancreas was harvested. Pieces of pancreas were either fixed in a 4% phosphate buffered formaldehyde solution for histological examination or immediately deep frozen at −80° C. for measurements of myeloperoxidase activity. Additional pieces of pancreas were assessed for pancreatic water content and pancreatic amylase as described above in section A of this example. Myeloperoxidase activity, a measure of neutrophil sequestration, was assessed in the pancreas as described above. Pulmonary vascular permeability was also assessed as described above.

The results reported represent mean±standard error of the mean (SEM) values obtained from multiple determinations in 3 or more separate experiments. The significance of changes was evaluated using Student's t-test when the data consisted of only two groups or by analysis of variance (ANOVA) when comparing three or more groups. If ANOVA indicated a significant difference, the data were analyzed using Tukey's method as a post hoc test for the difference between groups. A p-value of <0.05 was considered to indicate a significant difference.

Results are shown in Table 11. Obstruction of the common biliopancreatic duct resulted in severe necrotizing pancreatitis characterized by hyperamylasemia, hyperlipasemia and extensive necrosis of the pancreas. Furthermore, obstruction of the common biliopancreatic duct was associated with an marked increase in serum bilirubin levels. Intravenous administration of rPH.2 (5 mg/kg/day) starting at Day 2 after ligation of the pancreatic duct ameliorated the magnitude of many of the pancreatic changes induced by duct obstruction and placebo treatment alone. One day of rPH.2 treatment reduced serum amylase levels in comparison to placebo treated animals, although the difference was not statistically significant, and two days of rPH.2 treatment (at Day 4 after ligation of the pancreatic duct) significantly reduced serum amylase levels compared to placebo. One or two days of rPH.2 treatment reduced serum lipase levels relative to controls, although the difference was not statistically significant. Two days of rPH.2 treatment reduced pancreatic amylase content relative to controls, although one day of treatment resulted in an increase in pancreatic amylase. Treatment with rPH.2 was not observed to affect serum bilirubin levels, pancreas myeloperoxidase activity or pancreas water content.

The major characteristic histological changes induced by obstruction of the biliopancreatic duct included marked necrosis, infiltration of inflammatory cells, acinar cell vacuolization, and marked distention of the acinar lumina. Morphometrical examination of the pancreas for acinar cell injury showed a major protective effect of rPH.2 on the pancreas after one and two days of rPH.2 treatment. After one day of rPH.2 treatment, the acinar cell injury was reduced to about 23% of total acinar cell tissue, compared to 48% injury for the placebo-treated animals. This reduction of acinar cell injury was even more pronounced after two days of treatment, at which time rPH.2 treatment resulted in about 35% injury of the total acinar cell tissue, compared to about 60% injury for the placebo-treated animals.

Lung vascular permeability, quantified by FITC injection showed a highly significant difference after one and two days of rPH.2 treatment compared to placebo group. Histological examination of the lung showed severe lung injury in all placebo-treated animals. Lung injury was characterized by an extensive inflammatory response with interstitial and intraalveolar infiltration of mainly macrophages, lymphocytes and neutrophils, and by a patchy but marked interstitial edema and thickening of the alveolar membranes. Administration of rPH.2 resulted in a marked decrease of infiltration of inflammatory cells and a reduction of interstitial edema at all times.

In summary, these results showed that administration of rPH.2 intravenously at a dose of 5 mg/kg/day beginning at 48 hours after ligation of the pancreatic duct resulted in significant amelioration of the increase in blood levels of amylase and lipase and acinar cell injury as quantitated by morphometric analysis of H&E stained sections, and a significant decrease in the severity of pancreatitis-induced lung injury. Administration of rPAF-AH product in this clinically relevant model of pancreatitis showed beneficial effects in decreasing the severity of pancreatitis.

TABLE 11

| | After 1 day of treatment (Sacrifice at Day 3) | | After 2 days of treatment (Sacrifice at Day 4) | |
|---|---|---|---|---|
| | Placebo | rPH.2.5 mg/kg | Placebo | rPH.2 5 mg/kg |
| Serum bilirubin (mg/dl) | 5.49 ± 0.96 | 7.10 ± 0.60 | 6.54 ± 0.55 | 4.91 ± 0.79 |
| Serum amylase (U/l) | 5618 ± 899 | 4288 ± 675 | 6538 ± 1355 | 3106 ± 467* |
| Serum lipase (U/l) | 2226 ± 554 | 1241 ± 263 | 1424 ± 257 | 1023 ± 295 |
| Pancreas Water Content (%) | 81.10 ± 0.56 | 81.52 ± 0.79 | 80.05 ± 1.07 | 79.32 ± 0.49 |
| Pancreas MPO (OD/fraction dry weight) | 1345 ± 286 | 1142 ± 83 | 1149 ± 232 | 1033 ± 130 |
| Pancreatic Amylase (U/μg DNA) | 706 ± 92 | 1101 ± 105 | 950 ± 85 | 712 ± 131 |
| Lung Vascular Permeability (FITC Lavage/ Serum %) | 0.76 ± 0.09 | 0.21 ± 0.04** | 0.57 ± 0.13 | 0.23 ± 0.04* |
| Acinar Cell Injury (% of Total Acinar Tissue) | 48% | 23% | 60% | 35% |

*p = 0.02 vs. placebo
**p < 0.001 vs. placebo

EXAMPLE 20

A study was conducted to evaluate the effect of a PAF-AH product, rPH.2, on neurotoxicity associated with HIV infection. Human immunodeficiency virus type 1 (HIV-1) infection of the central nervous system results in neuronal loss by apoptosis. HIV-1-infected monocytes activated by a variety of antigenic stimuli, including contact with neural cells, secrete high levels of neurotoxic pro-inflammatory cytokines, including PAF. The effect of rPH.2 on the neurotoxicity of conditioned media from HIV-infected and activated monocytes was assessed.

Monocytes were infected with HIV and activated as follows. Monocytes were recovered from peripheral bone marrow cells (PBMC) of HIV- and hepatitis B-seronegative donors after leukopheresis and purified (>98%) by countercurrent centrifugal elutriation as described in Genis et al., *J. Exp. Med.*, 176:1703–1718 (1992). Cells were cultured as adherent monolayers ($1 \times 10^4$ cells/ml in T-75 culture flasks) in DMEM (Sigma, St. Louis, Mo.) with recombinant human macrophage colony stimulatory factor (MSCF) (Genetics Institute, Inc. Cambridge, Mass.). Under these conditions, monocytes differentiate into macrophages. After 7–10 days of culture, macrophages were exposed to HIV-1$_{ADA}$ (accession number M60472) at a multiplicity of infection (MOI) of 0.01 infectious virions/target cell. Under these conditions, 20–50% of the monocytes were infected at 7 days after HIV-1 inoculation, as determined by immunofluorescent and in situ hybridization techniques [Kalter et al.,

*J. Immunol.*, 146:298–306 (1991)]. All cultures were refed with fresh medium every 2 to 3 days. Five to seven days after HIV-1 infection and during the peak of reverse transcriptase activity ($10^7$ cpm/ml), assessed according to Kalter et al., supra, cultures of HIV-1-infected and parallel cultures of uninfected monocytes were stimulated with LPS (10 ng/ml) or vehicle for 30 min. at 37° C., then snap-frozen at −80° C. until used in the neurotoxicity assay.

Human cerebral cortical neuron cell cultures were established as follows. Human fetal brain tissue was obtained from the telencephalon of second trimester (13–16 weeks gestation) human fetal brain tissue according to a modified procedure of Banker and Cowan, *Brain Res.*, 126:397–425 (1977). Briefly, brain tissue was collected, washed in 30 ml of cold Hank's BSS (containing $Ca^{+2}$ and $Mg^{+2}$+25 mM HEPES, and 5× gentamicin), separated from adherent meninges and blood, and cut into 2 $mm^3$ pieces. The tissue was forced through a 230 μM Nitex bag and gently triturated through a flame-polished Pasteur pipet 10–15 times. The tissue was centrifuged at 550 rpm, 5 minutes, 4° C., and the pellet was resuspended in 5–10 ml of MEM-hipp (D-glucose, 5 grams/liter; L-glutamine, 2 mM; HEPES, 10 mM; Na pyruvate, 1 mM; KCl, 20 mM) containing N1 components (insulin, 5 mg/l; transferrin, 5 mg/l; selenite, 5 μg/l, progesterone 20 nM; putrescine, 100 μM), as well as 10% fetal calf serum (FCS), PSN antibiotic mix (penicilin, 50 mg/l; streptomycin, 50 mg/l; neomycin, 100 mg/l), and fungizone (2.5 mg/l). The cell count and viability were determined by diluting Hank's BSS with 0.4% trypan blue (1:1 v/v) and counting with a hemocytometer. Cells were tently triturated 5 times with a 10 ml pipet and plated at a density of 105 cells/12 mm glass coverslip pre-coated with poly-L-lysine (70K–150K MW, Sigma, St. Louis, Mo.) placed in 24 well culture dishes. One ml of media was pipetted into each culture well. Cells were cultured for 10–28 days at 37° C. in a humidified atmosphere of 5% $CO_2$/95% air, changing media every 3 days. Under these conditions, cultures were >60–70% homogeneous for neurons, with 20–30% astrocytes, <1% microglia and ~10% macrophage and microglia staining. After 14–28 days of culture, neuronal cultures express sufficient levels of N-methyl-D-aspartate (NMDA) or non-NMDA receptors to die after excitotoxic doses of NMDA or alpha-amino-3-hydroxy-5-methyl-4 isoxazole proprionic acid (AMPA).

Figure 13:
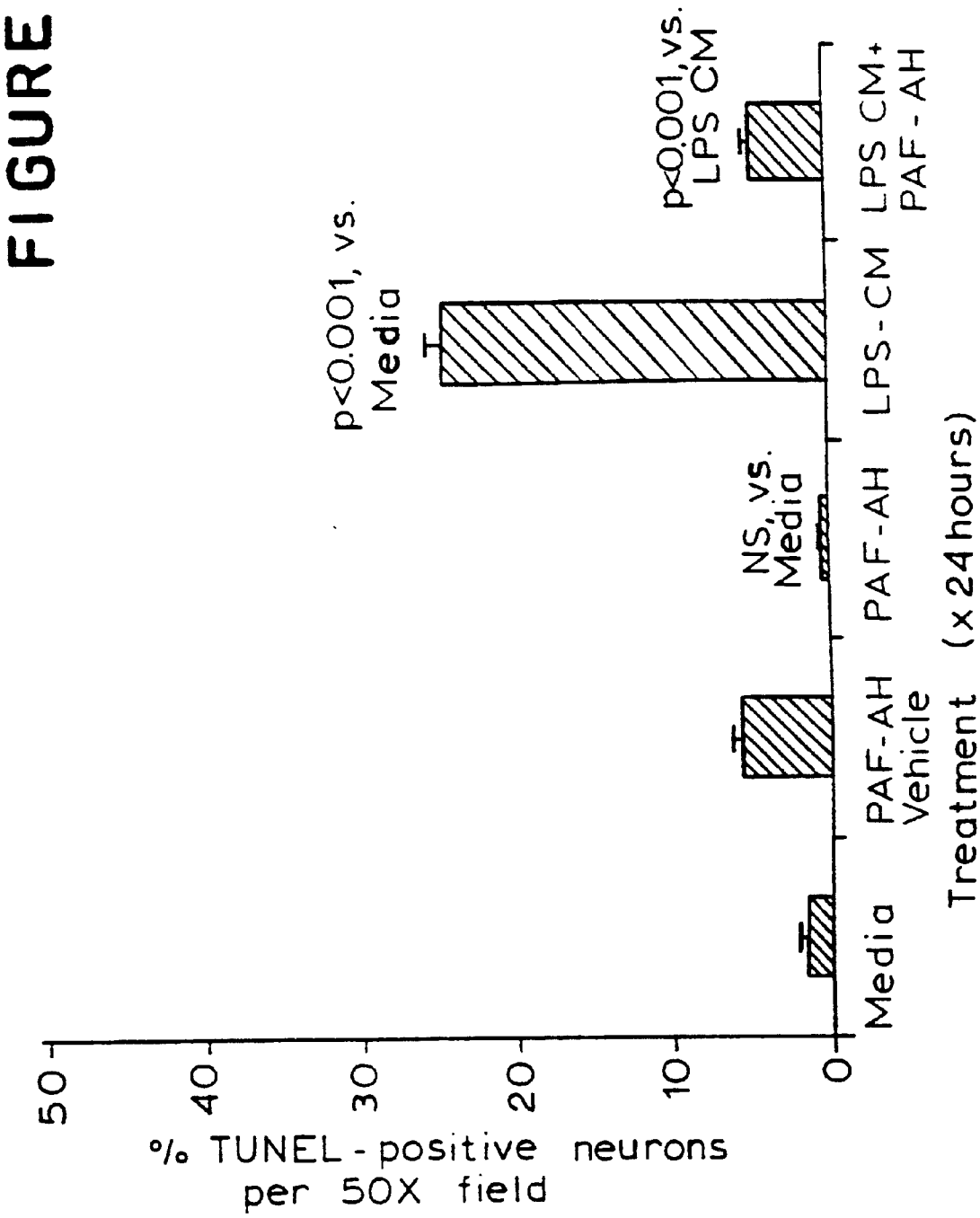
FIG. 13 presents results indicating that PAF-AH neutralizes the apoptotic effects of conditioned media from HIV-1-infected and activated monocytes.

The neurotoxicity assay was conducted as follows. The test samples, which were (a) conditioned media from LPS-stimulated HIV-1 infected monocytes, (b) control media, (c) conditioned media with added rPH.2 at 51 μg/ml or (d) conditioned media with added vehicle for rPH.2, were applied to the neuronal cell cultures at a 1:10 v/v concentration for 24 hours. Neurotoxicity was measured by identifying apoptotic nuclei in situ on neuronal coverslips fixed in 4% paraformaldehyde, employing a commercial kit (Apop Tag; ONCOR, Gaithersburg, Md.) that uses terminal deoxynucleotidyl transferase (TdT) to bind digoxigenin-dUPT to free 3'-OH ends of newly cleaved DNA (TUNEL staining). Digitized images of TUNEL-stained neurons in ≧15 randomly selected microscopic fields were analyzed for number of TUNEL-stained nuclei/number of total neurons per 50× field using computerized morphometry (MCID, Imaging Research, St. Catherine, Ontario, Canada). Data were expressed at % neuronal nuclei positive for TUNEL staining±SEM and are shown in FIG. 13. Tests of statistical significance between control and experimental treatments were determined by ANOVA or paired t-tests, with significance at $p \leq 0.05$. Quantitation of these cultures confirmed that conditioned media from HIV-infected and activated monocytes induced neuronal cell death in nearly 25% of the total population of cerebral cortical neurons, and rPH.2 was able to reduce this toxicity to less than 5% of the total neurons. The rPH.2 by itself was not neurotoxic, since 50 μg/ml rPH.2 had no effect on neuronal cell death relative to cultures treated with control media. These results clearly indicate that a major component of the neurotoxicity induced by application of conditioned media from activated HIV-1 infected monocytes must be due to PAF, since neurotoxicity can be almost completely abrogated by co-incubation with PAF-AH product, the enzyme responsible for metabolism of PAF in the central nervous system. These findings suggest potential therapeutic interventions in the treatment of the CNS neurologic disease associated with HVI-1 infection.

EXAMPLE 21

Nearly four percent of the Japanese population has low or undetectable levels of PAF-AH activity in their plasma. This deficiency has been correlated with severe respiratory symptoms in asthmatic children [Miwa et al., *J. Clin. Invest,.* 82: 1983–1991 (1988)] who appear to have inherited the deficiency in an autosomal recessive manner.

To determine if the deficiency arises from an inactive but present enzyme or from an inability to synthesize PAF-AH, plasma from multiple patients deficient in PAF-AH activity was assayed both for PAF-AH activity (by the method described in Example 10 for transfectants) and for the presence of PAF-AH using the monoclonal antibodies 90G11D and 90F2D (Example 13) in a sandwich ELISA as follows. Immulon 4 flat bottom plates (Dynatech, Chantilly, Va.) were coated with 100 ng/well of monoclonal antibody 90G11D and stored overnight. The plates were blocked for 1 hour at room temperature with 0.5% fish skin gelatin (Sigma) diluted in CMF-PBS and then washed three times. Patient plasma was diluted in PBS containing 15 mM CHAPS and added to each well of the plates (50 μl/well). The plates were incubated for 1 hour at room temperature and washed four times. Fifty μl of 5 μg/ml monoclonal antibody 90F2D, which was biotinylated by standard methods and diluted in PBST, was added to each well, and the plates were incubated for 1 hour at room temperature and then washed three times. Fifty μl of ExtraAvidin (Sigma) diluted 1/1000 in CMF-PBST was subsequently added to each well and plates were incubated for 1 hour at room temperature before development.

A direct correlation between PAF-AH activity and enzyme levels was observed. An absence of activity in a patient's serum was reflected by an absence of detectable enzyme. Similarly, plasma samples with half the normal activity contained half the normal levels of PAF-AH. These observations suggested that the deficiency of PAF-AH activity was due to an inability to synthesize the enzyme or due to an inactive enzyme which the monoclonal antibodies did not recognize.

Further experiments revealed that the deficiency was due to a genetic lesion in the human plasma PAF-AH gene. Genomic DNA from PAF-AH deficient individuals was isolated and used as template for PCR reactions with PAF-AH gene specific primers. Each of the coding sequence exons were initially amplified and sequenced from one individual. A single nucleotide change within exon 9 was observed (a G to T at position 996 of SEQ ID NO: 7). The nucleotide change results in an amino acid substitution of a phenylalanine for a valine at position 279 of the PAF-AH sequence (V279F). Exon 9 was amplified from genomic DNA from an additional eleven PAF-AH deficient individuals who were found to have the same point mutation.

To test whether this mutation crippled the enzyme, an *E. coli* expression construct containing the mutation was generated by methods similar to that described in Example 10. When introduced into *E. coli*, the expression construct generated no PAF-AH activity while a control construct lacking the mutation was fully active. This amino acid substitution presumably results in a structural modification which causes the observed deficiency of activity and lack of immunoreactivity with the PAF-AH antibodies of the invention.

PAF-AH specific antibodies of the invention may thus be used in diagnostic methods to detect abnormal levels of PAF-AH in serum (normal levels are about 1 to 5 U/ml) and to follow the progression of treatment of pathological conditions with PAF-AH. Moreover, identification of a genetic lesion in the PAF-AH gene allows for genetic screening for the PAF-AH deficiency exhibited by the Japanese patients. The mutation causes the gain of a restriction endonuclease site (Mae II) and thus allows for the simple method of Restriction Fragment Length Polymorphism (RFLP) analysis to differentiate between active and mutant alleles. See Lewin, pp. 136–141 in *Genes V*, Oxford University Press, New York, N.Y. (1994).

Screening of genomic DNA from twelve PAF-AH deficient patients was carried out by digestion of the DNA with MaeII, Southern blotting, and hybridization with an exon 9 probe (nucleotides 1–396 of SEQ ID NO: 17). All patients were found to have RFLPs consistent with the mutant allele.

While the present invention has been described in terms of specific embodiments, it is understood that variations and modifications will occur to those skilled in the art. Accordingly, only such limitations as appear in the appended claims should be placed on the invention.

We claim:

1. A PAF-AH polypeptide fragment lacking up to nineteen N-terminal amino acids of the mature human PAF-AH amino acid sequence of SEQ ID NO: 8.

2. The PAF-AH polypeptide fragment of claim 1 selected from the group consisting of:
   (a) a polypeptide having $Met_{46}$ of SEQ ID NO: 8 as the initial N-terminal residue;
   (b) a polypeptide having $Ala_{47}$ of SEQ ID NO: 8 as the initial N-terminal residue; and
   (c) a polypeptide having $Ala_{48}$ of SEQ ID NO: 8 as the initial N-terminal residue.

3. A PAF-AH polypeptide fragment lacking up to thirty C-terminal amino acids of the mature human PAF-AH amino acid sequence of SEQ ID NO: 8.

4. The PAF-AH polypeptide fragment of claim 3 having $Ile_{429}$ or $Leu_{431}$ as its C-terminal residue.

5. The PAF-AH fragment of claim 2 having as its C-terminal residue a residue of SEQ ID NO: 8 selected from the group consisting of:
   (a) $Ile_{429}$;
   (b) $Leu_{431}$; and
   (c) $Asn_{441}$.

6. A PAF-AH polypeptide variant which is an amino acid replacement variant having an amino acid replacement in the sequence of SEQ ID NO: 8 selected from the group consisting of:
   (a) S 108 A;
   (b) S 273 A;
   (c) D 286 A;
   (d) D 286 N;
   (e) D 296 A;
   (f) D 304 A;
   (g) D 338 A;
   (h) H 351 A;
   (I) H 395 A;
   (j) H 399 A;
   (k) C 67 S;
   (l) C 229 S;
   (m) C 291 S;
   (n) C 334 S; and,
   (o) C 407 S.

7. A PAF-AH polypeptide fragment, variant or variant fragment that hydrolyzes $^3$H-acetate from PAF produced by growing a host cell transformed or transfected with a DNA and isolating said PAF-AH polypeptide fragment, variant or variant fragment from said host cell or the medium of its growth, wherein said DNA is selected from the group consisting of:
   (a) a DNA encoding the amino acid sequence of SEQ ID NO: 8, and,
   (b) a DNA which hybridizes under stringent conditions to the non-coding strand of (a).

8. The PAF-AH polypeptyde fragment of claim 5 having $Met_{46}$ of SEQ ID NO: 8 as the initial N-terminal residue and having $Ile_{429}$ of SEQ ID NO: 8 as the C-terminal residue.

9. A PAF-AH polypeptide fragment, variant or variant fragment that hydrolyzes $^3$H-acetate from PAF produced by growing a host cell transformed or transfected with a DNA and isolating said PAF-AH polypeptide fragment, variant or variant fragment from said host cell or the medium of its growth, wherein said DNA is selected from the group consisting of:
   (a) a DNA comprising the sequence set out in SEQ ID NO: 7, and
   (b) a DNA which hybridizes under stringent conditions to the non-coding strand of (a).

* * * * *